(12) United States Patent
Delcour et al.

(10) Patent No.: US 6,936,703 B2
(45) Date of Patent: Aug. 30, 2005

(54) BIOCATALYST INHIBITORS

(75) Inventors: Jan Delcour, Heverlee (BE); Winok Debyser, Grimbergen (BE); Kurt Gebruers, Westerlo (BE); Hans Goesaert, Haacht (BE); Katleen Fierens, Bertem (BE); Johan Robben, Leuven (BE); Steven Van Campenhout, Heogaarden (BE)

(73) Assignee: K.U. Leuven Research and Development, Leuven (BE)

( * ) Notice: Subject to any disclaimer, the term of this patent is extended or adjusted under 35 U.S.C. 154(b) by 133 days.

(21) Appl. No.: 10/311,886

(22) PCT Filed: Jun. 21, 2001

(86) PCT No.: PCT/BE01/00106

§ 371 (c)(1),
(2), (4) Date: Dec. 23, 2002

(87) PCT Pub. No.: WO01/98474

PCT Pub. Date: Dec. 27, 2001

(65) Prior Publication Data

US 2003/0195151 A1 Oct. 16, 2003

(30) Foreign Application Priority Data

Jun. 22, 2000 (GB) .............................................. 0015296
Jan. 25, 2001 (GB) .............................................. 0102018
Jan. 26, 2001 (GB) .............................................. 0102194
Mar. 16, 2001 (GB) .............................................. 0106564
May 21, 2001 (GB) .............................................. 0112328

(51) Int. Cl.$^7$ ........................ C12N 15/11; A61K 35/78; C07K 14/00
(52) U.S. Cl. ........................ 536/23.1; 530/372; 530/350
(58) Field of Search .......................... 530/372; 536/23.6

(56) References Cited

U.S. PATENT DOCUMENTS 6,265,201 B1   7/2001   Wackett et al. ............ 435/252.3
6,267,956 B1   7/2001   Gomes et al. ............... 424/94.1
6,277,612 B1   8/2001   Golightly et al. ........... 435/190

FOREIGN PATENT DOCUMENTS

| EP | 0 979 830 | 2/2000 | |
|----|-----------|--------|---|
| WO | PCT/EP98/02590 | * 5/1998 | |
| WO | 98 49278 | 11/1998 | |
| WO | WO 9849278 A1 | * 11/1998 | ............ C12N/9/24 |
| WO | 00 39289 | 7/2000 | |

OTHER PUBLICATIONS

Juge et al., "Secretion, purification, and characterisation of barley alpha–amlylase produced by heterologous gene expression in *Aspergillus niger*", 1998, 49, 385–392.*

Debyser W et al: "Triticum Zestivum Xylanase Inhibitor (Taxi), a New Class of Enzyme Inhibitor Affecting Bread-making Performance" Journal of Cereal Science, Academic Press Ltd. XX, vol. 30, No. 1, Jul. 1999, pp. 39–43; XP000925298 ISSN: 0733–510 cited in the application the whole document.

McLauchlan W R et al: "A Novel Class of Protein from Wheat Which Inhibits Xylanases" Biochemical Journal, Portland Press, London, GB, vol. 338, No. 2, Mar. 1, 1999, pp. 441–446, XP000925393 ISSN: 0264–6021 the whole document.

Gebruers Kurt et al: "*Triticum aestivum* L. endoxyanase inhibitor (TAXI) consists of two inhibitors, TAXI I andTAXI II, with different specificities." Biochemical Journal. vol. 353, No. 2, 2001, pp. 239–244, XP001022202 ISSN: 0264–6021 the whole document.

Goesaert H et al: "Purification and partial characterization of an endoxylanase inhibitor from barley." Ceral Chemistry, vol. 78, No. 4, Jul. 2001, pp. 453–457, XP001033832 ISSN:009–0352 the whole document.

McLaughlan et al, (2000) $2^{nd}$ European Symposium on Enzymes in Grain Processing, pp 55–61.

Ham et al., Plant J., Feb. 1997, vol. 11(2), pp. 169–179.

Jones et al., Biochem Biophys Res. Commun., Oct. 30, 1981, vol. 102, pp. 1310–1316.

Bailey et al., World J. of Microbiology & Biotechnology, 9, 80–84 (1993).

Ziser et al., "Syntheses and testing of substrates and mechanism–based inactivators for xylanases", Carbohydrate Research 2741, (1995), 137–153.

Keskar et al., "Characterization and sequencing of an active–site cysteine–containing peptide from the xylanase of a thermotolerant Streptomyces", Biochem. J. (1992) 281, 601–605.

Paul et al, "Influence of Sugars on Endoglucanase and β–Xylanase Activities of a Bacillus Strain", Microbiology Unit, School of Life Sciences, XP–002078669, Biotechnology letters (1990) 12(1), 61–64.

Debyser et al., "Arabinoxylan Solubiliation and Inhibition . . . ", J. Am. Soc. Brew Chem., 55(4):153–156, 1997.

Spurwayz et al., "Calcium Protects a Mesophilic Xylanase . . . ", J. Biol. Chem. (1997) 272 (28) 17523–17530.

* cited by examiner

Primary Examiner—Jon Weber
Assistant Examiner—Suzanne M. Mayer
(74) Attorney, Agent, or Firm—Nixon & Vanderhye P.C.

(57) ABSTRACT

The present invention concerns a method for the separation and/or isolation of inhibitors of cellulolytic, xylanolytic and/or beta-glucanolytic enzymes, inhibitors obtainable by said method, and process for obtaining micro-organism, plant or plant material wherein the activity of the inhibitor according to the invention is increased or reduced and to the use of the inhibitor, using the cited micro-organism, plant or plant material and/or the use of endoxylanases selected or modified using these inhibitors in a variety of process and applications.

13 Claims, 27 Drawing Sheets

| CCA | AGA | TCT | CTG | CCA | GTT | CTG | GCA | CCT | GTG | ACC | AAA | GAT | CCA |
|-----|-----|-----|-----|-----|-----|-----|-----|-----|-----|-----|-----|-----|-----|
| Pro | Arg | Ser | Leu | Pro | Val | Leu | Ala | Pro | Val | Thr | Lys | Asp | Pro |

TAXI SEQ ID No.21

| GCA | ACC | TCC | CTC | TAC | ACA | ATC | CCC | CTG | CCG | CAC | TTT |
|-----|-----|-----|-----|-----|-----|-----|-----|-----|-----|-----|-----|
| Ala | Thr | Ser | Leu | Tyr | Thr | Ile | Pro | Leu | Pro | His | Phe |

| ACG | GGT | TGC | GGC | GGC | CTG | TAA | AGA | TCT | AGG |
|-----|-----|-----|-----|-----|-----|-----|-----|-----|-----|
| Thr | Gly | Cys | Gly | Gly | Leu | Stop | Arg | Ser | Arg |

Figure 21

```
Thioredoxin                              Enterokinase recognition site
AAC  CTG  GCC  GGC  TCT  GGA  TCC  GGT  GAT  GAC  GAT  GAC  AAG  CTC
Asn  Leu  Ala  Gly  Ser  Gly  Ser  Gly  Asp  Asp  Asp  Asp  Lys  Leu PCR product
GCC  CTT  CCA  AGA  TCT  CTG  CCA_____  CTG  TAA  AGA  TCT  AGG  AAG
Ala  Leu  Pro  Arg  Ser  Leu  Pro        Leu  Stop Arg  Ser  Arg  Lys
```

Thioredoxin — EK site — Leu Ala Leu Pro Arg Ser — TAXI

B

Ala Asn Thr Pro G

```
                              PelB
      ─────────────────────────────────────────────────────────
TTA   TTA   CTC   GCG   GCC   CAG   CCG   GCC   ATG   GCT   GCC   AAC   ACA   CCC
Leu   Leu   Leu   Ala   Ala   Gln   Pro   Ala   Met   Ala   Ala   Asn   Thr   Pro
                                    PCR product
      ─────────────────────────────────────────────────────────
GGG   AGA   TCT   CTG   CCA ................   GGC   CTG   TAA   AGA   TCT   TTC   GAA
Gly   Arg   Ser   Leu   Pro                    Gly   Leu   Stop  Arg   Ser   Phe   Glu
```

Figure 25

|       | malE |     |     |     |     |     | Factor Xa recognition site |     |     |     |     |     |     |
|-------|------|-----|-----|-----|-----|-----|------|-----|-----|-----|-----|-----|-----|
| AAC   | AAT  | AAC | AAC | AAC | CTC | GGG | ATC  | GAG | GGA | AGG | ATT | TCA | GAA |
| Asn   | Asn  | Asn | Asn | Asn | Leu | Gly | Ile  | Glu | Gly | Arg | Ile | Ser | Glu |

|     |     | PCR product |     |     |     |     |      |     |     |     |
|-----|-----|-----|-----|-----|-----|-----|------|-----|-----|-----|
| TTC | GGA | TCT | CTG | CCA | ......... | GGC | CTG | TAA | AGA | TCC | TCT | AGA |
| Phe | Gly | Ser | Leu | Pro |     | Gly | Leu | Stop | Arg | Ser | Ser | Arg |

Figure 26

BIOCATALYST INHIBITORS

This application is the U.S. national phase of international application PCT/BE01/00106 filed 21 Jun. 2001 which designated the U.S.

FIELD OF THE INVENTION

This invention relates to a method for the separation and/or isolation of inhibitors of cellulolytic, xylanolytic and/or β-glucanolytic enzymes (sometimes also referred to as cellulases (EC: 3.2.1.4), pentosanases and/or hemicellulases), especially inhibitors of pentosan degrading enzymes such as endoxylanase (such as EC: 3.2.1.8)(also referred to as xylanase), β-xylosidase (such as EC: 3.2.1.37), and α-L-arabinofuranosidase (such as EC: 3.2.1.55), to inhibitors of cellulase (such as EC: 3.2.1.4), β-glucanase (such as EC: 3.2.1.73 or such as 3.2.1.6), and to inhibitors of other xylan, arabinoxylan and β-glucan degrading enzymes, which are present in micro-organisms, plants, plant materials or fractions thereof, (such as cereals, cereal grains, cereal flours or fractions thereof). The method comprises the use of two or more enzymes, especially endoxylanases, during the screening for inhibition activity. In a preferred embodiment, one of the endoxylanases is from *Bacillus subtilis*.

This invention also relates to a method for the separation and/or isolation of inhibitors of cellulolytic, xylanolytic and/or β-glucanolytic enzymes (sometimes also referred to as cellulases (EC:3.2.1.4), pentosanases and/or hemicellulases), especially inhibitors of pentosan degrading enzymes such as endoxylanase (such as EC: 3.2.1.8)(also referred to as xylanase), β-xylosidase (such as EC: 3.2.1.37), and (-L-arabinofuranosidase (such as EC: 3.2.1.55), to inhibitors of cellulase (such as EC: 3.2.1.4), β-glucanase (such as EC: 3.2.1.73 or such as 3.2.1.6), and to inhibitors of other xylan, arabinoxylan and β-glucan degrading enzymes, which are present in micro-organisms, plants, plant materials or fractions thereof, (such as cereals, cereal grains, cereal flours or fractions thereof). The method comprises an affinity chromatographic step with immobilised enzymes, especially endoxylanases, and/or antibodies against the said inhibitors, especially antibodies against an endoxylanase inhibitor. In a preferred embodiment, the immobilised endoxylanases are those from *Bacillus subtilis* and/or *Aspergillus niger*.

The present invention is also related to inhibitors of cellulolytic, xylanolytic and/or β-glucanolytic enzymes (sometimes also referred to as cellulases (EC: 3.2.1.4), pentosanases and/or hemicellulases), especially inhibitors of pentosan degrading enzymes such as endoxylanase (such as EC: 3.2.1.8), β-xylosidase (such as EC: 3.2.1.37), and α-L-arabinofuranosidase (such as EC: 3.2.1.55), to inhibitors of cellulase (such as EC: 3.2.1.4), β-glucanase (such as EC: 3.2.1.73 or such as 3.2.1.6), and to inhibitors of other xylan, arabinoxylan and β-glucan degrading enzymes, obtainable by said methods, as well as to feed or food compositions comprising said inhibitors and to the use of said inhibitors for screening enzymes such as endoxylanases that are totally, more, less or not inhibited by said inhibitors or for modifying enzymes, such as endoxylanases in such way that they are totally, more, less or not inhibited by said inhibitors, as well as to the use of said inhibitors in different areas of food, feed and/or beverage technologies, such as malting and brewing, the production of animal feedstuffs such as to increase their conversion, the production of refrigerated and/or frozen doughs, such as to reduce syruping, the production of baked and/or extruded cereal products such as straight dough, sponge and dough (all said dough compositions comprising flour and water) and Chorleywood breads, breakfast cereals, different types of biscuits, pasta and noodles, the production of starch derived syrups, sorbitol, xylose and/or xylitol, the wheat gluten-starch separation industry, maize processing, the improvement of plant disease resistance, in nutraceutical or pharmaceutical applications such as maintaining the structure of dietary fiber material, and in the field of paper and pulp technologies.

The present invention also relates to polynucleotide sequences encoding inhibitors of cellulolytic, xylanolytic and/or β-glucanolytic enzymes (sometimes also referred to as cellulases (EC: 3.2.1.4), pentosanases and/or hemicellulases), especially inhibitors of pentosan degrading enzymes such as endoxylanase (such as EC: 3.2.1.8), β-xylosidase (such as EC: 3.2.1.37), and α-L-arabinofuranosidase (such as EC: 3.2.1.55), to inhibitors of cellulase (such as EC: 3.2.1.4), β-glucanase (such as EC: 3.2.1.73 or such as 3.2.1.6), and to inhibitors of other xylan, arabinoxylan and β-glucan degrading enzymes and to said inhibitors obtainable by a recombinant production process using said polynucleotide sequences encoding the recombinant inhibitors. The invention also relates to feed or food compositions comprising said recombinant inhibitors and the use of said recombinant inhibitors for screening enzymes such as endoxylanases that are totally, more, less or not inhibited by said inhibitors or for modifying enzymes, such as endoxylanases in such way that they are totally, more, less or not inhibited by said inhibitors, as well as to the use of said recombinant inhibitors in different areas of food, feed and/or beverage technologies, such as malting and brewing, the production of animal feedstuffs such as to increase their conversion, the production of refrigerated and/or frozen doughs, such as to reduce syruping, the production of baked and/or extruded cereal products such as straight dough, sponge and dough (all said dough compositions comprising flour and water) and Chorleywood breads, breakfast cereals, different types of biscuits, pasta and noodles, the production of starch derived syrups, sorbitol, xylose and/or xylitol, the wheat gluten-starch separation industry, maize processing, the improvement of plant disease resistance, in nutraceutical or pharmaceutical applications such as maintaining the structure of dietary fiber material, and in the field of paper and pulp technologies.

BACKGROUND OF THE INVENTION

Cereal grains contain three groups of important biopolymers: starch, proteins and non-starch polysaccharides. Starch and a large part of the protein fraction are located in the endosperm and serve as reserve material for the plant during germination and the initial stages of growth. They are degraded by amylases and proteases respectively [1]. The non-starch polysaccharides include mainly arabinoxylan (AX) and β-glucan which are part of the cell walls and are hydrolysed by xylanolytic and β-glucanolytic enzymes respectively [1, 2]. The degradation of these cell wall polysaccharides in the endosperm and aleurone layer during the germination improves the accessibility of starch and protein for amylases and proteases [3, 4]. Proteins that inhibit amylases [5–9] and proteases [10–13] have already been purified from cereals and have been characterised extensively. They possibly regulate the plant starch and nitrogen metabolism and/or play an important role in plant defence by inhibiting enzymic hydrolysis by micro-organisms and predators.

Recently, a new class of enzyme inhibitors, i.e. proteinaceous inhibitors of endo-β-1,4-xylanases (endoxylanases, EC: 3.2.1.8), has been discovered in cereals by Debyser and Delcour [14] and Debyser et al. [15]. Inhibition activity against such xylanolytic enzymes was found in different cereals such as wheat (*Triticum aestivum* L.), barley (*Hordeum vulgare* L.) and rye (*Secale cereale* L.) [14, 16]. An endoxylanase inhibitor, named TAXI (*T. aestivum* L. endoxylanase inhibitor), was purified from wheat flour and characterised by Debyser and Delcour [14] and Debyser et al. [17] wherein for the screening of the inhibition activity a single endoxylanase from *Aspergillus niger* was used. TAXI has a molecular mass of ca. 40.0 kDa and occurs in two molecular forms A and B, B presumably as a result of proteolytic modification of A [14, 16, 17]. As a result of reduction with β-mercaptoethanol, the modified molecular form B dissociates in two fragments with molecular masses of ca. 10.0 and 30.0 kDa respectively, whereas the molecular mass of the non-modified form does not change upon reduction. The inhibitor is heat sensitive and has a pI of ca. 8.8 [14, 16, 17]. Rouau and Surget [18] also found evidence for the presence of endoxylanase inhibitors in regular and durum wheats. These authors detected high inhibition activity against microbial endoxylanases in both wheat flour and bran. McLauchlan et al. [19] and Hessing and Happe [20] purified a wheat endoxylanase inhibitor structurally quite different from TAXI. In the isolation procedure [19], an endoxylanase, partially purified from a commercial *A. niger* hemicellulase preparation was used for the screening of the inhibition activity. The resulting inhibitor is monomeric, glycosylated and a heat sensitive protein. It has a pI of 8.7–8.9 [19] or higher than 9 [20], a molecular mass of 29.0 kDa [19] and 31.0 kDa [20] and was found to be a competitive inhibitor. The N-terminal amino acid sequence is 87% identical with a sequence close to the N-terminus of the rice chitinase III polypeptide chain and shows no homology with the amino acid sequences of TAXI [19,20].

Further information on TAXI can be found in Sibbesen and Sørensen [36].

SUMMARY OF THE INVENTION

The present invention concerns methods for the separation and/or isolation of inhibitors of cellulolytic, xylanolytic and/or β-glucanolytic enzymes, preferably inhibitors of endoxylanase, of β-glucanase, of β-xylosidase, of α-L-arabinofuranosidase, and of other xylan, arabinoxylan and β-glucan degrading enzymes preferably obtained from micro-organisms, plants, plant materials or fractions thereof (such as cereals, cereal grains, cereal germs or fractions thereof, cereal flours or fractions thereof) by the use of two or more enzymes, especially endoxylanases, during the screening for endoxylanase inhibiting activity and/or by the application of affinity chromatography with immobilised enzymes, especially endoxylanases.

The inhibitory effect towards xylan and/or arabinoxylan hydrolysing enzymes can be e.g. demonstrated by the endoxylanase method with AZCL arabinoxylan (cfr. infra). Likewise, the inhibitory effect towards β-glucan hydrolysing enzymes can be e.g. demonstrated by the β-glucanase method with AZCL β-glucan (cfr. infra).

The present invention also concerns novel inhibitors obtainable by said purification methods, of cellulolytic, xylanolytic and/or β-glucanolytic enzymes (sometimes also referred to as cellulases (EC:3.2.1.4), pentosanases and/or hemicellulases) especially inhibitors of pentosan degrading enzymes such as endoxylanase (such as EC: 3.2.1.8), β-xylosidase (such as EC: 3.2.1.37), and α-L-arabinofuranosidase (such as EC: 3.2.1.55), to inhibitors of cellulase (such as EC: 3.2.1.4), β-glucanase (such as EC: 3.2.1.73 or such as 3.2.1.6), and to inhibitors of other xylan, arabinoxylan and β-glucan degrading enzymes.

In this text, "An inhibitor of an enzyme" means a molecule which is able to inhibit partially or totally the activity of said enzyme. In irreversible inhibition, the inhibitor is covalently linked to the enzyme or bound so tightly that its dissociation from the enzyme is very slow. In contrast, reversible inhibition may be characterised by a rapid equilibrium between the enzyme and the inhibitor. A competitive inhibitor blocks the active site and in this way prevents the substrate/active site interaction. As a consequence, the reaction rate is diminished. In the case of competitive inhibition, the inhibitor in many cases mimicks the normal substrate of said enzyme. For this type of inhibition, the Dixon plots (inverse of reaction rate, 1/V, versus inhibitor concentration, [I]) corresponding to the different substrate concentrations and the Lineweaver-Burk plots (inverse of reaction rate, 1/V, versus inverse of substrate concentration, 1/[S]) corresponding to different inhibitor concentrations intersect in the left quadrant and the vertical axis respectively. For non-competitive inhibition, both inhibitor and arabinoxylan can bind to the enzyme and this independent of the binding order. The inhibition can in most cases be explained by a change in conformation of the enzyme at or near the active site with a decreased turnover number as a result. In the case of non-competitive inhibition, however, the Dixon and Lineweaver-Burk plots intersect on the horizontal axis in the left quadrant. Competitive inhibition can be distinguished from non-competitive inhibition by determining whether the inhibition can be overcome by raising the substrate concentration. Inhibitors isolated from a specific biological species and that are of proteinaceous or glycoproteinaceous nature can be active against enzymes of the same species (i.e. endogenous enzymes) and/or against enzymes of different species (i.e. exogenous enzymes).

Advantageously, the inhibitors of the invention can be produced by micro-organisms or may be present in various extraction media from micro-organisms or plant material, such as cereals or fractions thereof, such as cereal grains or fractions thereof, such as cereal germs or fractions thereof, such as cereal flours or fractions thereof, such as from wheat, durum wheat, rye, triticale, barley, sorghum, oats, maize and/or rice, from which they can be purified by the methods well known by the man skilled in the art. According to a preferred embodiment of the present invention, inhibitors are endoxylanase inhibitors which are typically water-soluble alkaline proteinaceous species, having a pI (i.e. –log of the isoelectric point) of greater than about 7.0. The endoxylanase inhibitor molecular weights as determined by SDS-page are typically 40–43 kDa. Following reduction with β-mercaptoethanol three SDS-page protein bands are found with SDS-page molecular weights of ca. 40–43 kDa, ca. 30 kDa, and ca. 10 kDa. The N-terminal sequences of the 40–43 kDa proteins or glycoproteins are typically as follows: SEQ ID No. 1 (TAXI I): Leu-Pro-Val-Leu-Ala-Pro-Val-Thr-Lys-Asp-Pro-Ala-Thr-Ser-Leu-Tyr-Thr-Ile-Pro-Phe-Xaa-Asp-Xaa-Ala, wherein the first Xaa being preferably Leu and wherein the second Xaa being preferably Leu; SEQ ID No. 2 (TAXI II): Lys-Gly-Leu-Pro-Val-Leu-Ala-Pro-Val-Thr-Lys-Asp-Thr-Ala-Thr-Ser-Leu-Tyr-Thr-Ile-Pro-Phe or SEQ ID No. 3 (HvXI): Lys-Ala-Leu-Pro-Val-Leu-Ala-Pro-Val-Thr-Lys-Asp-Ala-Ala-Thr-Ser-Leu-Tyr-Thr-Ile-Xaa-Xaa, wherein the first Xaa being preferably Pro and wherein the second Xaa being preferably Phe. The 30 kDa band has the above described typical N-terminal amino acid SEQ ID No. 1 or SEQ ID No. 2 or SEQ ID No. 3, while the N-terminal amino acid sequence of the 10 kDa band is typically as follows: SEQ ID No. 4 (TAXI I): Gly-Ala-Pro-Val-Ala-Arg-Ala-Val-Glu-Ala-Val-Ala-Pro-Phe-Gly-Val-Xaa-Tyr-Asp-Thr, wherein Xaa being preferably Leu; or SEQ ID No. 5 (TAXI II): Gly-Ala-Pro-Val-Ala-Arg-Ala-Val-Ile-Pro-Val-Ala-Pro-Phe-Glu-Leu-Xaa-Tyr-Xaa-Thr-Lys-Ser-Leu-Gly-Asn, wherein the first Xaa being preferably Leu and wherein the second Xaa being preferably Asp; or SEQ ID No. 6 (HvXI): Gly-Ala-Leu-Ala-Ala-Xaa-Gly-Val-Asn-Pro-Val-Ala-Pro-Phe-Gly-Xaa-Xaa-Tyr-Asp-Ala-Xaa-Thr-Xaa-Xaa, wherein the first Xaa is unknown, the second Xaa being preferably Leu, the third Xaa is unknown, the fourth Xaa is unknown, the fifth Xaa being preferably Asn, and wherein the sixth Xaa being preferably Gly.

Therefore, the present invention is also related to an inhibitor with a SDS-page molecular weight of typically 40–43 kDa being a protein or glycoprotein having a marker whose amino acid sequence has more than 70% homology, preferably more than 85% homology, more preferably is identical with SEQ ID No. 1. or SEQ ID No. 2 or SEQ ID No. 3

The present invention is furthermore also related to an inhibitor with a SDS-page molecular weight of typically 30 kDa being a protein or glycoprotein having a marker whose amino acid sequence has more than 70% homology, preferably more than 85% homology, more preferably is identical with SEQ ID No. 1. or SEQ ID No. 2 or SEQ ID No. 3.

The present invention is furthermore also related to an inhibitor with a SDS-page molecular weight of typically 10 kDa being a protein or glycoprotein having a marker whose amino acid sequence has more than 70% homology, preferably more than 85% homology, more preferably is identical with SEQ ID No. 4. or SEQ ID No. 5 or SEQ ID No. 6.

Advantageously, said markers are the end-terminal amino acid sequences of the protein or glycoprotein.

According to the invention, a marker of a protein or glycoprotein means a specific amino acid sequence (or its corresponding nucleotide sequence) that is able to distinguish one protein family from another protein family.

Another aspect of the invention involves the corresponding polynucleotide sequences of inhibitors of cellulolytic, xylanolytic and/or β-glucanolytic enzymes (sometimes also referred to as cellulases (EC: 3.2.1.4), pentosanases and/or hemicellulases) especially inhibitors of pentosan degrading enzymes such as endoxylanase (such as EC: 3.2.1.8), β-xylosidase (such as EC: 3.2.1.37), and α-L-arabinofuranosidase (such as EC: 3.2.1.55), to inhibitors of cellulase (such as EC: 3.2.1.4), β-glucanase (such as EC: 3.2.1.73 or such as 3.2.1.6), and to inhibitors of other xylan, arabinoxylan and β-glucan degrading enzymes.

The invention concerns isolated polynucleotides that encode for endoxylanase inhibitors from wheat, rye, rice, maize, oat and barley.

The invention also relates to amino acid sequences of endoxylanase inhibitors from wheat comprising the complement of SEQ ID No. 7, SEQ ID No. 8, SEQ ID No. 9, SEQ ID No. 19, SEQ ID No. 20, SEQ ID No. 21, SEQ ID No. 22 or variants thereof. In addition, the invention features polynucleotide sequences which hybridize under stringent conditions with SEQ ID No. 10, SEQ ID No. 15, SEQ ID No. 16, SEQ ID No. 17, SEQ ID No. 18 and SEQ ID No. 39.

The invention also relates to amino acid sequences of an endoxylanase inhibitor from barley comprising the complement of SEQ ID No. 11, SEQ ID No. 12, SEQ ID No. 13 or variants thereof. In addition, the invention features polynucleotide sequences which hybridize under stringent conditions with SEQ ID No. 14.

The invention also relates to amino acid sequences of endoxylanase inhibitors from rye, rice, maize and oat comprising the complement of SEQ ID No. 25, SEQ ID No. 26, SEQ ID No. 28, SEQ ID No. 30, SEQ ID No. 41, SEQ ID No. 43 or variants thereof. In addition, the invention features polynucleotide sequences which hybridize under stringent conditions with SEQ ID No. 23, SEQ ID No. 24, SEQ ID No. 27, SEQ ID No. 29, SEQ ID No. 40 and SEQ ID No. 42.

Thus the invention additionally features nucleic acid sequences encoding polypeptides, oligonucleotides, peptide nucleic acids (PNA), fragments, portions or antisense molecules thereof, and expression vectors and host cells comprising polynucleotides that encode endoxylanase inhibitors such as TAXI I.

The invention also relates to a method for obtaining said inhibitors from a micro-organism, such as a genetically modified micro-organism which expresses said inhibitors, from a plant, or from a plant material (such as cereals, cereal grains, cereal germs or fractions thereof, cereal flours or fractions thereof, by subjecting said plant, said plant material and/or said micro-organism to one or more extraction and/or fractionation steps).

Another aspect of the present invention is related to a method for genetically transforming a micro-organism, a plant or a plant material in order to obtain the expression of the inhibitors according to the invention wherein the micro-organism, the plant or plant material is genetically modified by the introduction of a genetic material encoding said inhibitors into the micro-organism, the plant or plant material and obtain their translation and expression by genetic engineering methods well known by the man skilled in the art.

The invention furthermore relates to processes aiming at changing, preferably reducing or increasing levels of said inhibitors in a micro-organism, a plant or a plant material, by reducing or increasing the expression of said inhibitors, by the methods well known by the man skilled in the art and/or by using molecules which are able to block the inhibitor activity or activate said inhibitor.

The invention furthermore relates to use of said inhibitors for screening enzymes, such as endoxylanases that are totally, more, less or not inhibited by said inhihibitors or for modifying these enzymes, such as endoxylanases, by the methods well known by the man skilled in the art, in such way that they are totally, more, less or not inhibited by said inhibitors.

The invention furthermore relates to the obtained inhibitors, micro-organisms, plants, plant materials, and/or fractions thereof and to their use in different areas of food, feed and/or beverage technologies, such as improving malting and brewing, improving animal feedstuffs efficiency, baked and/or extruded cereal products (such as straight dough, sponge and dough and Chorleywood breads, breakfast cereals, different types of biscuits, pasta and noodles), improving the production of refrigerated and/or frozen doughs, such as to reduce syruping, (all said dough compositions comprising water and flour), improving the production of starch derived syrups, sorbitol, xylose and/or xylitol, improving wheat gluten-starch separation and production, maize processing, improving plant disease resistance, improving nutraceutical or pharmaceutical applications (such as maintaining the structure of dietary fiber material), and improving paper and pulp technologies.

The present invention will be described in details in the following description of a preferred embodiment without limiting the scope of the present invention.

BRIEF DESCRIPTION OF THE DRAWINGS

FIG. 21 shows the nucleotide and amino acid sequences of the PCR product.

FIG. 22 shows the insertion of the PCR product in the pBAD/Thio-TOPO vector.

FIG. 23A represents the recombinant thioredoxin-TAXI fusion protein.

FIG. 23B shows the recombinant TAXI protein as expressed by the pHOS31-TAXI plasmid.

FIG. 23C shows the recombinant MBP-TAXI protein as expressed by the pMAL-p2X-TAXI plasmid.

FIG. 25 shows the insertion of the BgIII cut PCR product in the Bg1II restriction site of respectively the pHOS31 vector. The C-terminal amino acids of the pelB leader sequence together with the 'linker' amino acids are also represented.

FIG. 26 shows the insertion of the Bg1II cut PCR product in the BamHI restriction site of the pMAL-p2X vector. The C-terminal amino acids of the malE signal sequence together with the 'linker' amino acids are also represented.

DETAILED DESCRIPTION OF THE INVENTION

Figure 1:
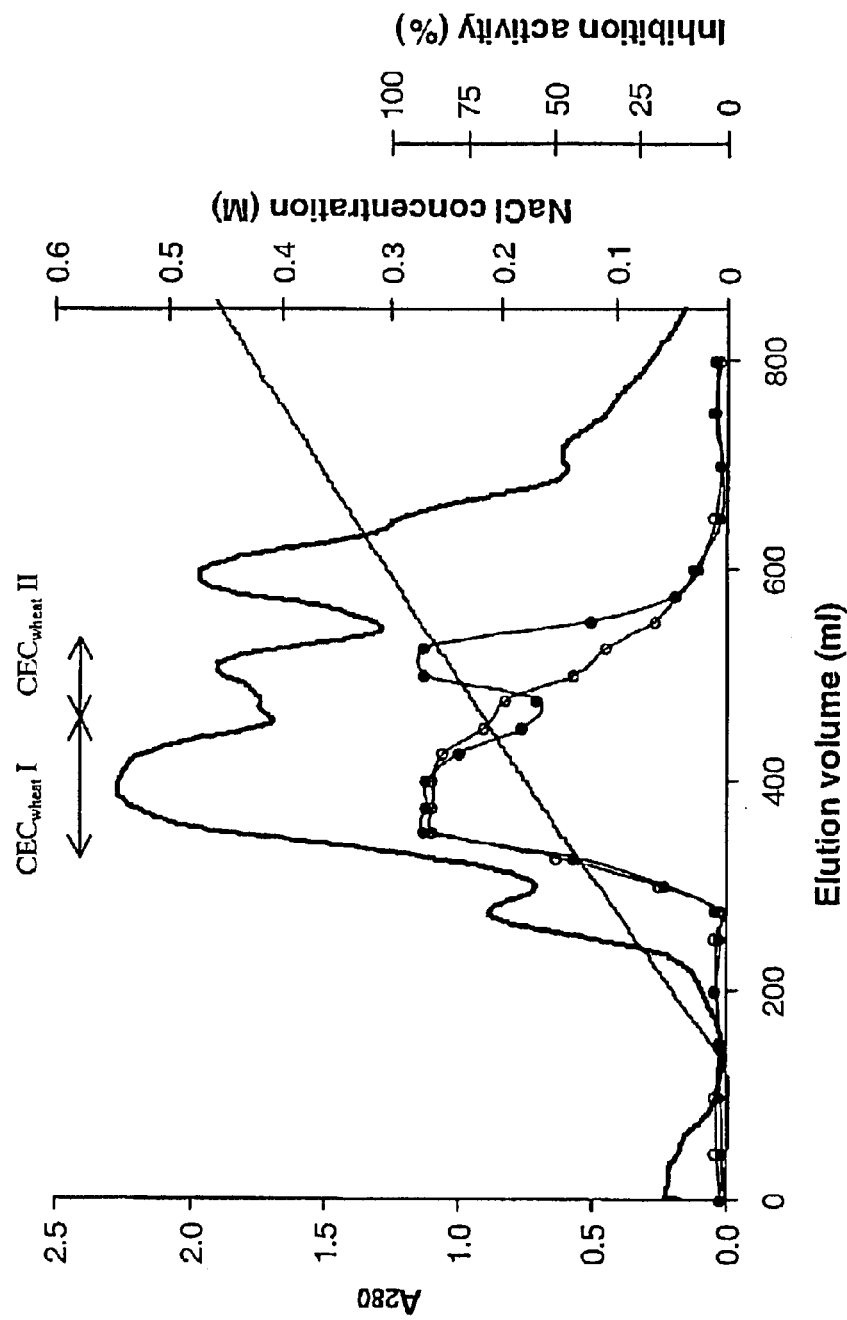
FIG. 1 shows the SP Sepharose® Fast Flow chromatogram (—) of $CEC_{wheat-}$ material, with indication of the NaCl-gradient (—) and the inhibition activities against *B. subtilis* (•) and *A. niger* (○) endoxylanases.

The inventors unexpectedly found that, using an endoxylanase, such as the *Bacillus subtilis* endoxylanase, on top of the previously described *A. niger* endoxylanase for screening the inhibition activity during the isolation process of TAXI [14], the endoxylanase inhibitor (TAXI), as described by Debyser and Delcour [14] and Debyser et al.

[17], is in fact a mixture of at least two endoxylanase inhibitors, i.e. TAXI I and TAXI II. Both inhibitors unexpectedly were shown to have comparable molecular masses and structures but they clearly differ from one another in pI and endoxylanase specificity. In this way, a combination of two or more endoxylanases may be used for the isolation of endoxylanase inhibitors with a varying selectivity towards endoxylanases. It follows that the use of more endoxylanases can facilitate the identification and/or purification of inhibitors in mixtures of endoxylanase inhibitors.

The present invention for the first time shows that, on the one hand, wheat contains at least two types of TAXI-like endoxylanase inhibitors that differ in their endoxylanase specificity and that, on the other hand, at least one such inhibitor occurs in barley.

We unexpectedly found that, depending on the endoxylanase used for studying the type of inhibition, either a competitive or a non-competitive type of inhibition can be observed.

Furthermore, we describe for the first time a method for the purification of endoxylanase inhibitors, comprising of an affinity chromatographic step with immobilised endoxylanases.

We also document for the first time a new technique for the purification of endoxylanases from commercially available enzyme preparations based on affinity chromatography with an immobilised cocktail of 'TAXI'-like endoxylanase-inhibitors.

DNA sequences coding for endoxylanase inhibitors or part thereof are determined. For the first time, a recombinant active endoxylanase inhibitor from wheat was produced by a micro-organism.

Definitions

The term "nucleotide sequence" in relation to the present invention includes genomic DNA, cDNA, recombinant DNA (e.g. DNA prepared by use of recombinant DNA techniques), synthetic DNA, and RNA, as well as combinations thereof. Preferably, the term "nucleotide sequence" means DNA. The nucleotide sequences of the present invention may be single or double stranded. The nucleotide sequences of the present invention may include within them synthetic or modified nucleotides. A number of different types of modifications to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out to enhance the in vivo activity or life span of nucleotide sequences of the present invention.

The terms "variant" or "homologue" with respect to the nucleotide sequence of the present invention and the amino acid sequence of the present invention are synonymous with allelic variations of the sequences.

In particular, the term "homology" as used herein may be equated with the term "identity".

Furthermore, the terminology used herein is for the purpose of describing particular embodiments only, and is not intended to limit the scope of present invention, which will be limited only by the appending claims.

EXAMPLES

In what follows, the purification and partial characterisation of two endoxylanase inhibitors from wheat(*Triticum aestivum* L., var. Soissons), TAXI I and TAXI II (Example 1), and one endoxylanase inhibitor from barley (*Hordeum vulgare* L., var. Hiro), HvXI (Example 2), will be examined. In this context, an approach to isolate the inhibitors using cation exchange and gel filtration chromatography as the main techniques will be described. Furthermore, the isolation of ('TAXI'-like) endoxylanase inhibitors from a commercial wheat flour (likely a mixture of different wheat varieties), rye flour and barley whole meal using an alternative approach, i.e. affinity chromatography with immobilised endoxylanase will be discussed (Example 3). Furthermore, a new method based on affinity chromatography with immobilised 'TAXI'-like endoxylanase inhibitors to isolate endoxylanases from commercially available enzyme preparations will be examplified (example 4). We also describe corresponding DNA sequences (Examples 5,6,7,8,9 and 10) and recombinant expression of endoxylanase inhibitors (Example 11).

General Experimental Methods for Examples 1 and 2

Materials

All reagents were purchased from Sigma-Aldrich (Bornem, Belgium) and were of analytical grade, unless specified otherwise.

Endoxylanase (EC: 3.2.1.8) M1 from *Trichoderma viride* (family 11), endoxylanase M4 and α-L-arabinofuranosidase (arabinofuranosidase, EC: 3.2.1.55) from *Aspergillus niger* (family 11), endoxylanase M6 from a rumen microorganism culture filtrate, azurine-crosslinked wheat AX tablets (AZCL-AX) and soluble wheat AX (medium viscosity) were from Megazyme (Bray, Ireland). Endoxylanases from *Bacillus subtilis* (family 11) and *Aspergillus aculeatus* (family 10) were from NV Puratos (Groot-Bijgaarden, Belgium). A β-D-xylosidase (xylosidase, EC 3.2.1.37) from *A. niger* and bovine serum albumin (BSA) were purchased from Sigma-Aldrich (Bornem, Belgium). The digoxigenin (DIG) glycan detection kit® was from Boehringer (Mannheim, Germany).

All electrophoresis media and markers, chromatographic media and nitrocellulose blot membranes were from Pharmacia Biotech (Uppsala, Sweden).

Wheat (*Triticum aestivum* L., var. Soissons) and barley (*Hordeum vulgare* L., var. Hiro), were from AVEVE (Landen, Belgium) and were milled with a Bühler MLU-202 mill (Uzwil, Switzerland) and a Cyclotec 1093 sample mill (Tecator, Hoganäs, Sweden) respectively.

Protein Determination

Protein concentrations were determined according to the Coomassie Brilliant Blue method of Bradford [21] with BSA as a standard.

Endoxylanase Inhibition Assay Procedure

The inhibition activities of a set of samples were determined with the Xylazyme-AX method as described by Debyser [16]. Solutions of the *T. viride*, the *A. niger*, the *A. aculeatus* and the *B. subtilis* endoxylanases were prepared in sodium acetate buffer (25.0 mM, pH 5.0) with BSA (0.5 mg/ml) whereas the solution of the rumen microorganism culture filtrate was prepared in sodium phosphate buffer (25 mM, pH 6.0) with BSA (0.5 mg/ml). All endoxylanase solutions contained 2.0 enzyme units per 1.0 ml. One enzyme unit corresponds to an increase in extinction at 590 nm, using the xylazyme-AX method (cfr. infra), of 1.0.

Endoxylanase solution (0.5 ml) was preincubated for 30 min at room temperature with an equal amount of sample (same buffer as enzyme solution), possibly containing inhibition activity. The mixtures were kept at 30° C. and after 10 min an AZCL-AX tablet was added. Next, they were incubated for 60 min at 30° C. The reaction was terminated by adding 1.0% (w/v) tris-hydroxymethylaminomethane (Tris) solution (10.0 ml) and vigorous vortex stirring. After 10 min at room temperature, the tubes were shaken vigorously and the contents filtered through a Schleicher & Schuell filter (φ 90 mm) (Dassel, Germany). The absorbances at 590 nm ($A_{590}$) were measured against a control, prepared by incubating the sample with buffer instead of enzyme solution, with an Ultraspec III® UV/Visible Spectrophotometer (Pharmacia Biotech, Uppsala, Sweden). The difference between the absorbance values of samples and another control, prepared by using buffer instead of sample, is a measure for the inhibition activity, expressed as percent reduction of endoxylanase activity.

Arabinofuranosidase and Xylosidase Inhibition Assay Procedure

The method used was based on that by Cleemput et al. [22]. p-Nitrophenyl arabinose and p-nitrophenyl xylose were used as substrates for measuring the α-L-arabinofuranosidase and β-D-xylosidase activities respectively, in the presence or absence of inhibitor. Substrate (0.05 mmol), arabinofuranosidase (50 µl), xylosidase (1.0 ml), TAXI I (234 µg), TAXI II (580 µg) and HVXI (460 µg) were separately dissolved in Mes buffer (50 mM, pH 5.5; 5 ml). Enzyme (25 µl) and endoxylanase inhibitor (25 µl) solutions were preincubated for 30 min at room temperature. Substrate (100 µl) was added and after 30 min at 30° C. the reaction was terminated by adding 1.0% (w/v) Tris solution (1.5 ml). Finally, the absorbance at 410 nm ($A_{410}$) was measured against a control.

Protein Electrophoresis

SDS-PAGE under non-reducing and reducing conditions was performed on 20% polyacrylamide gels with a Phast-System® unit (Pharmacia Biotech, Uppsala, Sweden), according to the method of Laemmli [23]. β-Mercaptoethanol [5% (v/v)] was used as reducing agent. Low molecular weight (LMW) markers were α-lactalbumin (14.0 kDa); trypsin inhibitor (20.1 kDa); carbonic anhydrase (30.0 kDa); ovalbumin (43.0 kDa); albumin (67.0 kDa); phosphorylase b (94.0 kDa). The pI of the inhibitor was determined with the same instrument using polyacrylamide gels containing ampholytes (pH 3–9) and appropriate standards (Pharmacia Biotech calibration kit, pI 3.5–9.3). All gels were silver stained according to the instructions of the manufacturer (Pharmacia Biotech, Development Technique file N° 210).

Protein Sequencing

TAXI I (25 µg), TAXI II (25 µg) and HVXI (25 µg) were sub-mitted to SDS-PAGE under reducing conditions (Laemmli, 1970) [23] in a SE 600 Series gel electrophoresis unit (Hoefer Pharmacia Biotech Inc., San Francisco, Calif.). The slab gel (140.0×160.0×1.5 mm) consisted of a stacking gel [3.88% (w/v) T 1.33% (w/v) C] and a running gel [17.57% (w/v) T, 0.46% (w/v) C]. Separation was achieved by using a current of 30 mA for 4 h at room temperature. The proteins were electroblotted onto a nitrocellulose membrane with the Trans-Blot® Semi-Dry Electroforetic Transfer Cell (Bio-Rad, Nazareth, Belgium), using an electric potential difference of 10 V for 1 h at room temperature, and were subjected to Edman degradation. The N-terminal amino acid sequences were determined with an Application Biosystems 477 A Protein Sequencer, connected on line with a 120 A phenylthiohydantoin-amino-acid analyser (Perkin Elmer, Lennik, Belgium).

Glycan Detection

For glycan detection, the digoxigenin (DIG) glycan assay was carried out as described by Roels and Delcour [24]. TAXI I (1.0 mg/ml), TAXI II (1.0 mg/ml), HVXI (1.0 mg/ml), the positive control protein transferrin (1.0 mg/ml) and the negative control protein creatinase (1.0 mg/ml) were separated by SDS-PAGE under reducing conditions as described above, but using the sample buffer advised by the supplier of the DIG glycan detection kite. The proteins were electroblotted onto a nitrocellulose membrane with a semi-dry PhastTransfero unit (Pharmacia Biotech, Uppsala, Sweden), using an electric potential difference of 20 V for 30 min at 15° C. On the blot, the vicinal diols of the glycans were converted to aldehydes with metaperiodate and labelled with the steroid hapten DIG via hydrazide. The labelled glycoconjugates were detected with a digoxigenin specific antibody conjugated to alkaline phosphatase. In the presence of the appropriate substrate, blue-purple bands appeared where the phosphatase was present. Oxidation, labelling and detection were performed according to the kit instructions (Method B).

Partial Purification of Wheat and Barley Endoxylanase Inhibitors

The extraction of wheat flour and barley whole meal, the initial concentration and partial purification steps of the wheat and barley endoxylanase inhibitors were as described by Debyser and Delcour [14] and Debyser et al. [17].

Step I. Preparation of Wheat Flour or Barley Whole Meal Extracts

Wheat flour (10.0 kg) or barley whole meal (10.0 kg) were suspended in 0.1% (w/v) ascorbic acid (50.0 l), extracted over-night at 7° C. and centrifuged (10,000 g; 30 min; 7° C.). To the supernatants, 2.0 g/l $CaCl_2$ was added and the pH's were raised to 8.5 with 2.0 N NaOH to precipitate the pectins. The extracts were left overnight (7° C.) and centrifuged (10,000 g, 30 min, 7° C.). The pH's were adjusted to 5.0 with 2.0 M HCl.

Step II. Concentration and Partial Purification By Cation Exchange Chromatography (CEC)

At pH 5.0, proteins with endoxylanase inhibiting activity from the wheat flour and barley whole meal extracts were retained by CEC on a SP Sepharose® Fast Flow column (90×90 mm). In both cases, the column was equilibrated with sodium acetate buffer (25 mM, pH 5.0; 500.0 ml) and a protein fraction was eluted with 0.5 M NaCl (1.0 l). The eluates were dialysed against deionised water (7° C., 48 h) and lyophilised (=$CEC_{wheat}$ material, 17.0 g and $CEC_{barley}$ material, 10.8 g).

Example 1

Isolation and Characterization of Two Xylanase Inhibitors from Wheat (TAXI I and TAXI II)

Further Purification of Wheat Endoxylanase Inhibitors

The wheat endoxylanase inhibitors, TAXI I and TAXI II, were further purified based on the method of Debyser and Delcour [14] and Debyser et al. [17]. After each purification step, the resulting fractions were assayed for endoxylanase inhibition activity with A. niger and B. subtilis endoxylanases and the purity was checked using SDS-PAGE.

Step 1. Purification By CEC

Batches of $CEC_{wheat}$ material (4.0 g) in sodium acetate buffer (25 mM, pH 5.0; 400.0 ml) were applied on a SP Sepharose® Fast Flow column (26×300 mm), equilibrated with sodium acetate buffer (25 mM, pH 5.0; 200.0 ml). The proteins were eluted with a linear gradient of 0.0 to 0.5 M NaCl in 800.0 ml and a flow of 1.0 ml/min. Two separate fractions, one with high inhibition activity against B. subtilis and A. niger endoxylanases and one with high activity against B. subtilis endoxylanase but low activity against A. niger endoxylanase, were dialysed against deionized water (7° C., 48 h) and lyophilised (=$CEC_{wheat}$ I, 4.7 g, and $CEC_{wheat}$ II, 2.9 g, respectively).

Step 2. Purification By Gel Permeation Chromatography (GPC)

Batches of $CEC_{wheat}$ I (20 mg) and $CEC_{wheat}$ II (20 mg) in sodium acetate buffer (25 mM, pH 5.0; 1.0 ml) were fractionated by GPC on a Hiprep® Sephacryl® S-100 column (26×670 mm) with the same buffer (400 ml) and a flow of 0.7 ml/min. The active fractions were pooled (=$GPC_{wheat}$ I, 590 mg in 2500 ml, and $GPC_{wheat}$ II, 320 mg in 1630 ml, respectively).

Step 3. Purification By CEC $GPC_{wheat}$ I and $GPC_{wheat}$ II were diluted three times. Batches of the diluted $GPC_{wheat}$ I (100.0 ml) and diluted $GPC_{wheat}$ II (100.0 ml) were fractionated by CEC on a MonoS® HR 5/5 column (5×50 mm), equilibrated with sodium acetate buffer (25 mM, pH 4.0; 5.0 ml) and sodium phosphate buffer (20 mM, pH 6.5; 5.0 ml) respectively. The bound proteins were eluted with a linear gradient of 0.0 to 0.6 M NaCl in 60.0 ml and a flow of 1.0 ml/min. The fraction, as a result of fractionation of $GPC_{wheat}$ I and containing inhibition activity against B. subtilis and A. niger endoxylanases, and the fraction, which resulted from fractionation of $GPC_{wheat}$ II and had activity against B. subtilis endoxylanase but not against A. niger endoxylanase, were used for further purification of TAXI I and TAXI II respectively. They were diluted three times, acidified to pH 4.0 with 1.0 N acetic acid and chromatographed again on the same MonoS® column, equilibrated with sodium acetate buffer (25 mM, pH 4.0). The same flow and salt gradient were used. We finally obtained 12.0 mg TAXI I and 9.5 mg of TAXI II.

Inhibition Type Determination

For TAXI I, the inhibition kinetics was studied with the A. niger (Megazyme, Bray, Ireland) and the B. subtilis (Puratos, Groot-Bijgaarden, Belgium) endoxylanase and for TAXI II only with the B. subtilis endoxylanase, because of its lack of inhibition activity against the A. niger endoxylanase, as discussed earlier. In all cases, soluble wheat arabinoxylan was used as a substrate. For each of the inhibitor/enzyme combinations the reaction rates for different substrate and inhibitor concentrations were measured. They resulted in the corresponding Dixon and Lineweaver-Burk plots.

For determining the reaction rates, a modified Somogyi reducing sugar assay was used [25]. For this method, the following reagents were prepared: reagent A (25.0 g anhydrous sodium carbonate, 25.0 g sodium potassium tartrate and 200.0 g anhydrous sodium sulphate in 1.0 l demineralised water), reagent B (30.0 g copper sulphate pentahydrate and 4 drops concentrated sulphuric acid in 200.0 ml demineralised water), reagent C (50.0 g ammonium molybdate dissolved in 900 ml demineralised water, 42.0 ml concentrated sulphuric acid and 6.0 g sodium arsenate heptahydrate dissolved separately in 50.0 ml demineralised water were mixed and the total volume was adjusted to 1.0 l), reagent D (1.0 ml of reagent B and 25.0 ml reagent A) and reagent E (one part reagent C and four parts demineralised water).

Wheat arabinoxylan (50.0, 33.3, 25.0, 20.0, 16.6, 14.2, 12.5 and 11.1 mg) was dissolved in sodium acetate buffer (100 mM, pH 5.0; 10.0 ml). The endoxylanase and endoxylanase inhibitor solutions were prepared in the same buffer containing BSA (0.5 mg/ml). The latter solutions contained 0.0 to 11.0 µg/ml TAXI I or TAXI II. The endoxylanases were diluted to such an extent that in the above described Somogyi reducing sugar assay, carried out with 0.5% (w/w) soluble wheat AX and in absence of endoxylanase inhibitor, an increase in extinction comparable to that of the standard curve solution with the highest xylose concentration was obtained (cfr. infra).

Wheat arabinoxylan solution (0.5 ml) was mixed with 0.1 ml sodium acetate buffer (100 mM, pH 5.0) containing BSA (0.5 mg/ml) or with 0.1 ml endoxylanase inhibitor solution and incubated at 30° C. After 10 min endoxylanase (0.1 ml), equilibrated at the same temperature, was added. The reaction was terminated 15 min later by adding reagent D (0.5 ml), after which all tubes were boiled for 20 min. The samples were cooled at room temperature and mixed with reagent E (3.0 ml) for colour development. After 15 min the absorbance was measured at 520 nm against a reagent blank. For the latter, sodium acetate buffer (100 mM, pH 5.0) with BSA (0.5 mg/ml) was used instead of endoxylanase and endoxylanase inhibitor. To assess the reaction rates, a xylose standard curve was prepared by replacing endoxylanase and endoxylanase inhibitor with xylose solutions prepared in the same buffer (0–250.0 µg/ml).

Results

Inhibitor Purification

Using the purification method described above, and A. niger and B. subtilis endoxylanases for assaying inhibition activity, TAXI I and TAXI II were purified to homogeneity from wheat flour. After initial fractionation by cation exchange chromatography (CEC) on SP Sepharose® Fast Flow columns, two protein fractions, one with high inhibition activity against B. subtilis and A. niger endoxylanases ($CEC_{wheat}$ I) and one with high activity against B. subtilis endoxylanase but much lower activity against A. niger endoxylanase ($CEC_{wheat}$ II), were obtained, indicating specificity of different inhibitors present. FIG. 1 shows the SP Sepharose® Fast Flow chromatogram (—) of $CEC_{wheat}$-material, with indication of the NaCl-gradient (—) and the inhibition activities against B. subtilis (•) and A. niger (o) endoxylanases. $CEC_{wheat}$ I and $CEC_{wheat}$ II eluted at NaCl concentrations of 0.12 to 0.22 M and 0.23 to 0.27 M respectively. Both $CEC_{wheat}$ I and $CEC_{wheat}$ II contained no significant inhibition activity against A. aculeatus endoxylanase. The ratio of inhibition activity against B. subtilis endoxylanase to inhibition activity against A. niger endoxylanase ($IA^{B.s.}/IA^{A.n.}$) for diluted (×100) $CEC_{wheat}$ I and $CEC_{wheat}$ II was 1.11 and 3.21 respectively. This difference in $IA^{B.s.}/IA^{A.n.}$ indicated that we were dealing with mixtures of two endoxylanase inhibitors, further referred to as TAXI I and TAXI II.

Figure 2:
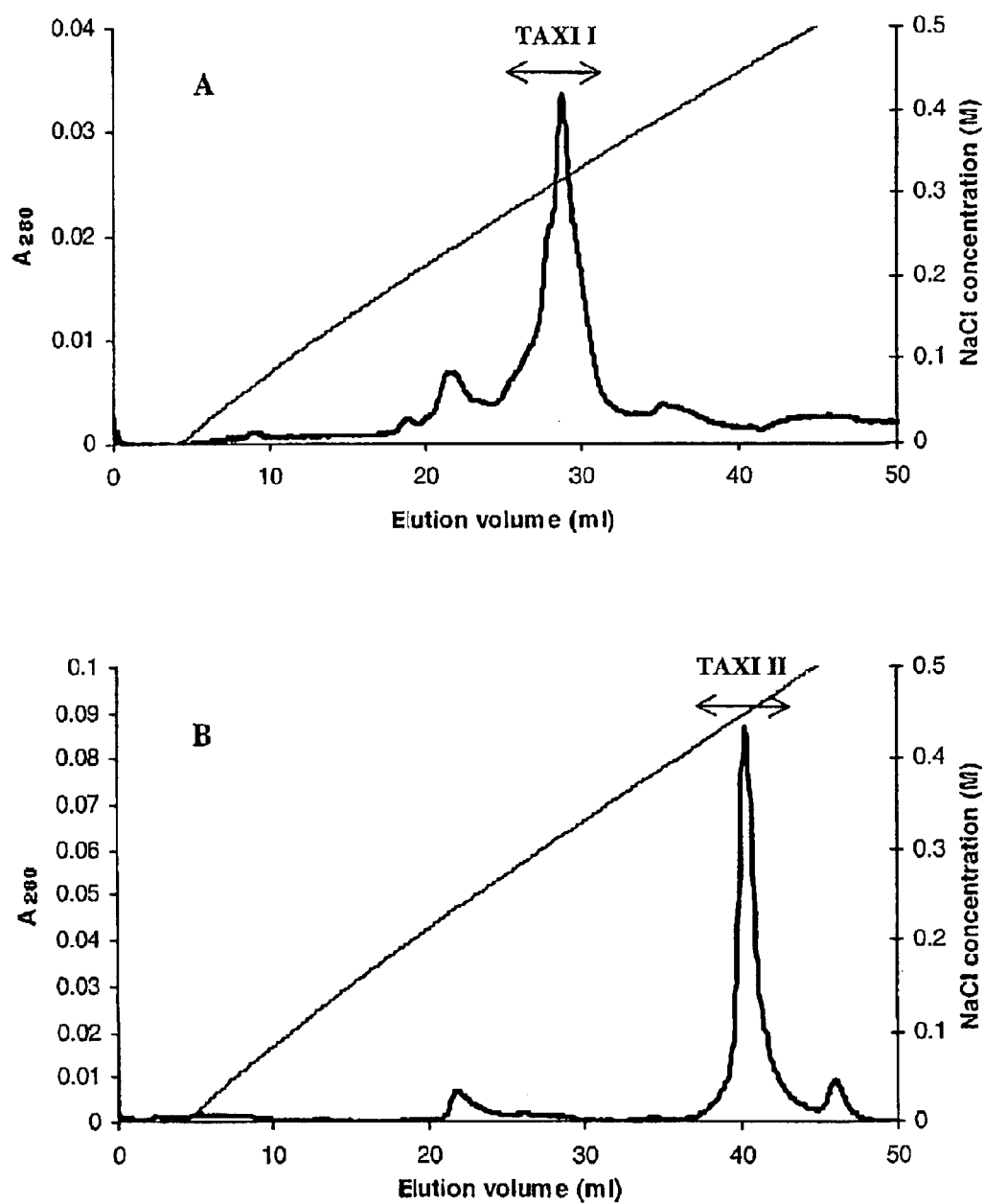
FIG. 2A displays the chromatogram (—) of the final separation of TAXI I on MonoS® with indication of the NaCl-gradient (—).
FIG. 2B displays the MonoS® CEC chromatogram (—) of almost pure TAXI II, separated at pH 4.0, with indication of the NaCl-gradient (—).

From $CEC_{wheat}$ I, TAXI I was purified by gel permeation chromatography (GPC) on a Hiprep® Sephacryl® S-100 column, at which it eluted at a volume of 127.5 to 138.5 ml ($GPC_{Wheat}$ I), followed by CEC on a MonoS® column at pH 4.0, at which it eluted at NaCl concentrations of 0.27 to 0.36 M. $GPC_{wheat}$ I contained also TAXI II but at much lower levels than TAXI I. With CEC on MonoS®, TAXI II, characterised by a much higher $IA^{B.s.}/IA^{A.n.}$ than TAXI I (cfr. infra), resulted in an additional but smaller inhibition activity peak in the chromatogram. The final purification step was performed twice at the same pH in order to increase the purity of TAXI I. FIG. 2A displays the chromatogram (—) of the final separation of TAXI I on MonoS® with indication of the NaCl-gradient (—).

TAXI II was isolated from $CEC_{wheat}$ II in a similar way, but CEC on MonoS® was performed first at pH 6.5 and secondly at pH 4.0. $CEC_{wheat}$ II contained, in contrast to $CEC_{wheat}$ I, much more TAXI II than TAXI I. With GPC, TAXI II eluted at the same volume as TAXI I ($GPC_{wheat}$ II) and with CEC on MonoS® at pH 6.5 and 4.0, TAXI II eluted at NaCl concentrations of 0.08 to 0.11 M and 0.42 to 0.49 M respectively. In analogy with the above, a small additional activity peak, caused by the presence of TAXI I, was observed with CEC on MonoSo at pH 6.5. FIG. 2B displays the MonoS® CEC chromatogram (—) of almost pure TAXI II, separated at pH 4.0, with indication of the NaCl-gradient (—).

Inhibitor Partial Molecular Characterisation

Figure 3:
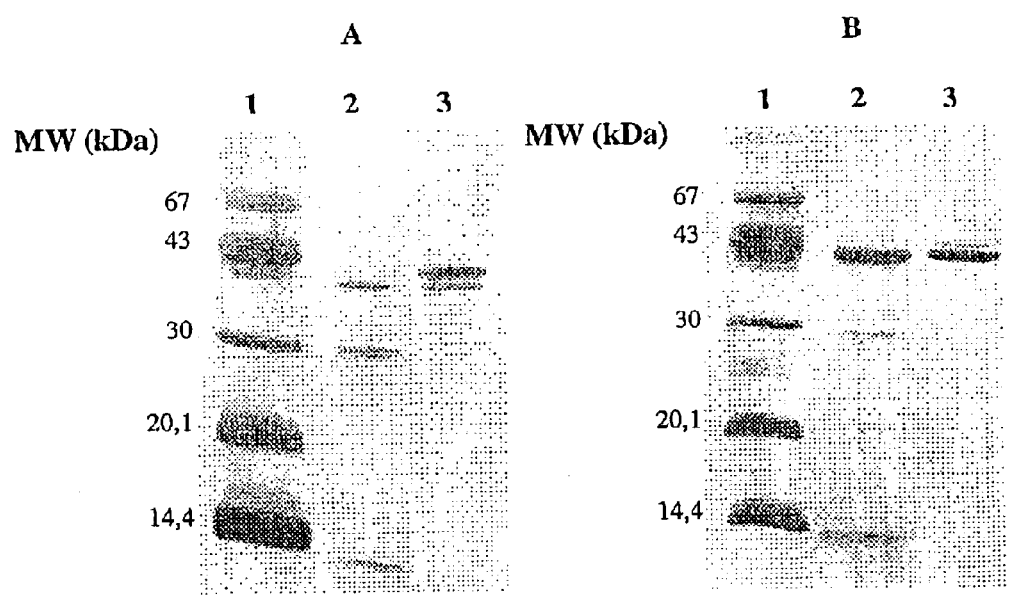
FIG. 3 shows the SDS-PAGE profiles of TAXI I (A) and TAXI II (B) with in lane 1 the low molecular mass markers (the size of the markers indicated on the left), in lane 2 pure inhibitor under reducing conditions and in lane 3 pure inhibitor under non-reducing conditions. The profiles (non-reducing conditions) of purified TAXI I and TAXI II show two polypeptides of ca. 40.0 kDa.

FIG. 3 shows the SDS-PAGE profiles of TAXI I (A) and TAXI II (B) with in lane 1 the low molecular mass markers (the size of the markers indicated on the left), in lane 2 pure inhibitor under reducing conditions and in lane 3 pure inhibitor under non-reducing conditions. The profiles (non-reducing conditions) of purified TAXI I and TAXI II show two polypeptides of ca. 40.0 kDa. Under reducing conditions, additional 30.0 and 10.0 kDa polypeptides can be seen. These findings are in agreement with those of Debyser and Delcour [14] and Debyser et al. [17]. The pI of TAXI II is at least ca. 9.3 and is therefore higher than that of TAXI I, which has a pI of ca. 8.8.

The 30.0 and 40.0 kDa polypeptides have the same N-terminal amino acid sequences, which for TAXI I and TAXI II are : SEQ ID No. 1 and SEQ ID No. 2 respectively. The N-terminal amino acid sequences of the TAXI I and TAXI II 10.0 kDa polypeptides are SEQ ID No. 4 and SEQ ID No. 5 respectively. These data confirm the molecular structure model of TAXI by Debyser and Delcour [14] and Debyser et al. [17]. Since the N-terminal sequences of the 30.0 and 40.0 kDa polypeptides are identical, the 10.0 and 30.0 kDa polypeptides, held together by one or more disulfide bonds, are probably derived from the 40.0 kDa polypeptide by proteolytic modification.

TAXI I and TAXI II are not glycosylated, as evidenced from the DIG glycan detection kit® results. Even after 15 h of colour development, no bands appeared on the blot for both inhibitors. The positive and negative control proteins, transferrin and creatinase respectively, gave the expected results.

Inhibition Activities Against Xylanolytic Enzymes

Figure 4:
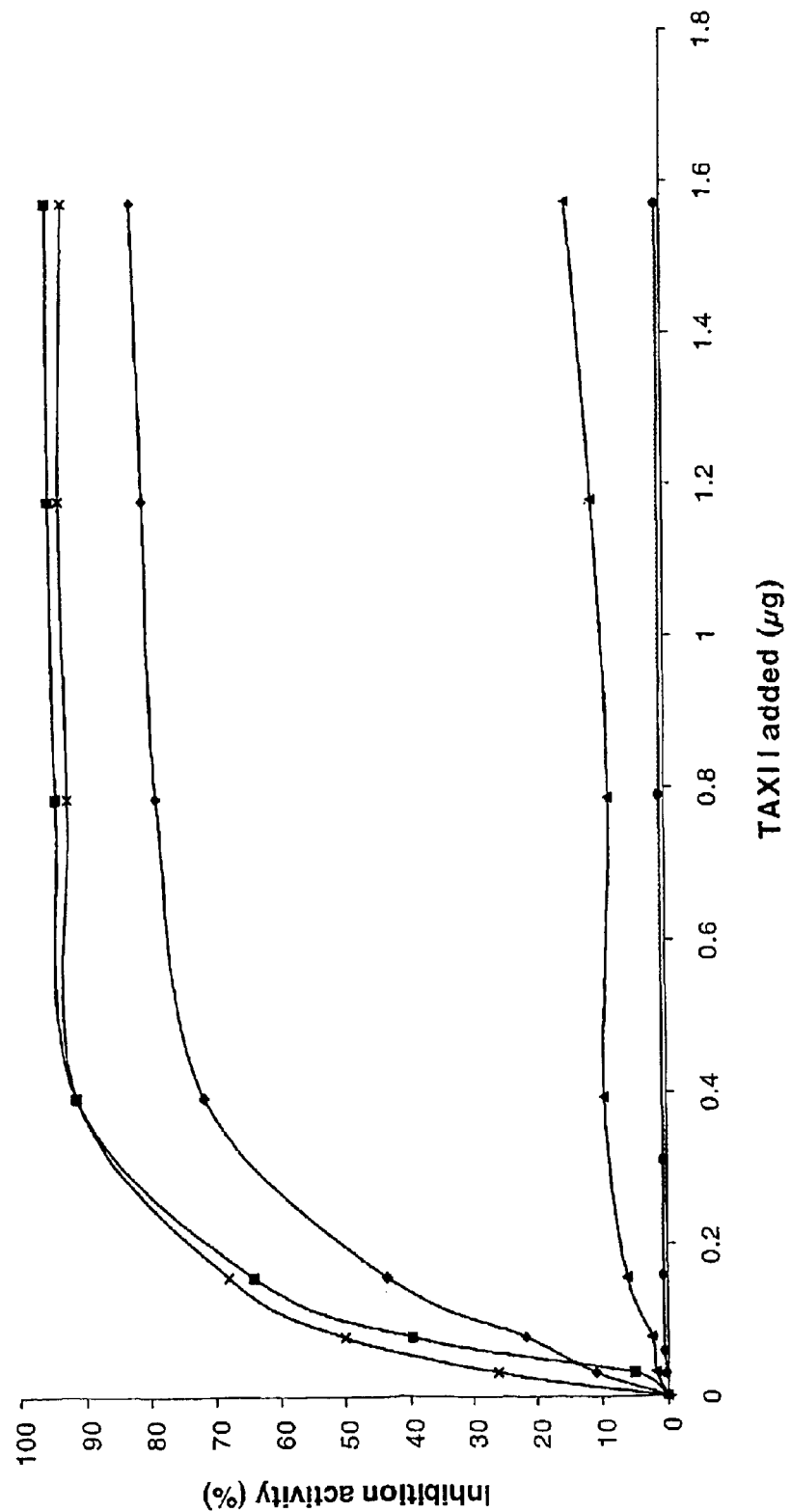
FIG. 4 shows the activities of different levels of TAXI I against five different endoxylanases, i.e. *A. aculeatus* (●), *A. niger* (■), *B. subtilis* (♦), *T. viride* (x) and rumen microorganism culture filtrate endoxylanases (▲).
Figure 5:
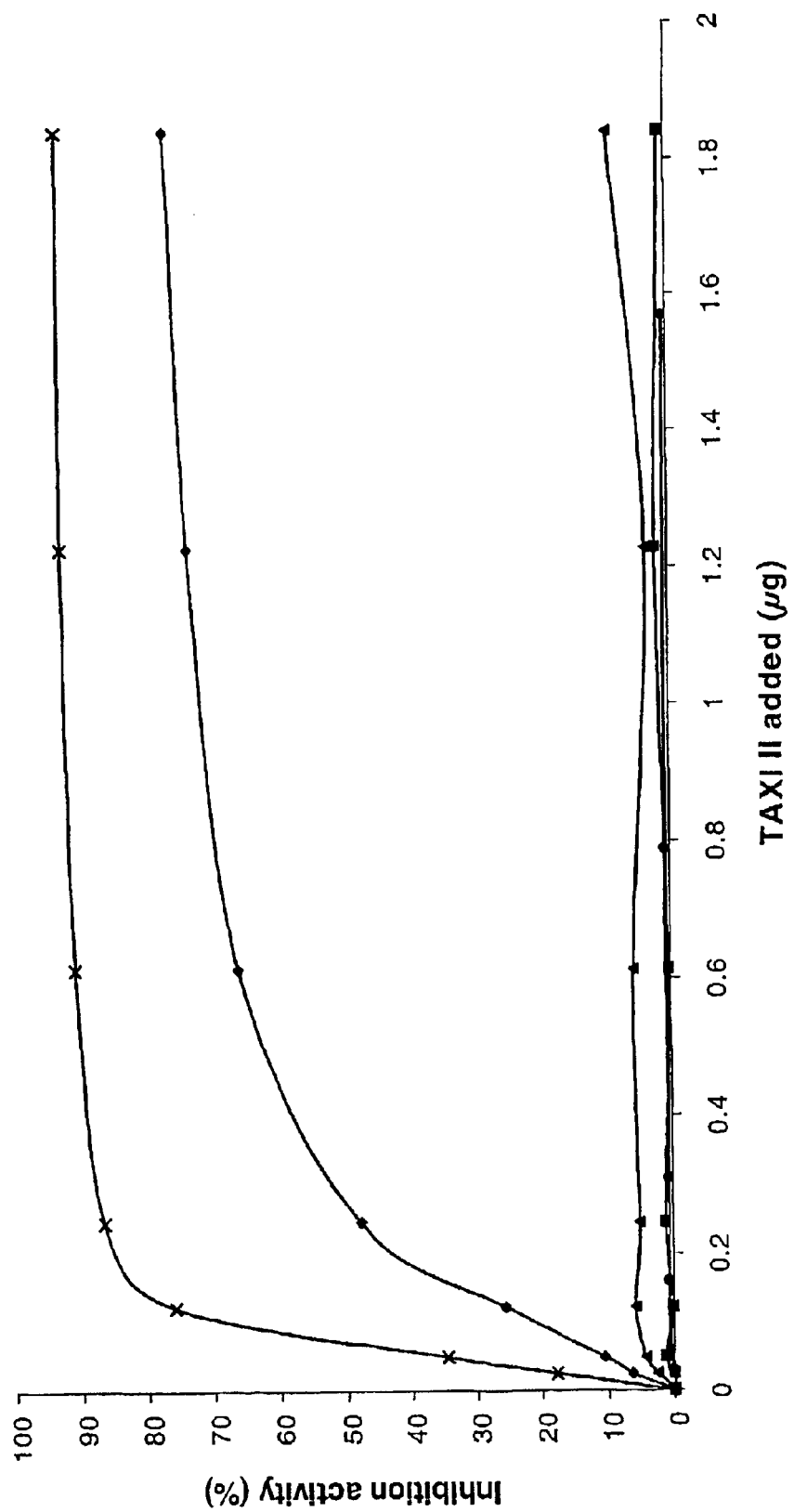
FIG. 5 shows the activities of different levels of TAXI II against five different endoxylanases, i.e. *A. aculeatus* (●), *A. niger* (■), *B. subtilis* (♦), *T. viride* (x) and rumen microorganism culture filtrate endoxylanases (▲).

FIGS. 4 and 5 show the activities of different levels of TAXI I and TAXI II respectively against five different endoxylanases, i.e. *A. aculeatus* (●), *A. niger* (■), *B. subtilis* (♦), *T. viride* (X) and rumen microorganism culture filtrate endoxylanases (▲). Except in the case of the *A. niger* endoxylanase, under the specified conditions TAXI I and TAXI II have similar inhibition activity profiles, which are depicted in FIGS. 4 and 5.

TAXI I has high activities against the *A. niger*, the *T. viride* and the *B. subtilis* endoxylanases, low activity against the rumen micro-organism endoxylanases and little if any activity against the *A. aculeatus* endoxylanase. The maxima of inhibition are slightly above 90% for the first two endoxylanases, ca. 82% for the *B. subtilis* endoxylanase and ca. 15% for the rumen micro-organism endoxylanases. Under the test conditions, different levels of TAXI I (ca. 0.10, ca. 0.08 and ca. 0.20 μg respectively) reduce the activities of the *A. niger*, the *T. viride* and the *B. subtilis* endoxylanase with 50%.

TAXI II has high activities against the *T. viride* and the *B. subtilis* endoxylanase, low activity against the rumen microorganism endoxylanases and little if any activity against the *A. niger* and the *A. aculeatus* endoxylanase. The maxima of inhibition are slightly above 90% for the first endoxylanase, ca. 77% for the *B. subtilis* endoxylanase and ca. 8% for the rumen micro-organism endoxylanases. As for TAXI I, different quantities of TAXI II (ca. 0.07 and ca. 0.28 μg respectively) reduce the activities of the *T. viride* and the *B. subtilis* endoxylanase with 50%.

Because after boiling (15 min, pH 5.0) no inhibition activity could be found against the mentioned endoxylanases, both inhibitors are heat sensitive.

Other xylanolytic enzymes, an arabinofuranosidase and a xylosidase from *A. niger*, were not inhibited by TAXI I and TAXI II.

Inhibition Type

Figure 6:
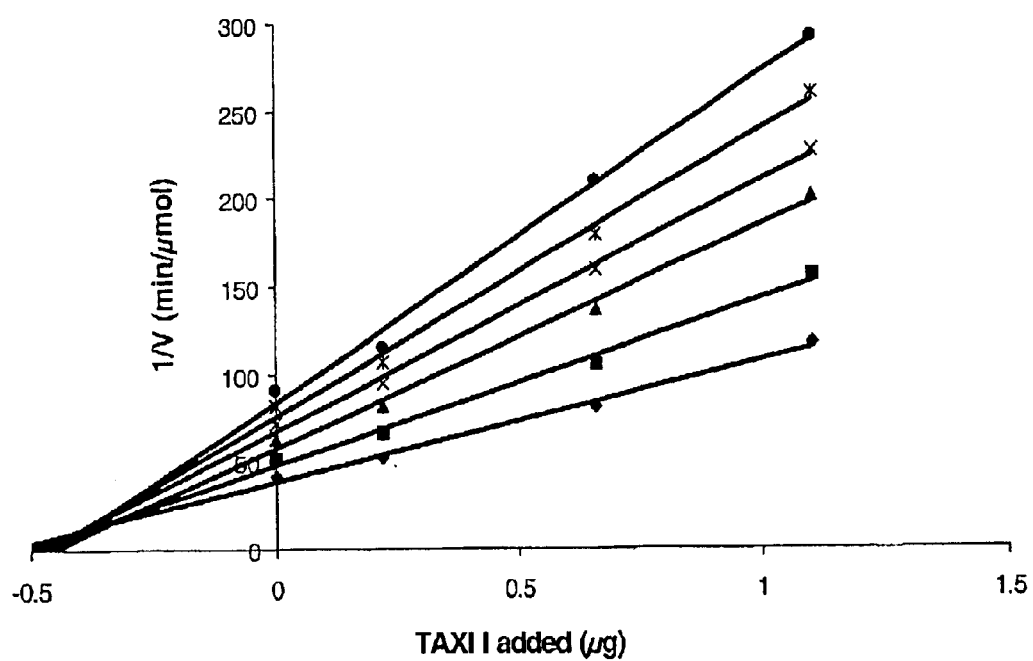
FIG. 6 shows the Dixon plots corresponding to TAXI I and *B. subtilis* endoxylanase for substrate concentrations [S]=5.00 (♦), 3.33 (■), 2.50 (▲), 2.00 (x), 1.67 (*) and 1.43 (●), mg/ml wheat arabinoxylan.

FIG. 6 shows the Dixon plots corresponding to TAXI I and *B. subtilis* endoxylanase for substrate concentrations [S]=5.00 (♦), 3.33 (■), 2.50 (▲), 2.00 (x), 1.67 (*) and 1.43 (●), mg/ml wheat arabinoxylan.

Figure 7:
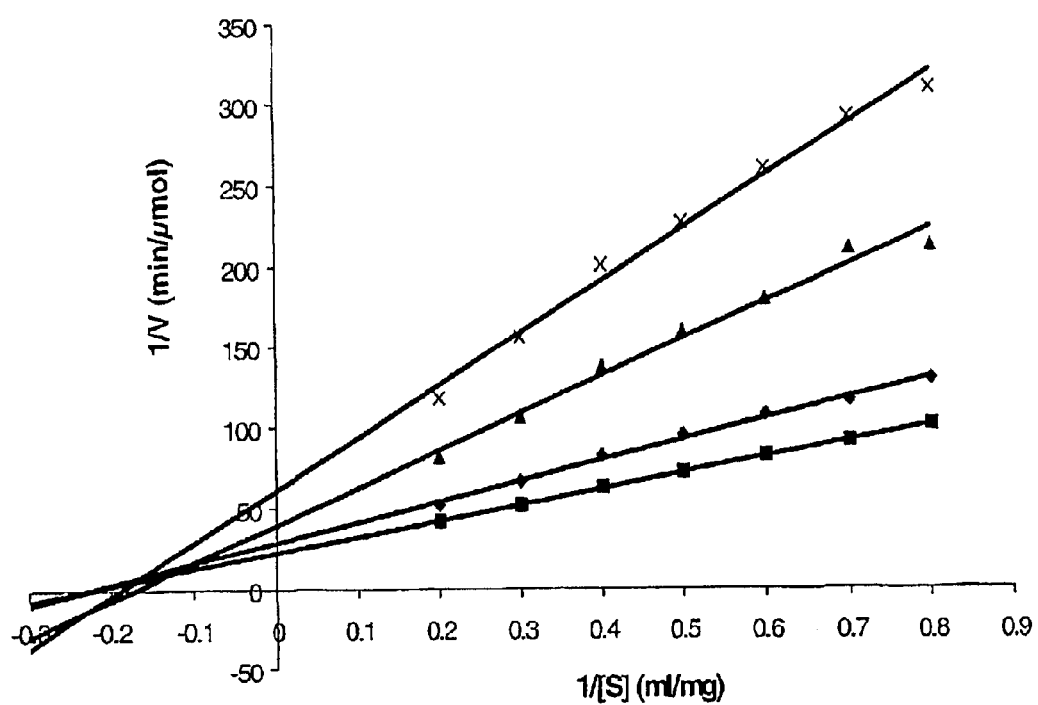
FIG. 7 shows the Lineweaver-Burk plots corresponding to TAXI I and *B. subtilis* endoxylanase for inhibitor quantities [I]=0.0 (■), 0.22 (♦), 0.66 (▲) and 1.10 (x) µg
Figure 8:
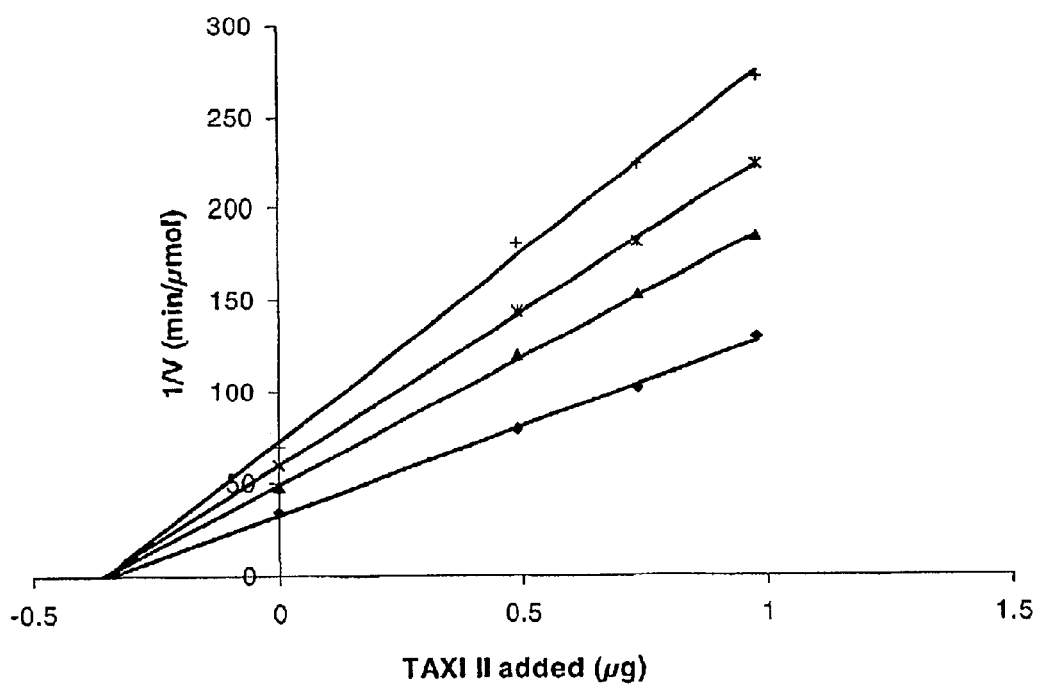
FIG. 8 shows the Dixon plots corresponding to TAXI II and *B. subtilis* endoxylanase for substrate concentrations [S]=5.00 (♦), 2.50 (▲), 1.67 (*) and 1.25 (+) mg/ml wheat arabinoxylan.

FIG. 7 shows the Lineweaver-Burk plots corresponding to TAXI I and *B. subtilis* endoxylanase for inhibitor quantities [I]=0.0 (■), 0.22 (♦), 0.66 (▲) and 1.10 (x) μg FIG. 8 shows the Dixon plots corresponding to TAXI II and *B. subtilis* endoxylanase for substrate concentrations [S]=5.00 (♦), 2.50 (▲), 1.67 (*) and 1.25 (+) mg/ml wheat arabinoxylan.

Figure 9:
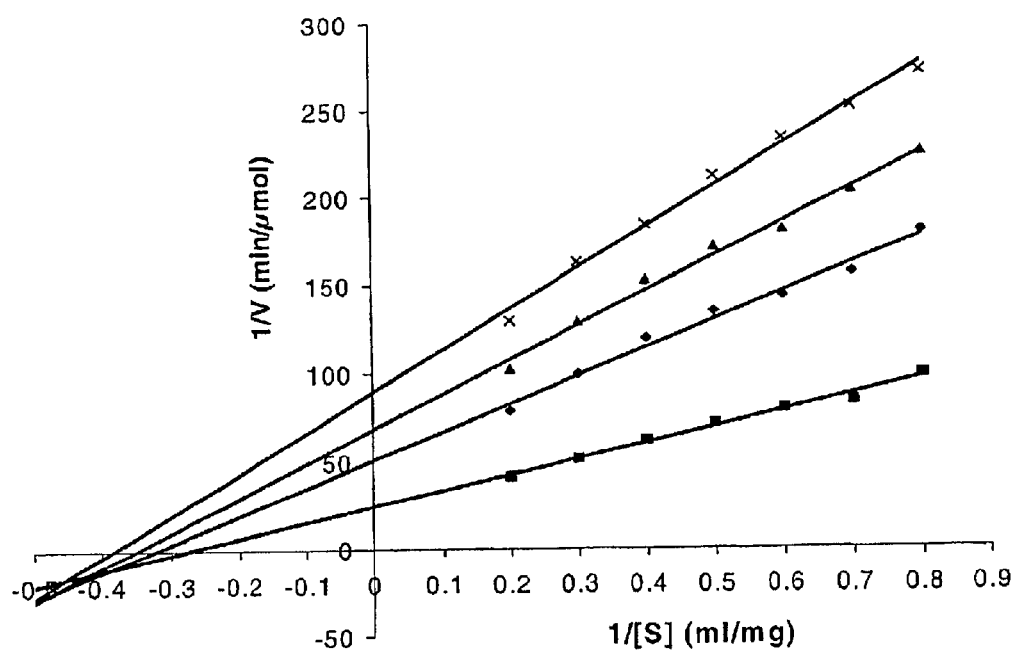
FIG. 9 shows the Lineweaver-Burk plots corresponding to TAXI II and *B. subtilis* endoxylanase for inhibitor quantities [I]=0.0 (■), 0.49 (♦), 0.74 (▲) and 0.98 (x) µg
Figure 10:
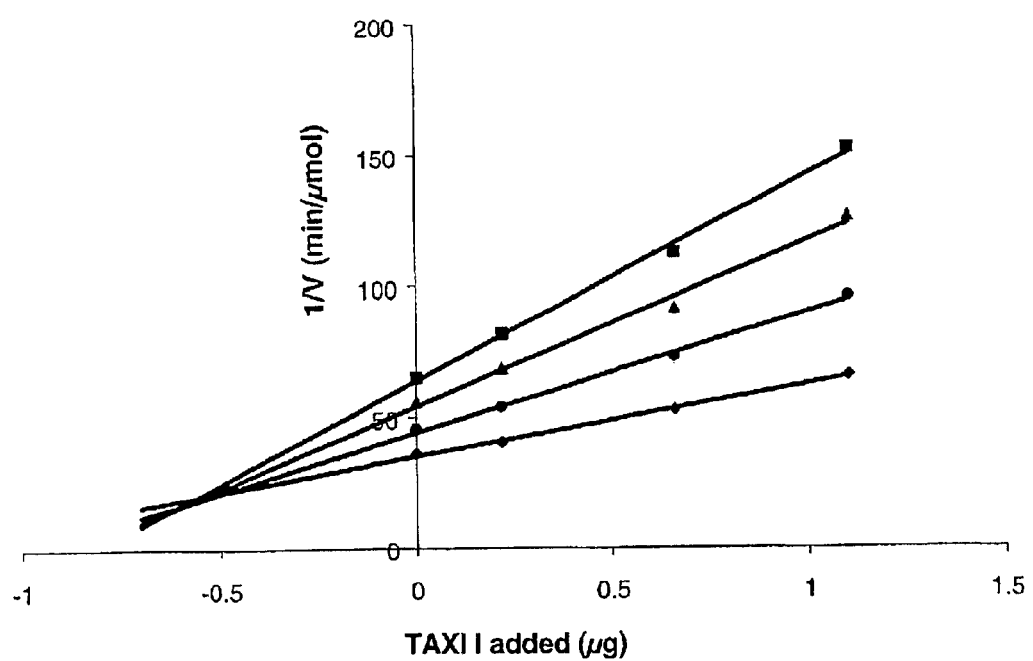
FIG. 10 shows the Dixon plots corresponding to TAXI I and *A. niger* endoxylanase for substrate concentrations [S]= 5.00 (♦), 3.33 (●), 2.50 (▲) and 2.00 (■) mg/ml wheat arabinoxylan.

FIG. 9 shows the Lineweaver-Burk plots corresponding to TAXI II and *B. subtilis* endoxylanase for inhibitor quantities [I]=0.0 (■), 0.49 (♦), 0.74 (▲) and 0.98 (x) μg FIG. 10 shows the Dixon plots corresponding to TAXI I and *A. niger* endoxylanase for substrate concentrations [S]= 5.00 (♦), 3.33 (●), 2.50 (▲) and 2.00 (■) mg/ml wheat arabinoxylan.

Figure 11:
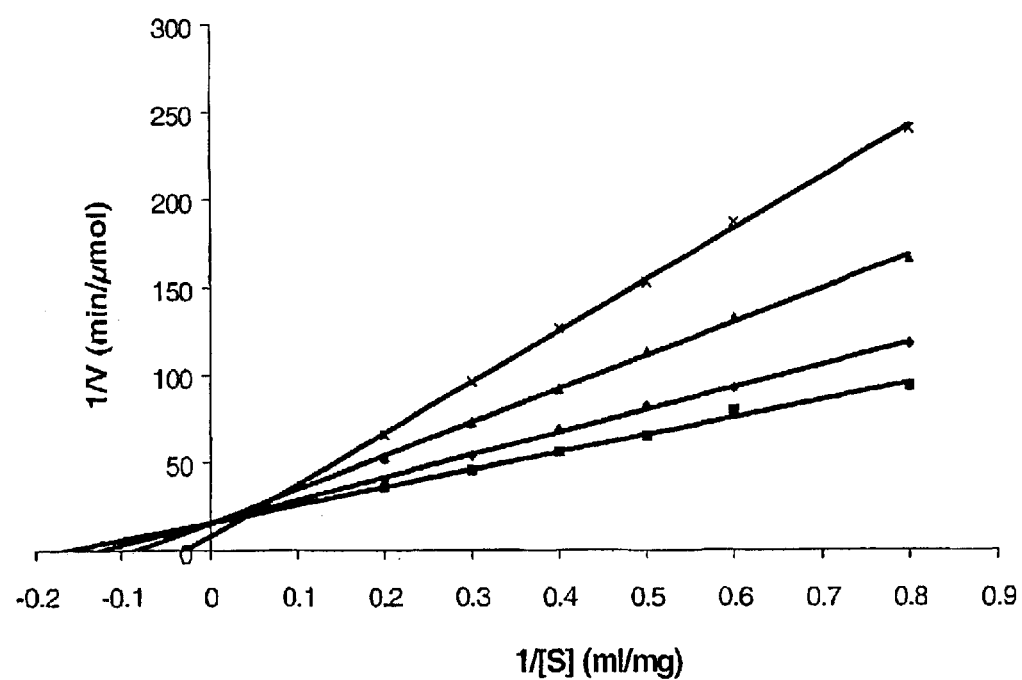
FIG. 11 shows the Lineweaver-Burk plots corresponding to TAXI I and *A. niger* endoxylanase for inhibitor quantities [I]=0.0 (■), 0.22 (♦), 0.66 (▲), 1.10 (x) µg

FIG. 11 shows the Lineweaver-Burk plots corresponding to TAXI I and *A. niger* endoxylanase for inhibitor quantities [I]=0.0 (■), 0.22 (♦), 0.66 (▲), 1.10 (x) μg Depending on the endoxylanase, two different types of inhibition were observed. TAXI I and TAXI II both inhibited the *B. subtilis* endoxylanase in a non-competitive manner (FIGS. 6, 7, 8 and 9), where as the *A. niger* endoxylanase was inhibited competitively by TAXI I (FIGS. 10 and 11). For non-competitive inhibition, the Dixon plot (inverse of reaction rate, 1/V, versus inhibitor concentration, [I]) corresponding to the different substrate concentrations (FIGS. 6 and 8) and the Lineweaver-Burk plot (inverse of reaction rate, 1/V, versus inverse of substrate concentration, 1/[S]) corresponding to different inhibitor concentrations (FIGS. 7 and 9) intersect on the horizontal axis in the left quadrant. In the case of competitive inhibition, however, the curves intersect in the left quadrant (FIG. 10) and on the vertical axis (FIG. 11) respectively.

Discussion

Two endoxylanase inhibitors (TAXI I and TAXI II) were purified from wheat and partially characterised. Both are non-glycosylated and have similar N-terminal amino acid sequences and SDS-PAGE profiles, indicating that there may be an evolutionary relationship between them. Their pI values are respectively ca. 8.8 and ca. 9.3 or higher. Except for the *A. niger* endoxylanase, TAXI I and TAXI II have, under the specified conditions, the same inhibition activity profiles, i.e. both inhibitors inhibited the *A. aculeatus*, *B. subtilis*, *T. viride* and rumen microorganism culture filtrate endoxylanases to a similar extent (FIGS. 4 and 5). In the case of the *A. niger* endoxylanase, however, TAXI I resulted in a strong inhibition where as for TAXI II little if any inhibition could be observed.

Using a BLAST (version 2.0.10) search [26] in public sequence databases, the N-terminal amino acid sequences of the 40.0 and 30.0 kDa polypeptides of TAXI I were found to be 66% identical with internal sequences of an extracellular dermal glycoprotein precursor from *Arabidopsis thaliana* (amino acids 32–46: LLLPVTKDPSTLQYT) and a glucose-6-phosphate isomerase from *Escherichia coli* (amino acids 449–460: KDPATLDYVVPF) in a 15- and 12-amino acid overlap (amino acids 3–17 and 9–20 of TAXI I) respectively. The 40.0 and 30.0 kDa polypeptides of TAXI II are 64% identical with an internal sequence of a ribulose-1,5-biphosphate carboxylase small subunit from Fritillaria agrestis (amino acids 38–51: PVTQKTATGLSTLP) in a 14-amino acid overlap (amino acids 8–21 of TAXI II).

The present results show that Debyser and Delcour [14] and Debyser et al. [17], in their reports on TAXI, probably studied a mixture of TAXI I and TAXI II. Indeed, mixtures of these two proteins with the above mentioned inhibition specificities may very well have resulted in the observation that TAXI inhibited B. subtilis endoxylanase more effectively than the corresponding A. niger enzyme. Because the authors only screened with A. niger endoxylanase to purify TAXI, they probably picked up $CEC_{wheat}$ I together with some material of $CEC_{wheat}$ II with CEC on SP Sepharose® Fast Flow (FIG. 1). Nevertheless, our observations are in line with the published [17] model for the molecular structure of the TAXI type endoxylanase inhibitors, maintaining that these proteinaceous inhibitors occur in two molecular forms A and B with a molecular mass of ca. 40.0 kDa. According to the model, following reduction with β-mercaptoethanol, form B dissociates in two fragments of ca. 10.0 and ca. 30.0 kDa, whereas the molecular mass of form A is not affected by the treatment. Since the N-terminal sequences of the ca. 30.0 and ca. 40.0 kDa polypeptides were identical, the ca. 10.0 and ca. 30.0 kDa polypeptides of form B, held together by one or more disulfide bounds, are probably derived from the ca. 40.0 kDa polypeptide (form A) by proteolytic modification. We have strong indications that form A is active as endoxylanase inhibitor, but to what extent form B is active, is not clear at present. It seems reasonable to assume that the first form (A) is a precursor of the second form (B) and that the inhibitor needs to be proteolytically modified to become more or less active. A mechanism where however a non-active protein is activated by proteolytic modification has been observed for an α-amylase inhibitor from bean (Phaseolus vulgaris L.) seeds [27, 28].

Studies on the inhibition type of TAXI I and TAXI II unexpectedly show that the type of inhibition depends on the endoxylanase used (FIGS. 6 to 11). The A. niger endoxylanase is inhibited by TAXI I by blocking the active site, i.e. TAXI I competes with arabinoxylan (competitive inhibition) and in the case of the B. subtilis endoxylanase, both TAXI I or TAXI II and arabinoxylan can bind and this independent of the binding order, i.e. TAXI I and TAXI II do not compete with arabinoxylan (non-competitive inhibition). The last type of inhibition is however in contrast to the findings of Sørensen and Poulsen [29] and Mclauchlan et al. [19] who for endoxylanase inhibitors only observed competitive inhibition. The present unexpected finding probably can be explained by the choice of endoxylanase they used to study the inhibition kinetics.

The above described results and FIG. 5 demonstrate, that with the latter type of inhibition inhibitor/enzyme complexes can be formed that still have some residual activity. After all, for the B. subtilis endoxylanase and TAXI I or TAXI II the inhibition (non-competitive) as a function of inhibitor quantity reaches a maximum at about 80% inhibition, whereas for the A. niger endoxylanase and TAXI I (competitive inhibition) this is at about 95%. These residual endoxylanase activities can lead to different arabinoxylan degradation patterns and products than the endoxylanase activity in absence of TAXI I and TAXI II. This in turn implies that endoxylanase inhibitors can alter the functionality of certain endoxylanases, such as the B. subtilis endoxylanase, and/or can have an impact on the relative affinity and/or hydrolysis specificity and/or rate versus waterextractable and/or water-unextractable arabinoxylans.

In contrast to TAXI type endoxylanase inhibitors, the more recent inhibitor described by McLauchlan et al. [19] and Hessing and Happe [20] is monomeric and glycosylated and has a molecular mass of ca. 29.0 kDa. Its N-terminal amino acid sequence is 87% identical with a sequence of rice chitinase III in a 15-amino acid overlap and shows no homology with the reported amino acid sequences of either TAXI I or TAXI II. The monomeric endoxylanase inhibitor was found to inhibit an A. niger endoxylanase in a competitive manner.

In wheat, endoxylanase inhibitors may have a dual function. They possibly play an important role in regulation of plant metabolism by inhibiting endogenous endoxylanases and/or in plant defence by inhibiting exogenous endoxylanases, produced by micro-organisms and predators. In contrast to exogenous endoxylanases, endogenous endoxylanases of wheat are less well documented apart from the work by Cleemput [30] and Cleemput et al. [22, 31] who purified two endoxylanases with different substrate specificities.

Example 2

Isolation and Characterization of a Xylanase Inhibitor from Barley (HVXI)

Further Purification of a Barley Endoxylanase Inhibitor

Barley endoxylanase inhibitor, HVXI, was further purified using a method identical to that for the further purification of TAXI II (cfr. supra). After each purification step, the resulting fractions were assayed for endoxylanase inhibition activity, both with B. subtilis and A. niger endoxylanases Step 1. Purification By CEC $CEC_{barley}$ was separated in a way analogous to that of $CEC_{wheat}$, yielding fraction $CEC_{barley}$' (6.84 g)

Step 2. Purification by Gel Permeation Chromatography (GPC)

$CEC_{barley}$' was separated in a way analogous to that of $CEC_{wheat}$ I or $CEC_{wheat}$ II, yielding fraction $GPC_{barley}$ (640 mg in 3300 ml).

Step 3. Purification By CEC

HVXI was purified to homogeneity from $GPC_{barley}$ much as TAXI II from $GPC_{wheat}$ II, i.e. a first separation by CEC was performed on MonoS® at pH 6.5 followed by a second separation on the same column at pH 4.0. For both separations, the same gradient and flow were used. We finally obtained 18.0 mg HVXI.

Results

Inhibitor Purification

Figure 12:
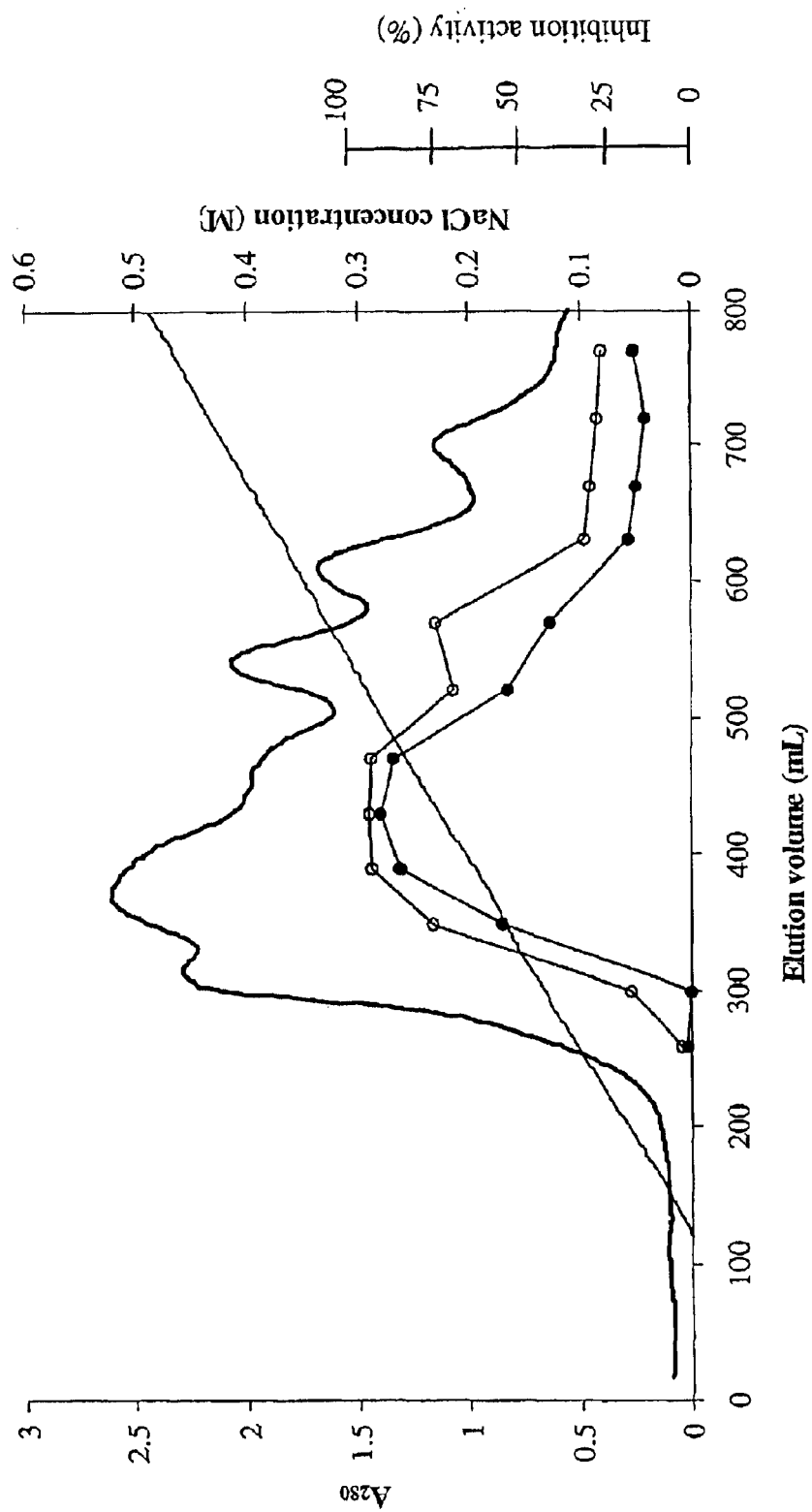
FIG. 12 shows the SP Sepharose® Fast Flow chromatogram (—) of $CEC_{barley-}$ material, with indication of the NaCl-gradient (—) and the inhibition activities against *A. niger* (○) and *B. subtilis* (•) endoxylanases.
Figure 13:
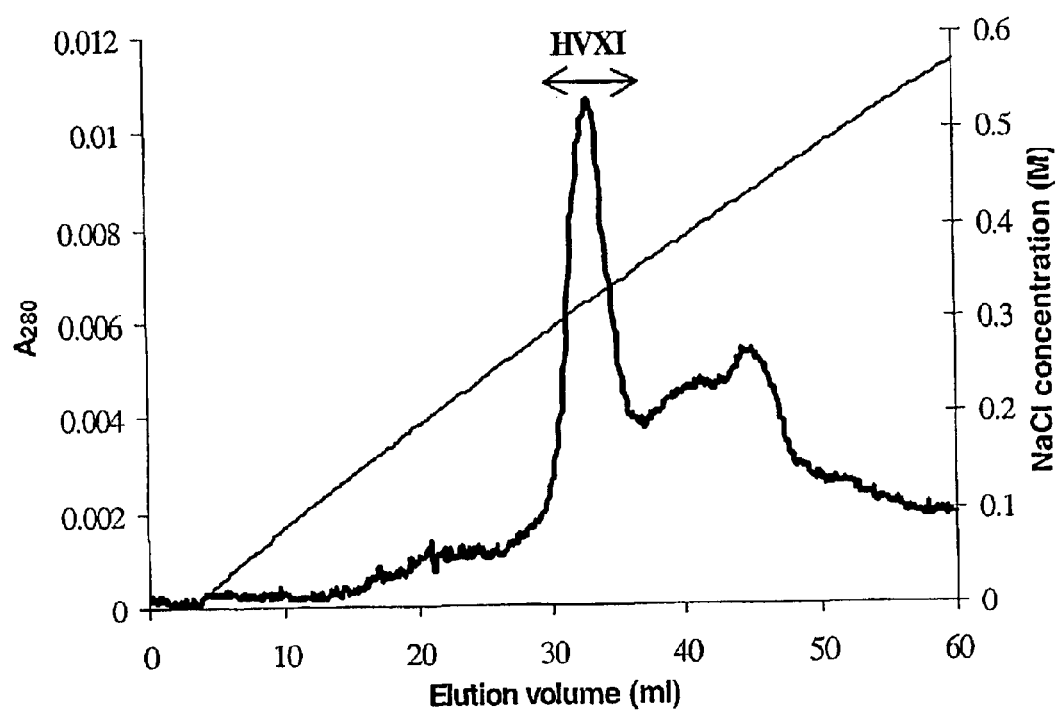
FIG. 13 displays the chromatogram (—) of the final separation of HVXI on MonoS® with indication of the NaCl-gradient (—). With CEC on MonoS® the fractions containing inhibitor elute at NaCl concentration of 0.30 to 0.35 M.

By using an identical purification procedure as described for TAXI II, HVXI was purified from barley whole meal. FIG. 12 shows the SP Sepharose® Fast Flow chromatogram (—) of $CEC_{barley}$-material, with indication of the NaCl-gradient (—) and the inhibition activities against A. niger (o) and B. subtilis (•) endoxylanases. With CEC on SP Sepharose® Fast Flow the fractions with inhibition activity elute at NaCl concentration of 0.15 to 0.35 M. Compared with the separation of $CEC_{wheat}$ on SP Sepharose® Fast Flow (cfr. Supra), a somewhat similar profile was obtained when screening with the A. niger enzyme, apart from a right hand shoulder, possibly indicating an additional HVXI inhibitor. In the profile resulting from screening with B. subtilis endoxylanase the right hand shoulder was very weak, indicating again that the method as used here allows to distinguish between inhibitors of different specificity. FIG. 13 displays the chromatogram (—) of the final separation of HVXI on MonoS® with indication of the NaCl-gradient (—). With CEC on MonoS® the fractions containing inhibitor elute at NaCl concentration of 0.30 to 0.35 M.

Inhibitor Partial Molecular Characterisation

Figure 14:
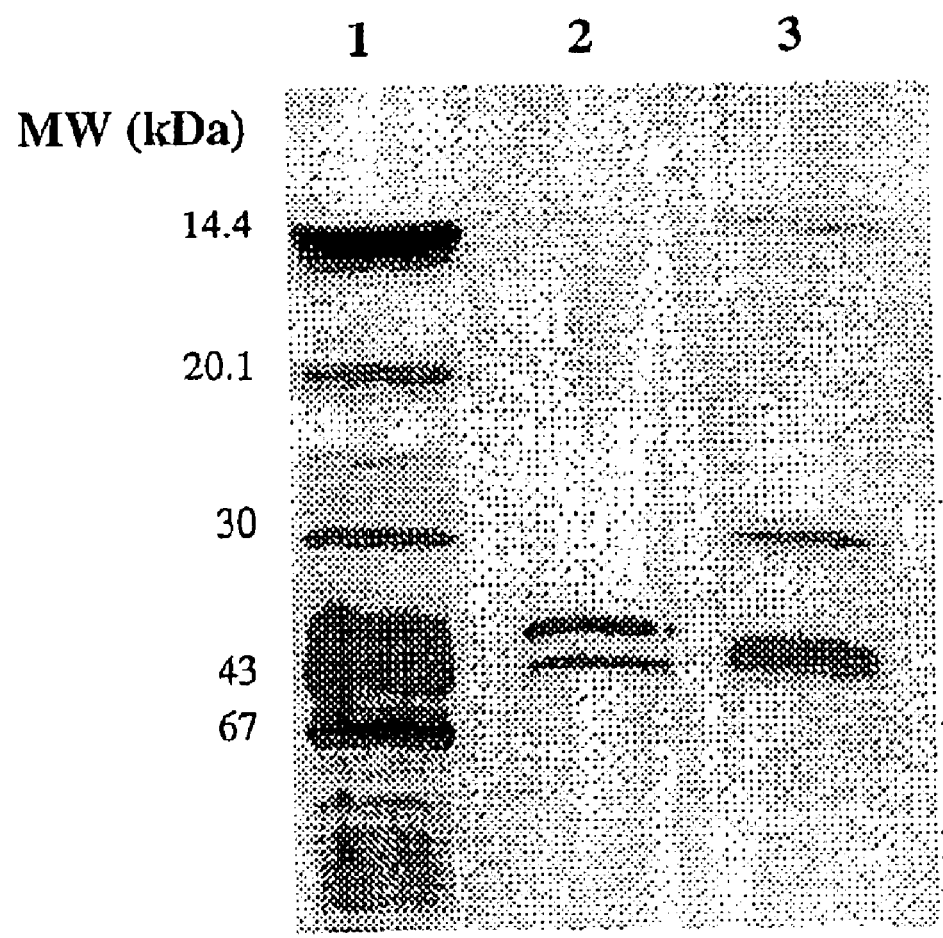
FIG. 14 shows the SDS-PAGE profile of HVXI with in lane 1 the low molecular (—) mass markers (the size of the markers indicated on the left), in lane 2 pure inhibitor under non-reducing conditions and in lane 3 pure inhibitor under reducing conditions. Under non-reducing conditions, the purified inhibitor migrated as a double protein band with a molecular mass of ca. 40.0 kDa.

FIG. 14 shows the SDS-PAGE profile of HVXI with in lane 1 the low molecular mass markers (the size of the markers indicated on the left), in lane 2 pure inhibitor under non-reducing conditions and in lane 3 pure inhibitor under reducing conditions. Under non-reducing conditions, the purified inhibitor migrated as a double protein band with a molecular mass of ca. 40.0 kDa. In the presence of β-mercaptoethanol, the SDS-PAGE gel showed three protein bands with molecular masses of ca. 40.0 kDa; ca. 30.0 kDa and ca. 10.0 kDa. The pI of the inhibitor was at least ca. 9.3 and HVXI was not glycosylated.

The ca. 40.0 kDa and ca. 30.0 kDa polypeptides both share the same N-terminal amino acid sequence SEQ ID No. 3, indicating that the ca. 30.0 kDa polypeptide is proteolytically derived from the ca. 40.0 kDa protein. The N-terminal amino acid sequence obtained for the ca. 10.0 kDa polypeptide is SEQ ID No. 6. The N-terminal amino acid sequences of the ca. 40.0 kDa and ca. 30.0 kDa polypeptide of HVXI show a high identity (94.4% identity in a 18-amino acid overlap and 90.0% identity in a 20-amino acid overlap respectively) with those of TAXI I and TAXI II. The N-terminal amino acid sequence of the ca. 10.0 kDa polypeptide of HVXI is less similar. It has 60.0% identity with the amino acid sequence of the ca. 10.0 kDa polypeptides of TAXI I and TAXI II in 15-amino acid overlaps.

Using a BLAST (version 2.0.10) search [26], the N-terminal sequence of the ca. 40.0 kDa and ca. 30.0 kDa polypeptides (amino acids 8–18) revealed a 72.7% identity in an 11-amino acid overlap with an internal sequence PITKDAHTSIY of a hypothetical protein from *Arabidopsis thaliana* (amino acids 344–354). The sequence of the ca. 10.0 kDa polypeptide showed 60.0% identity with the sequence GALATPGYPAAPYG of "osr40g3", a rice (*Oryza sativa* L.) protein.

Inhibition Activities Against Xylanolytic Enzymes

Figure 15:
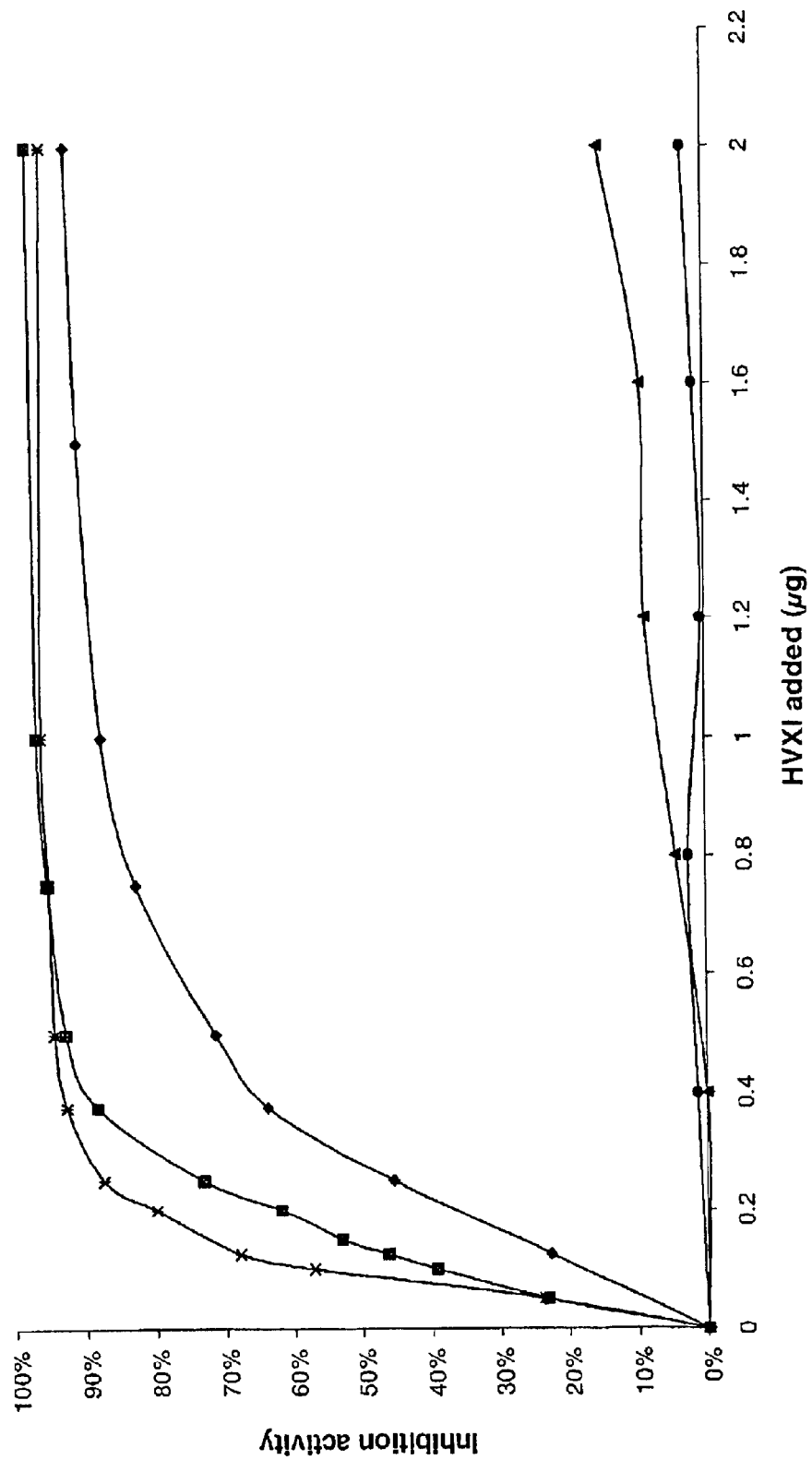
FIG. 15 shows the activities of different levels of HVXI against five different endoxylanases, i.e. *A. aculeatus* (●), *A. niger* (■), *B. subtilis* (♦), *T. viride* (x) and rumen microorganism culture filtrate endoxylanases (▲).

FIG. 15 shows the activities of different levels of HVXI against five different endoxylanases, i.e. *A. aculeatus* (●), *A. niger* (■), *B. subtilis* (♦), *T. viride* (x) and rumen microorganism culture filtrate endoxylanases (▲).

HVXI has high activities against the *A. niger*, the *T. viride* and the *B. subtilis* endoxylanases (family 11), low activity against the rumen micro-organism endoxylanases and little if any activity against the *A. aculeatus* endoxylanase (family 10). The maxima of inhibition are slightly above 95% for the first two endoxylanases, ca. 92% for the *B. subtilis* endoxylanase and ca. 15% for the rumen micro-organism endoxylanases. It should be noticed that in the case of HVXI, the difference between the maxima of inhibition for the *A. niger* and the *T. viride* endoxylanases on one hand and the maximum of inhibition for the *B. subtilis* endoxylanase on the other hand, is not as pronounced as in the case of TAXI I. Under the test conditions, different levels of HVXI (ca. 0.13, ca. 0.08 and ca. 0.27 μg respectively) reduce the activities of the *A. niger*, the *T. viride* and the *B. subtilis* endoxylanase with 50%.

Because after boiling (15 min, pH 5.0) no inhibition activity could be found against each of the mentioned endoxylanases, HVXI is heat sensitive.

Other AX hydrolysing enzymes, like an α-arabinofuranosidase and a β-xylosidase from *A. niger*, were not inhibited.

Discussion

We have purified and partially characterized HVXI, an endoxylanase inhibitor of barley. The SP Sepharose® Fast Flow profiles of $CEC_{barley}$ however strongly suggest the presence of an additional endoxylanase inhibitor. HVXI is strongly related to TAXI I and TAXI II, since similar characteristics, N-terminal amino acid sequences and gel profiles under reducing and non-reducing conditions have been found for these wheat endoxylanase inhibitors (cfr. supra). In contrast, the inhibitor described by McLauchlan et al. [19] and Hessing and Happe [20] is a glycosylated, monomeric (single chained), basic protein with a molecular mass of 29 kDa. In addition, its N-terminal amino acid sequence showed 86% identity with the sequence of chitinase III from rice, whereas the N-termini of HVXI did not reveal such high identity with known proteins.

We believe that, much as TAXI I and TAXI II, HVXI occurs as two molecular forms, both with a molecular mass of ca. 40.0 kDa [16]. The first form exists as a single polypeptide chain. After proteolytic modification, it is transformed into the second form, which is composed of two disulfide linked subunits of ca. 30.0 kDa and ca. 10.0 kDa. As in the case of TAXI I and TAXI II, we have strong indications that the non-proteolytically modified form is active, but to what extent the modified one is active, is still unclear. However, also here, it is reasonable to assume that the first form A is the precursor of the second form B and that, following proteolytic modification, the inhibitor becomes more or less active.

In the presence of HVXI, different endoxylanases were inhibited to a varying degree and HVXI showed a similar effect on the endoxylanase activities as TAXI I (cfr. supra). As in the case of TAXI I and TAXI II, part of the endoxylanase selectivity may be due to the fact that the enzymes tested belong to different families, i.e. family 10 or family 11. However, other factors should not be ignored, since, in the presence of the inhibitors, not all the family 11 enzymes tested reacted in the same way.

In general, proteinaceous enzyme inhibitors may be involved in plant defence mechanisms or in regulating certain metabolic activities in the plant [32, 9]. The endoxylanase inhibitor(s) in barley may have both functions. On the one hand, they may prevent the degradation of AX by phythopathogenic microorganisms, on the other hand they may regulate the AX degradation during germination. It has been shown that in extracts of germinating barley the xylan hydrolase activity appears several days later than (1-3),(1-4)-β-glucanases [33]. Although the endoxylanase genes are transcribed about 24 hours after those of the (1-3),(1-4)-β-glucanases [34], it has been suggested that the late appearance of the endoxylanase activity is due to a strong binding of these enzymes with the (aleurone) cell walls [33, 35]. However, the presence of endoxylanase inhibitors may also explain these observations.

Example 3

Isolation of Endoxylanase Inhibitors from Commercial Wheat Flour, Rye Flour and Barley Whole Meal Using Affinity Chromatography with Immobilised *B. subtilis* or *A. niger* Endoxylanase Experimental Methods Materials N-hydroxysuccinimide(NHS)-activated Sepharose® 4 Fast Flow was purchased from Pharmacia Biotech (Uppsala, Sweden). Bakery enzyme preparation, Grindamyl® H 640 was from Danisco Cultor (Brabrand, Denmark). An *A. niger* endoxlanase preparation was obtained from Quest International (Naarden, the Netherlands). Rye (*Secale cereale* L., var. Halor) was from AVEVE (Landen, Belgium) and was milled with a Bühler MLU-202 mill. All other materials were as in examples 1 and 2.

Protein Determination

Protein concentrations were determined in accordance with the Coomassie Brilliant Blue method of Bradford [21] with BSA as a standard.

Endoxylanase Inhibition Assay Procedure

The inhibition activities were determined as described in the general experimental methods for examples 1 and 2.

Protein Electrophoresis and Sequencing

SDS-PAGE and protein sequencing were performed as described in the general experimental methods for examples 1 and 2.

Preparation of the Affinity Column

B. subtilis endoxylanase (XBS) was partially purified from a commercially available bakery enzyme preparation (Grindamyl® H 640) by elution on a cation exchange column (MonoS® HR 5/5) at pH 4.0 (25 mM sodium acetate) using a linear salt gradient from 0.0 to 1.0 M NaCl.

A. niger endoxylanase (XAN) was purified from a commercial Quest preparation by anion exchange chromatography (MonoQ® HR 5/5) at pH 8.0 (25 mM Tris/HCl) using a linear salt gradient from 0.0 to 1.0 M NaCl.

NHS-activated Sepharose® 4 Fast Flow (7.0 ml) was transferred to a small column of 15.0 ml, sealable at top and bottom. The matrix was washed with 1 mM HCl solution (70.0 ml). B. subtilis endoxylanase (50 mg) was dissolved in sodium bicarbonate buffer (0.2 M, pH 8.3; 7.0 ml) containing 0.5 M NaCl. Just before coupling, the activated matrix was washed with the same sodium bicarbonate buffer. The XBS solution (7.0 ml) was applied on top of the matrix. When ca. 4.0 ml of the enzyme solution had entered the matrix, the column was sealed and the coupling reaction was started. Coupling was performed at room temperature for 2.5 h, while the mixture was shaken. After the incubation period, the uncoupled endoxylanase was removed by washing with an ethanol amine solution (0.5 M, pH 8.3) containing 0.5 M NaCl (35.0 ml). An additional 5.0 ml of the same ethanol amine solution was added, the column was sealed and the mixture was shaken and allowed to react for 4 h at room temperature. The ethanol amine solution was replaced once during this incubation period. Finally, the matrix was washed successively with glycine solution (0.1 M, pH 3.0) containing 0.5 M NaCl (35.0 ml) and ethanol amine solution (0.5 M, pH 8.3) containing 0.5 M NaCl (35.0 ml).

The preparation of the affinity column with immobilised A. niger endoxylanase used an identical procedure, but starting from a XAN solution (50 mg in 7.0 ml).

Purification Method Using the XBS Affinity Column

Step I. Extraction and Concentration

The extraction of wheat flour and barley whole meal, the successive concentration and partial purification were performed as described in the general experimental methods for examples 1 and 2 resulting in $CEC_{wheat}$ and $CEC_{barley}$ material. From 2.5 kg of wheat flour, approximately 4.4 g of $CEC_{wheat}$ material was obtained, Rye flour (2.0 kg) was extracted with 20.0 l of 0.1% (w/v) ascorbic acid in water. The extract was further treated as described for wheat and barley in the general experimental methods for examples 1 and 2 yielding the $CEC_{rye}$ material.

Step II. Purification By Affinity Chromatography (AFC)

Batches of the $CEC_{wheat}$ (400 mg), $CEC_{rye}$ (250 mg) and $CEC_{barley}$ (250 mg) material were dissolved in sodium acetate buffer (25 mM, pH 5.0; 25 ml, 10 ml and 10 ml respectively) containing 0.2 M NaCl and applied to the affinity column with immobilised B. subtilis endoxylanase (equilibrated with the same buffer) at a flow rate of 0.33 ml/min. Proteins with endoxylanase inhibiting activity were eluted with 5.0 ml of a 0.25 M Tris/HCl buffer (pH 10.0) at a flow rate of 1.0 ml/min.

The eluted fractions were neutralized immediately with acetic acid (1.0M) and dialysed against sodium acetate buffer (25 mM, pH 4.0, 48 h) or were subjected to a buffer exchange (same buffer) using a PD-10 column, resulting in the $AFC_{wheat}$ (30.5 mg protein in 187 ml), $AFC_{rye}$ and $AFC_{barley}$ material, respectively.

Step IIIa. Purification of Wheat Endoxylanase Inhibitors By CEC

Three separate batches of the $AFC_{wheat}$ solution (62 ml) was applied on a MonoS® HR 5/5 column, previously equilibrated with sodium acetate buffer (25 mM, pH 4.0). The bound proteins were eluted with a linear gradient of 0.0–0.6 M NaCl in 60.0 ml at a flow rate of 1.0 ml/min. This resulted in two inhibitor protein fractions, one eluting at 0.22–0.30 M NaCl (wheat inhibitor fraction I) and one eluting at 0.36–0.44 M NaCl (wheat inhibitor fraction II). The collected inhibitor fractions I (13.8 mg protein in 36.0 ml) and II (5.5 mg protein in 33.0 ml) were dialysed against sodium acetate buffer (25 mM, pH 5.0) and sodium phosphate buffer (20 mM, pH 6.5) respectively.

In a final step wheat inhibitor fractions I and II were separated on MonoS® HR 5/5 columns, equilibrated with sodium acetate buffer (25 mM, pH 5.0) and sodium phosphate buffer (20 mM, pH 6.5) respectively. In both cases, elution was with a linear gradient of 0.0–0.6 M NaCl in 60.0 ml at a flow rate of 1.0 ml/min.

Step IIIb. Purification of Rye Endoxylanase Inhibitors By CEC

The $AFC_{rye}$ material was further fractionated on a MonoS® column, equilibrated with a 25 mM sodium acetate buffer (pH 4.0). The bound proteins were eluted with a linear gradient of 0.0 to 0.6 M NaCl in 60.0 ml at a flow rate of 1.0 ml/min and collected in 0.5 ml fractions. This resulted in four separate inhibitor solutions, which were subjected to a buffer exchange [sodium acetate buffer (25 mM, pH 5.0)] (=rye inhibitor fractions I–IV).

The different rye inhibitor fractions were seperated with the MonoS® column, equilibrated with a 25 mM sodium acetate buffer (pH 5.0) and using the same elution conditions as described above. Fractions (0.5 ml) were collected and assayed for their ability to inhibit the A. niger, B. subtilis and T. viride endoxylanases.

Purification Method Using the XAN Affinity Column

The $CEC_{wheat}$ material (400 mg) was dissolved in sodium acetate buffer (25 mM, pH 5.0; 25 ml) 0.2 M NaCl and applied to the affinity column with immobilised A. niger endoxylanase (equilibrated with the same buffer) at a flow rate of 0.33 ml/min. A protein fraction containing endoxylanase inhibiting activity was eluted with 5.0 ml of deionised water. More endoxylanase inhibiting proteins were eluted with 5.0 ml of a 0.25 M Tris/HCl buffer (pH 10.0). The flow rate during elution was 1.0 ml/min.

Results

Purification By Affinity Chromatography with Immobilised XBS

Figure 16:
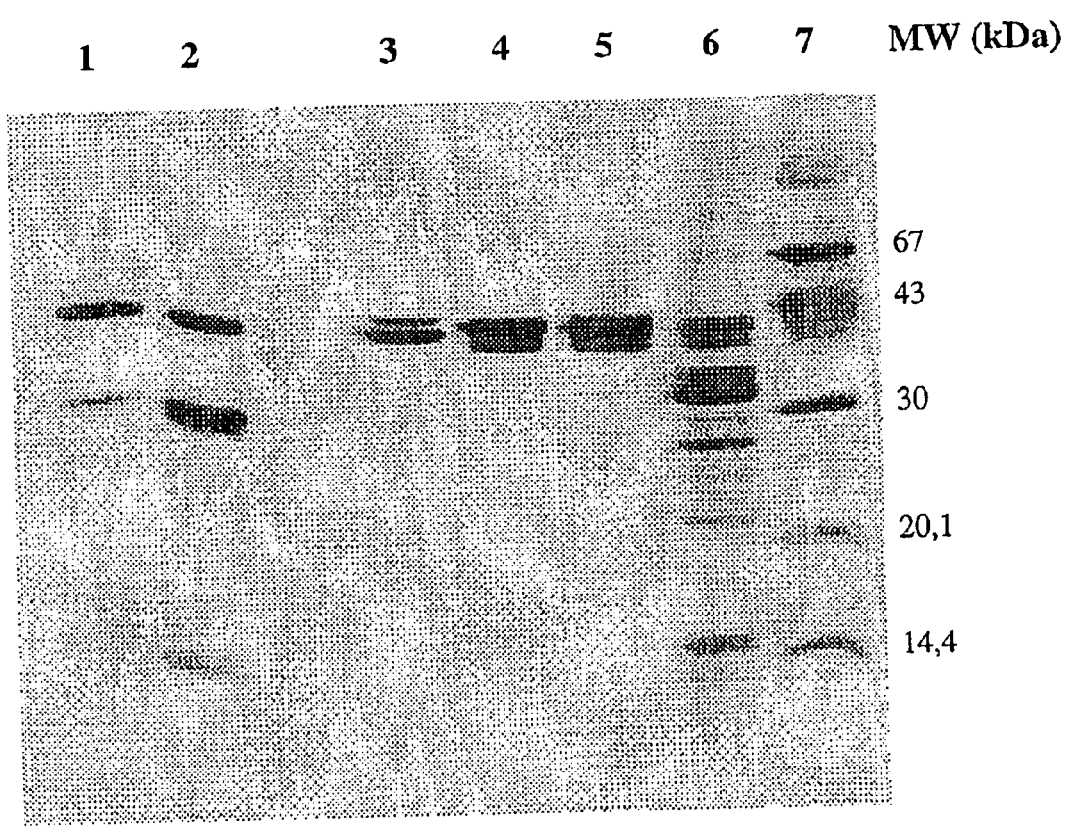
FIG. 16 shows the SDS-PAGE profiles of wheat inhibitor fractions I and II under reducing conditions (lanes 2 and 1 respectively) and non-reducing conditions (lanes 4 and 3 respectively), of the $AFC_{wheat}$ material, the $CEC_{wheat}$ material and the low molecular mass markers (the size of the markers indicated on the right) under non-reducing conditions (lanes 5, 6 and 7 respectively).

FIG. 16 shows the SDS-PAGE profiles of wheat inhibitor fractions I and II under reducing conditions (lanes 2 and 1 respectively) and non-reducing conditions (lanes 4 and 3 respectively), of the $AFC_{wheat}$ material, the $CEC_{wheat}$ material and the low molecular mass markers (the size of the markers indicated on the right) under non-reducing conditions (lanes 5, 6 and 7 respectively).

SDS-PAGE analysis under reducing and non-reducing conditions of the $AFC_{wheat}$, $AFC_{rye}$, $AFC_{barley}$ and of the wheat and rye inhibitor fractions obtained after fractionation on MonoS® at pH 4.0, showed that all isolated proteins are of the same general molecular structure as described for TAXI I and TAXI II in examples 1 and 2, i.e. a form A, which consists of a single polypeptide chain of ca. 40 kDa, and a form B, which consists of two disulfide linked subunits of ca. 30 and ca. 10 kDa. Hence, the B. subtilis enzyme has a high selective binding affinity for the 'TAXI'-like proteins, present in wheat, rye and barley.

Purification of Wheat Endoxylanase Inhibitors

Figure 17:
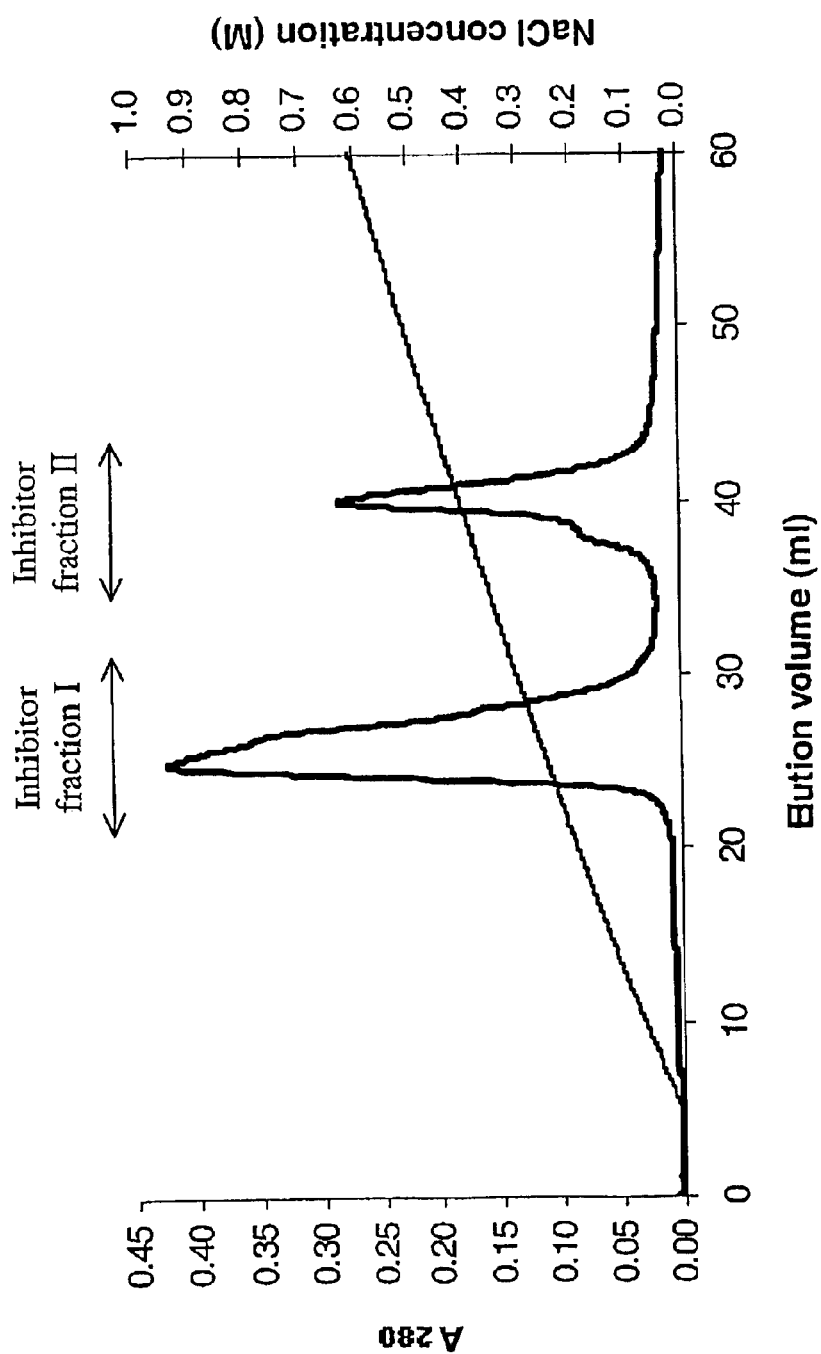
FIG. 17 shows the chromatogram (—) and the NaCl-gradient (—) of the separation of $AFC_{wheat}$ solution on a MonoS® column at pH 4.0, resulting in inhibitor fractions I and II.

FIG. 17 shows the chromatogram (--) and the NaCl gradient (—) of the separation of $AFC_{wheat}$ solution on a MonoS® column at pH 4.0, resulting in inhibitor fractions I and II.

The eluate (10 µl) of the affinity column contained high inhibition activity against the A. niger (95.2% inhibition) and the B. subtilis (87.3% inhibition) endoxylanases. Wheat inhibitor fraction I (10 µl) also inhibited both enzymes to a great extent (92.1% and 84.3% inhibition respectively) whereas wheat inhibitor fraction II (20 µl) inhibited the A. niger endoxylanase (13.4% inhibition) much less than the B. subtilis endoxylanase (81.4% inhibition). Fractionation of inhibitor fraction I on a MonoS® column at pH 5.0 and similar fractionation of inhibitor fraction II at pH 6.5 resulted in two and three distinct inhibitor peaks respectively.

Figure 18:
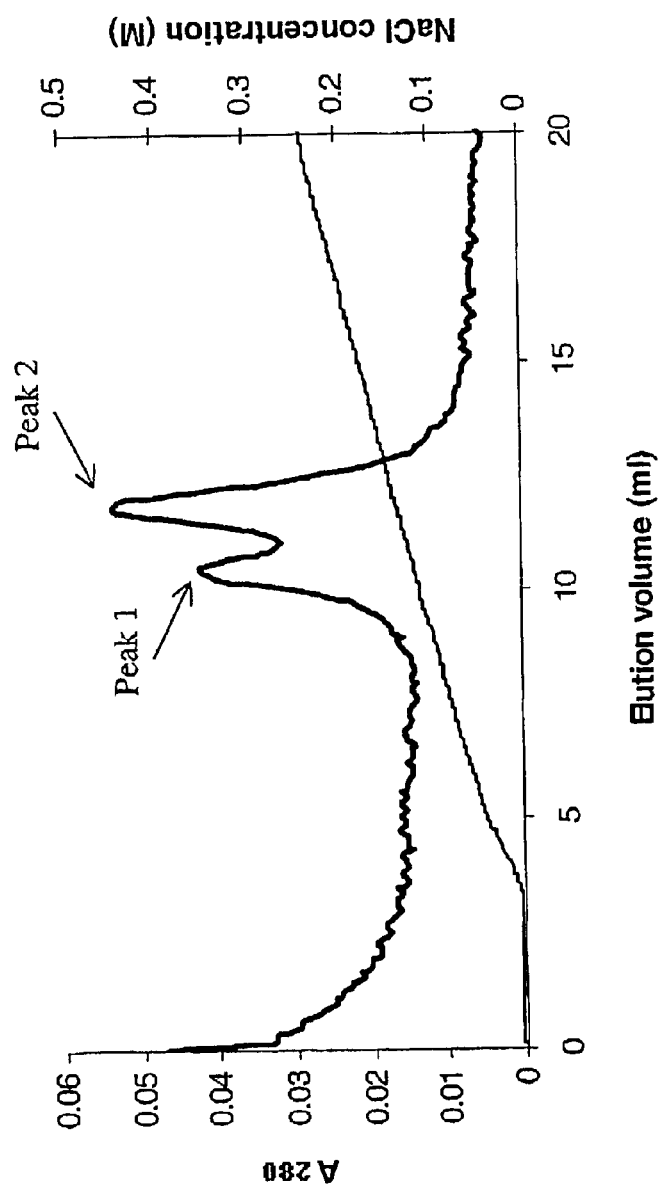
FIG. 18 shows the chromatogram (—) and the NaCl gradient (—) of the separation of the inhibitor fraction I on a MonoS® column at pH 5.0.

FIG. 18 shows the chromatogram (--) and the NaCl gradient (--) of the separation of the inhibitor fraction I on a MonoS® column at pH 5.0.

Figure 19:
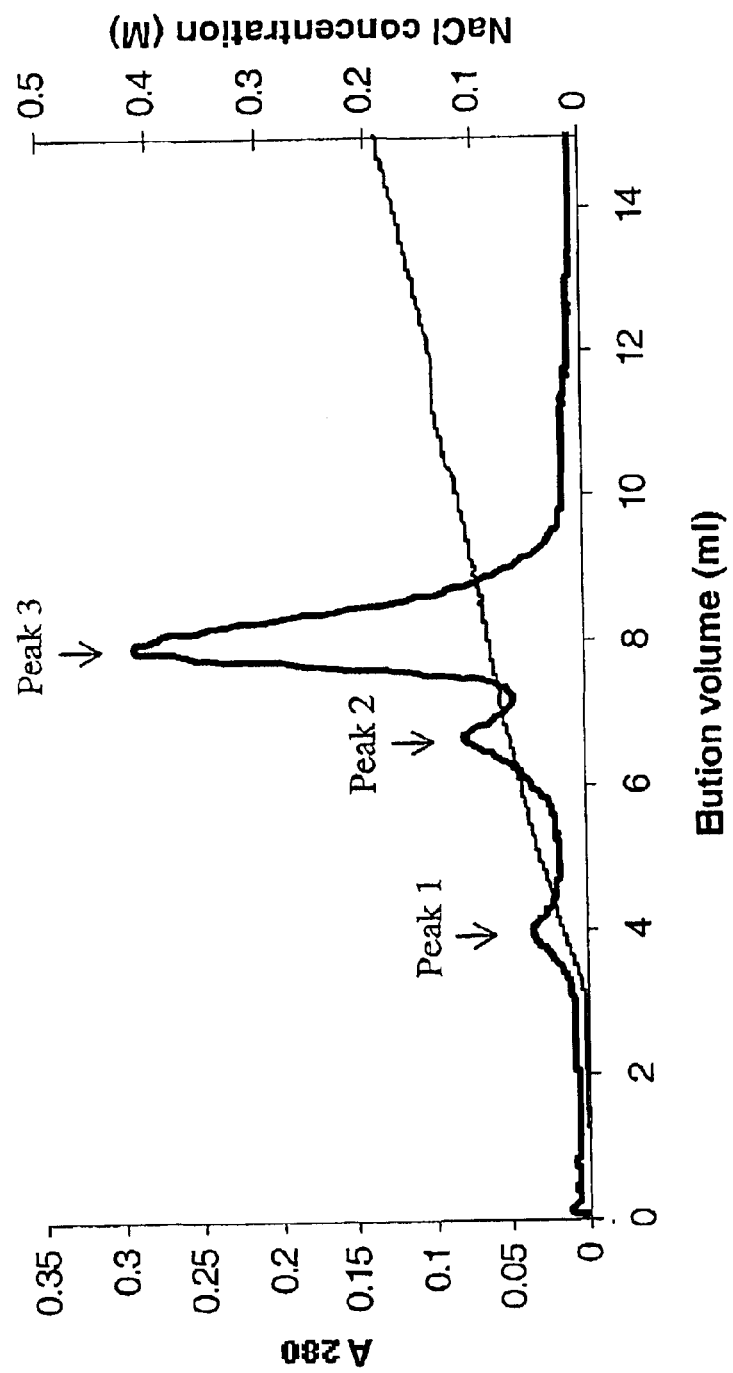
FIG. 19 shows the chromatogram (—) and the NaCl gradient (—) of the separation of the inhibitor fraction IIDon a MonoS® column at pH 6.5.

FIG. 19 shows the chromatogram (--) and the NaCl gradient (--) of the separation of the inhibitor fraction II on a MonoS® column at pH 6.5.

The two peaks resulting from inhibitor fraction I were very close together and difficult to separate on MonoS®. At pH values above 5.0, these inhibitors barely bound on the column. They had high inhibition activities against the A. niger and the B. subtilis endoxylanases. The first two peaks resulting from inhibitor fraction II had pronounced activities against both endoxylanases whereas the third one inhibited the B. subtilis endoxylanase to a much higher extent than the A. niger endoxylanase. The activity against the A. niger enzyme probably at least partially, originated from the second peak that had a small overlap with the third one. These findings suggest that, in commercial wheat flour, up to five, or even more, inhibitors occur. Based on their elution behaviour on MonoS® and their inhibition activities against the A. niger and the B. subtilis endoxylanases, the inhibitors from inhibitor fraction I and the inhibitor(s) corresponding to the third peak obtained by MonoS& at pH 6.5 of inhibitor fraction II, may correspond to what is considered TAXI I and TAXI II respectively, as described above for var. Soissons (Example 1).

Purification of Rye Endoxylanase Inhibitors

A chromatogram of the separation of the $AFC_{rye}$ material on a MonoS® column at pH 4.0 was produced. This chromatogram, combined with inhibition activity measurements and SDS-PAGE analysis of the collected fractions (gels not shown), suggested the presence of several 'TAXI'-like endoxylanase inhibitors in rye (SCXI or *Secale cereale* L. xylanase inhibitor). Four rye inhibitor fractions I–IV, were discerned.

Separations of the rye inhibitor fractions I–IV (--), (-- --), (--) (--) on MonoS® at pH 5.0 were prepared. After fractionation of the rye inhibitor fractions I–IV at least five different inhibitor peaks SCXI I–V could be distinguished.

When analysed with SDS-PAGE, all the inhibitors were structurally similar to TAXI and HVXI, as described in examples 1 and 2 (gel not shown). Furthermore, SCXI IV and V were electrophoretically pure, while SCXI I, II and III still contained some minor impurities. Because of the small differences in elution volume of these inhibitors and the similar SDS-PAGE profiles, it's possible that some of these five distinct inhibitor peaks (in particular SCXI II and III) contained more than one 'TAXI'-like inhibitor.

The different rye inhibitors, in particular SCXI IV and V, reduced the activity of the endoxylanases of A. niger, B. subtilis and T. viride to the same extent, indicating that these inhibitors have similar specificities. In contrast, the activities of TAXI I and II from wheat against the A. niger endoxylanase are clearly different, the former being a strong inhibitor of this enzyme and the latter having little if any effect on its activity. Moreover, the levels of SCXI IV and V needed to reduce the activity of the endoxylanases tested by 50%, were comparable to those needed if TAXI I and HVXI are to yield the same effect.

We can conclude that rye contains a family of endoxylanase inhibitors (with at least five members) with similar structures and specificities. These characteristics corresponds well with the properties of TAXI (I) and HVXI as described in example 1 and 2. Therefore, SCXI I–V are their rye homologues.

Some preliminary work using this approach comprising affinity chromatography with immobilised B. subtilis endoxylanase to purify endoxylanase inhibitors from durum wheat has shown promising results with 'TAXI'-like inhibitors binding selectively to the affinity column.

Purification By Affinity Chromatography with Immobilised XAN

Using the affinity column with immobilised A. niger endoxylanase and different elution conditions, we obtained two separate inhibitor fractions. The material eluted with deionised water, contained mainly proteins of about 30 kDa (SDS-PAGE), while the protein fraction eluted with the Tris/HCl buffer, consisted of 'TAXI'-like inhibitors. Determination of the N-terminal amino acid sequence of the 30 kDa proteins yielded sequences identical to those reported by Hessing and Happe [20] and McLauchlan et al [19]. Hence, the A. niger enzyme has a high selective binding affinity for the 'TAXI'-like proteins as well as for the non-'TAXI' inhibitors, present in wheat. This demonstrates that the purification of endoxylanase inhibitors using affinity chromatography with an immobilised endoxylanase is not limited to the 'TAXI'-like inhibitors.

A similar approach using affinity chromatography with immobilised endoxylanase inhibitors is expected, based on the results presented above, to be a very powerful tool for the purification of various endoxylanases (example 4).

Example 4

Isolation of an A. niger, var. Awamori Endoxylanase from a Commercial Enzyme Preparation Using Affinity Chromatography with Immobilised 'TAXI'-like Endoxylanase Inhibitors Experimental Methods Materials Enzyme preparation containing endoxylanase of A. niger, var. awamori was obtained from Quest international (Naarden, Netherlands). All other materials were as described in example 1, 2 and 3.

Endoxylanase Activity Assay Procedure

The endoxylanase activities were determined with the Xylazyme-AX method. Appropriately diluted sample (1.0 ml), containing endoxylanase and prepared in sodium acetate buffer (25 mM, pH 5.0) was incubated for 60 min at 40° C. with an AZCL-AX substrate tablet. The reaction was terminated with a 1.0% (w/w) Tris solution. The remainder of the procedure was similar to that for endoxylanase inhibition activity determination.

Protein Electrophoresis

SDS-PAGE was performed as described in the general experimental methods for examples 1 and 2.

Preparation of the Affinity Column and Endoxylanase Purification Method

The mixture of 'TAXI'-like endoxylanase inhibitors (42.0 mg) obtained after the affinity purification step, as described in example 3, were immobilised on the same carrier using a similar procedure as for the *B. subtilis* endoxylanase, as also explained in example 3.

The *A. niger*, var. awamori enzyme preparation (20.0 mg) was extracted for 30 min at room temperature with sodium acetate buffer (25 mM, pH 5.0; 5.0 ml) containing NaCl (0.2 M) and the resulting suspension was centrifuged (10000 g, 30 min, 7° C.). The supernatant was loaded on the affinity column with the immobilised endoxylanase inhibitors, equilibrated previously with the same NaCl containing acetate buffer, The proteins retained on the column were eluted with Tris buffer (250 mM, pH 8.0; 5.0 ml) and immediately neutralised with acetic acid solution(1.0 M).

Results

Most endoxylanase activity (ca. 94%) of the enzyme preparation was retained on the affinity column, presumably by interacting with the 'TAXI'-like endoxylanase inhibitors covalently linked to the matrix. After elution most of the endoxylanase activity (ca. 84%) could be recovered. The eluate comprised mainly of the endoxylanase, which has a relative molecular mass of ca. 23 kDa. Only three additional bands with lower molecular masses and of very low intensity could be observed.

Figure 20:
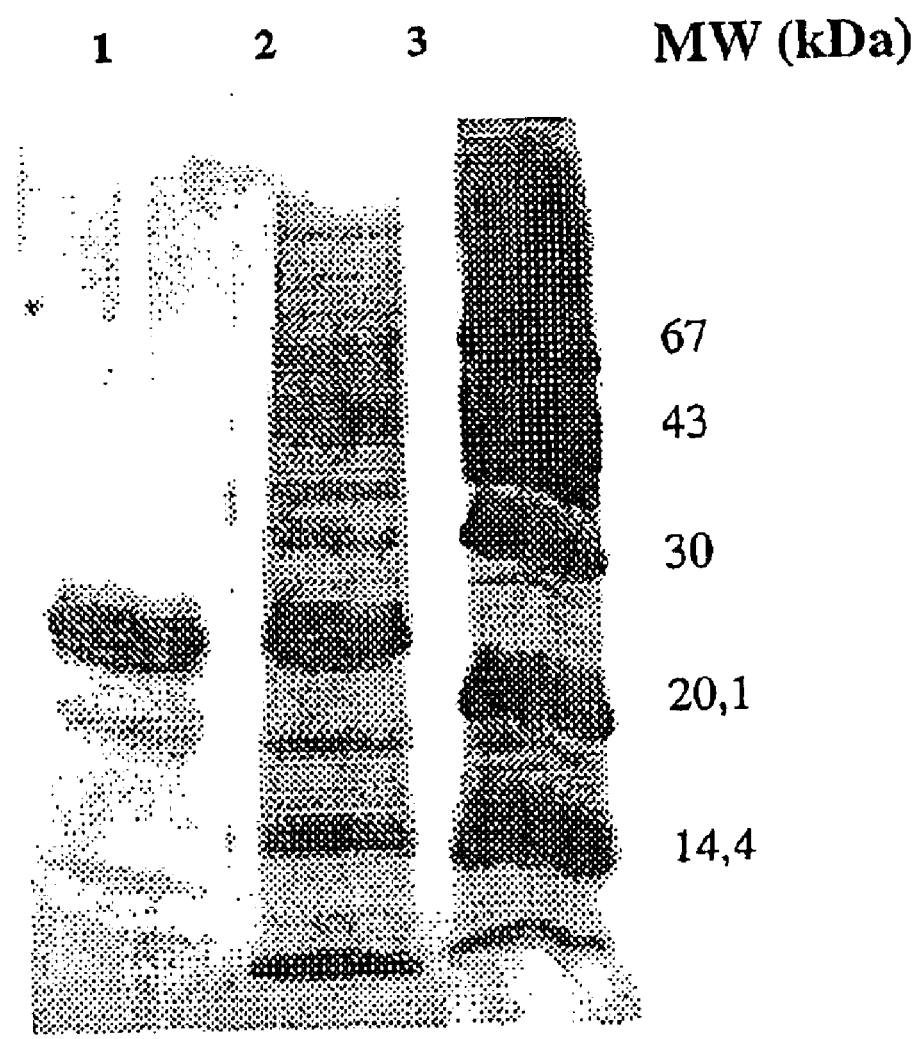
FIG. 20 shows the SDS-PAGE profiles of the fraction eluted from the affinity column (lane 1), the starting material (lane 2) and low molecular mass markers (lane 3, with the size of the markers indicated on the right).

FIG. 20 shows the SDS-PAGE profiles of the fraction eluted from the affinity column (lane 1), the starting material (lane 2) and low molecular mass markers (lane 3, with the size of the markers indicated on the right).

Example 5

Wheat Protein Encoding DNA Sequences

A BLAST search (TBLASTN 2.1.2, www.ncbi.nlm.nih.gov) in the database with non-human and non-mouse EST sequences using SEQ ID No. 1, SEQ ID No. 2, SEQ ID No. 4 and SEQ ID No. 5 (this patent application) in combination with SEQ ID No. 13, SEQ ID No. 14, SEQ ID No. 15, SEQ ID No. 16, SEQ ID No. 17, SEQ ID No. 18 and SEQ ID No. 19 as described in the patent application by Sibbesen and Sørensen [36] produced significant alignments with 5 cDNA clones of wheat:

IDENTIFIERS dbEST Id: 5493910 EST name: WWS020.H4R000101 GenBank Acc: BE420158
IDENTIFIERS dbEST Id: 5493479 EST name: WWS016.G1R000101 GenBank Acc: BE419727
IDENTIFIERS dbEST Id: 5504159 EST name: SUN002.E06R991208 GenBank Acc: BE430407
IDENTIFIERS dbEST Id: 5452003 EST name: CSB006D03F990908 GenBank Acc: BE402285
IDENTIFIERS dbEST Id: 6889613 EST name: WHE1409_B12_C23ZS GenBank Acc: BF428535

The cDNA clones were aligned with the SEQUENCHER™ programme and using SEQ ID No. 1, SEQ ID No. 2, SEQ ID No. 4 and SEQ ID No. 5 (this patent application) in combination with SEQ ID No. 13, SEQ ID No. 14, SEQ ID No. 15, SEQ ID No. 16, SEQ ID No. 17, SEQ ID No. 18 and SEQ ID No. 19 as described in the patent application by Sibbesen and Sørensen [36], the amino acid sequence of TAXI I was obtained within one reading frame. The present invention thus features a TAXI I variant having the amino acid sequence shown in SEQ ID No. 7:

LPVLAPVTKDPATSLYTIPFHDGASLVLDVAGPLVWSTCDGGQPPAEIPC

SSPTCLLANAYPAPGCPAPSCGSDKHDKPCTAYPYNPVSGACAAXSLXHT

XFVANTTDGXKPVSKVNVGVLAACAPSKLLASLPRGSTGVAGLADSGLAL

PAQVASAQKVANRFLLCLPTGGPGVAIFGGGPLPWPQFTQSMPYTPLVTK

GGSPAHYISARSIEVGDTRVPVSEGALATGGVMLSTRLPYVLLRRDVYRP

LVDAFTKALAAQHANGAPVARAVEPVAPFGVCYDTKTLGNNLGGYAVPN

VQLGLDGGSDWTMTGKNSMVDVKXGTACVAFVEMKGVAAGDGRAPAVILGG

AQMEDFVLDFDMEKKRLGFSRLPHFTGCGGL.

The present invention thus also features a TAXI I variant having the amino acid sequence shown in Seq. ID no. 8:

LPVLAPVTKDPATSLYTIPFHDGASLVLDVAGPLVWSTCDGGQPPAEIPC

SSPTCLLANAYPAPGCPAPSCGSDKHDKPCTAYPYNPVSGACAAXSLXHT

XFVANTTDGXKPVSKVNVGVLAACAPSKLLASLPRGSTGVAGLANSGLAL

PAQVASAQKVANRFLLCLPTGGPGVAIFGGGPVPWPQFTQSMPYTPLVTK

GGSPAHYISARFIEVGDTRVPVSEGALATGGVMLSTRLPYVLLRRDVYRP

LVDAFTKALAAQHANGAPVARAVEAVAPFGVLYDTKTLGNNLGGYAVPNV

QLGLDGGSDWTMTGKNSMVDVKXGTACVAFVEMKGVAAGDGRAPAVILGG

AQMEDFVLDFDMEKKRLGFSRLPHFTGCGGL.

Or the present invention features microheterogenic TAXI I variants having the amino acid sequence shown in Seq. ID no. 9:

LPVLAPVTKDPATSLYTIPFHDGASLVLDVAGPLVWSTCDGGQPPAEIPC

SSPTCLLANAYPAPGCPAPSCGSDKHDKPCTAYPYNPVSGACAAXSLXHT

XFVANTTDGXKPVSKVNVGVLAACAPSKLLASLPRGSTGVAGLAXSGLAL

PAQVASAQKVANRFLLCLPTGGPGVAIFGGGPXPWPQFTQSMPYTPLVTK

GGSPAHYISARXIEVGDTRVPVSEGALATGGVMLSTRLPYVLLRRDVYRP

LVDAFTKALAAQHANGAPVARAVEXVAPFGVXYDTKTLGNNLGGYAVPN

VQLGLDGGSDWTMTGKNSMVDVKXGTACVAFVEMKGVAAGDGRAPAVILG

GAQMEDFVLDFDMEKKR

LGFSRLPHFTGCGGL, wherein X consists of an amino acid of the group D,N,V,L,S,F,P,A and C.

Using a BLAST search (TBLASTN 2.1.2), the overall protein sequence of TAXI I shows significant homology with carrot mRNA encoding for an extracellular dermal glycoprotein (EDGP) (44%), an *Arabidopsis thaliana* putative extracellular dermal glycoprotein precursor (F15K9.16) mRNA (41%), a soybean Bg gene for a basic 7S globulin (41%) and with a *Cicer arietinum* mRNA for a putative extracellular glycoprotein (ORF1) (41%).

On the basis of the obtained nucleotide sequences of TAXI I, two other homologous cDNA clones from rice (GenBank Number: AU068900 and AU068987) were obtained from which we could determine some more upstream lying nucleotides.

From the above, the following consensus sequence of TAXI I (SEQ ID No. 10) (including ca. 95% of the coding sequence and the poly-adenylation site) was obtained:

GCCACCTCCCTCTACACAATCCCCTTCCACGACGGCGCCAGCCTCGTCCT

CGACGTCGCCGGCCCTCTCGTCTGGTCCACGTGCGATGGCGGCCAGCCGC

CCGCGGAGATCCCGTGCAGCAGCCCCACCTGCCTCCTCGCCAACGCCTAC

CCCGCCCCGGGCTGCCCCGCTCCCAGCTGCGGCAGCGATAAGCACGACAA

ACCGTGCACGGCGTACCCGTACAACCCGGTCAGCGGCGCGTGCGCCGCMK

GGAGCCTCTYCCACACGARRTTCGTGGCCAACACCACCGACGGGARYAAR

CCGGTGAGCAAGGTCAACGTCGGGGTCCTGCCGGCGTGCGCGCCGAGCAA

GCTCCTGGCGTCGCTGCCCCGGGGCTCCACGGGCGTGGCCGGGCTCGCGG

ACTCCGGCCTGGCGCTGCCGGCGCAGGTGGCGTCCGCGCAGAAGGTCGCC

AACAGGTTCCTCCTCTGCCTCCCCACCGGCGGCCCTGGCGTGGCCATCTT

CGGCGGCGGCCCCGCTCCCGTGGCCGCAATTCACGCAGTCGATGCCCTACA

CGCCGCTCGTCACCAAGGGCGGCAGCCCCGCGCACTACATCTCCGCCAGG

TCCATCGAAGTGGGGGACACCCGCGTCCCCGTATCGGAGGGCGCGCTCGC

CACCGGCGGCGTGATGCTCAGCACGAGGCTGCCCTACGTCTTGCTCCGCC

GCGACGTGTACCGCCCGTTGGTGGACGCGTTCACCAAGGCCCTGGCGGCG

CAGCATGCCAACGGAGCGCCCGTGGCGCGCGCAGTGGAGCCTGTGGCGCC

GTTCGGGGTGTGCTACGACACGAAGACGCTGGGCAACAACCTCGGCGGGT

ACGCGGTGCCCAACGTCCAGCTGGGGCTCGATGGCGGSAGTGACTGGACG

ATGACCGGGAAGAACTCGATGGTGGACGTCAAGCMRGGGACGGCGTGCGT

TGCGTTCGTGGAGATGAAGGGAGTGGCGGCCGGCGACGGCAGGGCGCCGG

CGGTGATCCTCGGAGGGCCCAGATGGAGGACTTCGTGCTCGACTTCGAC

ATGGAGAAGAAGCGGCTCGGGTTTAGCAGGCTGCCGCACTTTACGGGTTG

CGGCGGCCTGTAATAATAAATCTGTTTAACGACAGGTGGATTCGTCCACT

ACTGCGTGTAATAAATAAGGGAAGAAACACTTTTCCATCAGTGGTTTCAT.

As a next step, based on the consensus TAXI I sequence (SEQ ID No. 10) 4 primers were designed. Primer 1 is GCCACCTCCCTCTACACAATC.     (SEQ ID No.31) Primer 2 is GTAGTGGACGAATCCACCTGTC.    (SEQ ID No.32) Primer 3 is CGCAATTCACGCAGTCGATG.      (SEQ ID No.33) Primer 4 is CCCAGCGTCTTCGTGTCGTAG (SEQ ID No. 34). Primers 1 and 2 are positioned at the flanks of the sequence, while primers 3 and 4 are internal primers. Primers were ordered from Genset (Paris, France).

PCR reactions were performed in 35 µl using 0.05 Units HotStarTaq DNA Polymerase (Qiagen, Hilden ,Germany), commercially supplied buffer (Qiagen), 200 µm of each dNTP, 1 µM of each primer and 50 ng total genomic DNA as template, prepared as described [37]. The reaction mixtures were subjected to incubation for 15 min at 95° C., followed by 30 cycles of 1 min at 94° C., 90 s at 57° C., 2 min at 72° C. and a final incubation for 15 min at 72° C. on a UNO II thermocycler (Biometra, Göttingen, Germany). PCR products were cloned using the TOPO TA cloning kit for sequencing (Invitrogen, Carlsbad, Calif., USA). The ligation mixtures, composed of 1 µl PCR 4-TOPO vector, 1 µl salt solution (supplied in the kit) and 4 µl fresh PCR product, were incubated for 5 min at 20° C. Two µl of the ligation mixture was added to a vial of TOP10 One Shot Chemically Competent *E. coli* (supplied in the kit) and incubated on ice for 10 min. Subsequently, the reactions were incubated at 42° C. for 30 seconds and transferred to ice. After addition of 250 µl SOC medium (supplied in the kit) and incubation in a shaker at 37° C. for 1 hour, the transformations were spread on selective (ampicillin) agar plates and incubated overnight at 37° C.

DNA sequencing of the cloned PCR products was done using QIAprep Spin Miniprep (Qiagen) purified plasmids, vector specific primer and the BigDye Terminator Cycle Sequencing Ready Reaction Kit (Applied Biosystems, Foster City, Calif., USA). Sequencing gels were run on a 377 ABI PRISM DNA Sequencer (Applied Biosystems).

Results

Clones representing partial xylanase inhibitor sequences were obtained from PCR-amplified genomic DNA from bread wheat (*Triticum aestivum* cultivar Soissons and cultivar Estica), durum wheat (*Triticum durum* cultivar Mexicali) and the diploid wild wheat *Aegilops tauschii*. The xylanase inhibitor type I or II was identified by alignment of the encoded amino acid sequences with peptide sequences identified from native TAXI type I and II. Besides sequences related to type I and type II, a divergent sequence (called type III) was identified. From alignments with cDNA sequences it is clear that none of the cloned fragments contained introns.

Five clones are presented. The first three sequences represent type I inhibitors. The fourth sequence represents a type II inhibitor. The last sequence represents a type III inhibitor. The sequences of five cloned PCR products are as follows:

SEQ ID No. 15 is part of a xylanase inhibitor gene termed TAXI-I.01 from *Triticum aestivum* cultivar Soissons:

GCCACCTCCCTCTACACAATCCCCTTCCACGACGGCGCCAGCCTCGTCCT

CGACGTCGCCGGCCCTCTCGTCTGGTCCACGTGCGATGGCGGCCAGCCGC

CCGCGGAGATCCCGTGCAGCAGCCCCACCTGCCTCCTCGCCAACGCCTAC

CCCGCCCCGGGCTGCCCCGCGCCCAGCTGCGGCAGCAACAGGCACAACAA

GCCGTGCACGGCGTACCCGTACAACCCGGTCAGCGGCGCGTGCGCCGCAG

GGAGCCTCTCCCACACGAGATTCGTGGCCAACACCACCGACGGGAGCAAG

CCGGTGAGCAAGGTGAACGTCGGGGTCCTGGCGGCGTGCGCGCCGAGCAA

GCTCCTGGCGTCGCTGCCCCGGGGCTCCACGGGCGTGGCCGGGCTCGCGA

ACTCCGGCTTGGCGCTGCCGGCGCAGGTGGCATCCGCGCAGAAGGTCGCC

AACAGGTTCCTCCTCTGCCTCCCCACCGGCGGCCTTGGCGTGGCCATATT

TGGCGGCGGCCCCGGTCCCGTGGCCGCAATTCACGCAGTCGATGCCTTACA

CGCCGCTCGTCACCAAGGGCGGCAGCCCCGCGCACTACATCTCGGCCAGG

TCCATTGTAGTGGGGGACACCCGCGTCCCCGTATCGGAGGGCGCGCTCGC

CACCGGCGGCGTGATGCTCAGCACGAGGCTACCCTACGTCTTGCTCCGCC

CCGACGTGTACCGCCCGTTGATGGACGCGTTTACCAAGGCCCTGGCGGCG

CAGCATGCCAACGGAGCGCCCGTGGCGCGCGCAGTGGAGGCTGTGGCGCC

GTTCGGGGTGTGCTACGACACGAAGACGCTGGGCAACAACCTCGGCGGGT

ACGCGGTGCCCAACGTCCAGCTGGGGCTCGATGGCGGCAGTGACTGGACG

-continued

ATGACCGGGAAGAACTCGATGGTGGACGTCAAGCAAGGGACGGCGTGCGT

TGCGTTCGTGGAGATGAAGGGAGTGGCGGCCGGCGACGGCAGGGCGCCGG

CGGTGATCCTCGGAGGGGCCCAGATGGAGGACTTCGTGCTCGACTTCGAC

ATGGAGAAGAAGCGGCTCGGGTTTAGCAGGCTGCCGCACTTTACGGGTTG

CGGCGGCCTGTAATAATAAATCTGTTTAACGACAGGTGGATTCGTCCACT

AC.

SEQ ID No. 16 is part of a xylanase inhibitor gene termed TAXI-I.02 from *Triticum aestivum* cultivar Estica:

GCCACCTCCCTCTACACAATCCCCTTCCACCACGGCGCCAGCCTCGTCCT

CGACGTCGCCGGCCCTCTCGTCTGGTCCACGTGCGATGGCGGCCAGCCGC

CCGCGGAGATCCCGTGCAGCAGCCCCACCTGCCTCCTCGCCAACGCCTAC

CCCGCCCCGGGCTGCCCCGCTCCCAGCTGCGGCAGCGATAAGCACGACAA

ACCGTGCACGGCGTACCCGTACAACCCGGTCAGCGGCGCGTGCGCCGCAG

GGAGCCTCTCCCACACGAGATTCGTGGCCAACACCACCGACGGGAGCAAG

CCGGTGAGCAAGGTGAACGTCGGGGTCCTGGCGGCGTGCGCGCCGAGCAA

GCTCCTGGCGTCGCTGCCCCGGGGCTCCACGGGCGTGGCCGGGCTCGCGA

ACTCCGGCTTGGCGCTGCCGGCGCAGGTGGCATCCGCGCAGAAGGTCGCC

AACAGGTTCCTCCTCTGCCTCCCCACCGGCGGCCCTGGCGTGGCCATATT

TGGCGGCGGCCCGGTCCCGTGGCCGCAATTCACGCAGTCGATGCCTTACA

CGCCGCTCGTCACCAAGGGCGGCAGCCCCGCGCACTACATCTCGGCCAGG

TCCATTGTAGTGGGGGACACCCGCGTCCCCGTACCGGAGGGCGCGCTCGC

CACCGGCGGCGTGATGCTCAGCACGAGGCTACCCTACGTCTTGCTCCGCC

CCGACGTGTACCGCCCGTTGATGGACGCGTTCACCAAGGCCCTGGCGGCG

CAGCATGCCAACGGAGCGCCCGTGGCGCGCGCAGTGGAGGCTGTGGCGCC

GTTCGGGGTGTGCTACGACACGAAGACGCTGGGCAACAACCTCGGCGGGT

ACGCGGTGCCCAACGTCCAGCTGGGGCTCGATGGCGGCAGTGACTGGACG

ATGACCGGGAAGAACTCGATGGTGGACGTCAAGCAAGGGACGGCGTGCGT

TGCGTTCGTGGAGATGAAGGGAGTGGCGGCCGGCGACGGCAGGGCGCCGG

CGGTGATCCTCGGAGGGGCCCAGATGGAGGACTTCGTGCTCGACTTCGAC

ATGGAGAAGAAGCGGCTCGGGTTTAGCAGGCTGCCGCACTTTACGGGTTG

CGGCGGCCTGTAATAATAAATCTGTTTAACGACAGGTGGATTCGTCCACT

AC.

SEQ ID No. 17 is part of a xylanase inhibitor gene termed TDXI-I.01 from *Triticum durum* cultivar Mexicali:

CGCAATTCACGCAGTCGATGCCTTACACGCCGCTCGTCACCAAGGGCGGC

AGCCCCGCGCACTACATCTCGGCCAGGTCCATTGTAGTGGGGGACACCCG

CGTCCCCGCCGTATCGGAGGGCGCGCTCGCCACCGGCGGCGTGATGCTCA

GCACGAGGCTACCCTACGTCTTGCTCCGCCCCGACGTGTACCGCCCGTTG

ATGGACGCGTTCACCAAGGCCCTGGCGGCGCAGCATGCCAACGGAGCGCC

CGTGGCGCGCGCAGTGGAGGCTGTGGCGCCGTTCGGGGTGTGCTACGACA

CGAAGACGCTGGGCAACAACCTCGGCGGGTACGCGGTGCCCAACGTCCAG

CTGGGGCTCGATGGCGGCAGTGACTGGACGATGACCGGGAAGAACTCGAT

GGTGGACGTCAAGCAAGGGACGGCGTGCGTTGCGTTCGTGGAGATGAAGG

GAGTGGCGGCCGGCGACGGCAGGGCGCCGGCGGTGATCCTCGGAGGGGCC

CAGATGGAGGACTTCGTGCTCGACTTCGACATGGAGAAGAAGCGGCTCGG

GTTTAGCAGGCTGCCGCACTTTACGGGTTGCGGCGGCCTGTAATAATAAA

TCTGTTTAACGACAGGTGGATTCGTCCACTAC.

SEQ ID No. 18 is part of a xylanase inhibitor gene termed ATXI-II.01 from *Aegilops tauschii* variety Acc2220051:

GCCACCTCCCTCTACACAATCCCCTTCCACCAGGGCGCCAGCCTCGTCCT

TGACATCGCCGGCCCGCTCGTCTGGTCCACGTGCCAGCGCGGCGATCTGC

CGACAGATATCCCGTGCACTAGCCCCAGCTGCCTCCTCGCCAACGCCTAC

CCCGCCCCGGGCTGCCCCGCGCCCAGCTGCGGCAGCGGCAGCCACGACAA

GCAATGCACGACGTACCCATCCAACCCGGTCACCGGCGCGTGCGCCGCCG

GGAGCCTCGCCCGCACGACGCTCATAGCCGACACCACCGACGGGAATAAC

CCGGTGAGCCAGGTGTACGTCCGGATCCTGGCGGCGTGCGCGCCGAGAAA

GCTCCTGGCGTCGCTGCCCCGCGGCTCCATGGGCGTCGCCGGGCTAGGGG

GCTCCGGCCTGGCGCTGCCGGCGCAGGTGGCGTCCACCCAGAAGGTCGCC

AACAAGTTTCTCCTCTGCCTCCCCAGCGGCGGCCCTGGCGTGGCCATCTT

CGGCGGCGGCCCGCTCCCGTGGCCGCAATTGACGCAGTCGATGCCGTACA

CGCCGCTCGTCACCAAGGGCGGCAGCCCCGCGCACTACATCTCCGTCAAG

GCCATCCAACTGGAGGACACCCGCGTCTCCGTCTCAGAGCGCGTGCTCGC

CACCGGCGGCGTGATGCTCAGCACGAGGCTGCCCTACGCCTTGCTCCGCC

ACGACGTCTACCGCCCGTTGGTGGACGCGTTCACCAAGGCCCTGGCGGCG

CAGCCTGCCAACGGAGCGCCCGTGGCGCGCGCCGTGAAGCCTGTGGCACC

GTTCGAGCTGTGCTACGACACGAAGACGCTGGG.

SEQ ID No. 40 is part of a xylanase inhibitor gene termed TAXI-III from *Triticum aestivum* cultivar Soissons:

GCCACCTCCCTCTACACAATCCCATTCCACTACGGCGCCAACATCGTGGT

CGACACCGCCGGACCGCTCGTCTGGTCCACGTGCGCACCCGACCACCTGC

CGGCGGCGTTCCCGTGCAAGAGCGCCACCTGCAGGCTCGCGAACAAGTAC

CACGTCCCGAGCTGCAGCGAGAGCGCGGCTGACAAGCTCTGCGACCACAG

TCACAAGGTGTGCAGGGCCTTCCCGTACAACCCGGTCACCGGCGCGTGCG

CGGCCGGGGACCTGATCCACACCAGGTTCGTCGCCAACACCACCGACGGA

AAAAACCCGGTGAGCCAGGTGAACGTTCGGGCCGTGGCGGCGTGCGCGCC

AAGCAAACTCCTCGAGTCGCTGCCGCAGGGCGCCTCGGGCGTGGCGGGGC

TCGCGGGCTCCGACCTGGCGCTGCCGGCGCAGGTGGCGTCCGAGCAGAAG

GTCTCCAACAAGTTCCTCCTCTGCCTCCCTCGCGGCCTCTCAAGCGACCC

-continued

CGGCGTGGCCGTCTTCGGCGGCGGCCCGCTCCACTTCATGGCGCGGCCGG

AGAGGGACTACACGAAGGAGCTGGCCTACACGCCGCTCGTCGCCAAGAAG

GGCAACCCCGCGCACTACATCTCGATCAAGTCCATCGCCGTGGAGAGCGC

CCGCGTGCCCGTCCCGGCGCAGGCGCTCGCCACCGGTGGGCGGTGCTCT

GCACGAGGTCGCCCTTCACCCTGCTCCGCTCCGACGTGTTCCTCCCGTTG

GTGGACGCGTTCACCAAGGCCCTGGCGAAGCAGGGTGCGCAGGGCGGGCC

CGTGGCGAAAGCGGTGAAGCCCTACGCGCCGTTCCAGCTGTGCTACGACA

CGAAGACGCTGGG.

The encoded xylanase inhibitor amino acid sequences are as follows:

SEQ ID No. 19 is part of a xylanase inhibitor type I encoded by SEQ ID No. 15:

ATSLYTIPFHDGASLVLDVAGPLVWSTCDGGQPPAEIPCSSPTCLLANAY

PAPGCPAPSCGSDKHDKPCTAYPYNPVSGACAAGSLSHTRFVANTTDGSK

PVSKVNVGVLAACAPSKLLASLPRGSTGVAGLANSGLALPAQVASAQKVA

NRFLLCLPTGGLGVAIFGGGPVPWPQFTQSMPYTPLVTKGGSPAHYISAR

SIVVGDTRVPVPEGALATGGVMLSTRLPYVLLRPDVYRPLMDAFTKALAA

QHANGAPVARAVEAVAPFGVCYDTKTLGNNLGGYAVPNVQLGLDGGSDWT

MTGKNSMVDVKQGTACVAFVEMKGVAAGDGRAPAVILGGAQMEDFVLDFD

MEKKRLGFSRLPHFTGCGGL.

SEQ ID No. 20 is part of a xylanase inhibitor type I encoded by SEQ ID No. 16:

ATSLYTIPFHDGASLVLDVAGPLVWSTCDGGQPPAEIPCSSPTCLLANAY

PAPGCPAPSCGSNRHNKPCTAYPYNPVSGACAAGSLSHTRFVANTTDGSK

PVSKVNVGVLAACAPSKLLASLPRGSTGVAGLANSGLALPAQVASAQKVA

NRFLLCLPTGGLGVAIFGGGPVPWPQFTQSMPYTPLVTKGGSPAHYISAR

SIVVGDTRVPVSEGALATGGVMLSTRLPYVLLRPDVYRPLMDAFTKALAA

QHANGAPVARAVEAVAPFGVCYDTKTLGNNLGGYAVPNVQLGLDGGSDWT

MTGKNSMVDVKQGTACVAFVEMKGVAAGDGRAPAVILGGAQMEDFVLDFD

MEKKRLGFSRLPHFTGCGGL.

SEQ ID No. 21 is part of a xylanase inhibitor type I encoded by SEQ ID No. 17:

QFTQSMPYTPLVTKGGSPAHYISARSIVVGDTRVPAVSEGALATGGVMLS

TRLPYVLLRPDVYRPLMDAFTKALAAQHANGAPVARAVEAVAPFGVCYDT

KTLGNNLGGYAVPNVQLGLDGGSDWTMTGKNSMVDVKQGTACVAFVEMKG

VAAGDGRAPAVILGGAQMEDFVLDFDMEKKRLGFSRLPHFTGCGGL.

SEQ ID No. 22 is part of a xylanase inhibitor type II encoded by SEQ ID No. 18:

ATSFYTIPFHQGASLVLDIAGPLVWSTCQRGDLPTDIPCSSPTCLLANAY

PAPGCPAPSCGSGSHDKQCTTYPSNPVTGACAAGSLARTTLIADTTDGNN

PVSQVYVRILAACAPRKLLASLPRGSMGVAGLGGSGLALPAQVASTQKVA

NKFLLCLPSGGPGVAIFGGGPLPWPQLTQSMPYTPLVTKGGSPAHYISVK

AIQLEDTRVSVSERVLATGGVMLSTRLPYALLRHDVYRPLVDAFTKALAA

QPANGAPVARAVKPVAPFELCYDTKTL.

SEQ ID No. 41 is part of a xylanase inhibitor type III encoded by SEQ ID No. 40:

ATSLYTIPFHYGANIVVDTAGPLVWSTCAPDHLPAAFPCKSATCRLANKY

HVPSCSESAADKLCDHSHKVCRAFPYNPVTGACAAGDLIHTRFVANTTDG

KNPVSQVNVRAVAACAPSKLLESLPQGASGVAGLAGSDLALPAQVASEQK

VSNKFLLCLPRGLSSDPGVAVFGGGPLHFMARPERDYTKELAYTPLVAKK

GNPAHYISIKSIAVESARVPVPAQALATGGAVLCTRSPFTLLRSDVFLPL

VDAFTKALAKQGAQGGPVAKAVKPYAPFQLCYDTKTL.

Example 6

Rye Protein Encoding DNA Sequences

PCR was also performed on genomic DNA from rye (*Secale cereale* cultivar Halo) using primers 3 (SEQ ID No. 33) and 4 (SEQ ID No. 34) according to the procedures as descibed above. Two clones are presented. The sequences of two cloned PCR products are as follows:

SEQ ID No. 23 is an internal fragment of a xylanase inhibitor gene termed SCXI-01 from *Secale cereale* cultivar Halo:

CGCAATTCACGCAGTCGATGCAGTACACGCCGCTCGTCACCAAGGGCGGC

AGCCCCGCGCACTACATCTCGCTGAAGTCCATCAAAGTGGACAACACCGG

CGTCACCGTCTCGCAGAGCGCGTTCGCCACCGGCGGCGTGATGCTGAGCA

CGAGGCTGCCCTACGCCCTGCTCCGCCGCGACGTGTACCGCCCGTTGGTG

GACGCGTTCACCAAGGCCCTGGCGGCGCAGCCTGCCAACGGAGCGCCCGT

GGCGCGCGCAGTGCAGCCCGTGGCGCCGTTCGGGGTGTGCTACGACACGA

AGACGCTGGG

SEQ ID No. 24 is an internal fragment of a xylanase inhibitor gene termed SCXI-02 from *Secale cereale* cultivar Halo:

CGCAATTCACGCAGTCGATGCAGTACACGCCGCTCGTCACCAAGGGCGGC

AGCCCCGCGCACTACATCTCGCTCAAGTCCATCAAAGTGGACAACACCGG

CGTCACCCTCTCGCAGAGCGCGCTCGCCACCGGCGGCGTGATGCTCAGCA

CGAGGCTGCCCTACGCCCTGCTCCGCAGCGACGTGTACCGCCCGTTGGTG

GACGCGTTCACCAAGGCCCTGGCGGCGCAGCCTGTCAACGGAGCGCCCGT

GGCGCGCGCGGTGAAGCCCGTGGAGCCGTTCGGGGTGTGCTACGACACGA

AGACGCTGGG

The encoded xylanase inhibitor amino acid sequences are as follows:

SEQ ID No. 25 is part of a xylanase inhibitor encoded by SEQ ID No. 23:

QFTQSMQYTPLVTKGGSPAHYISSLKSIKVDNTGVTVSQSAFATGGVMLST

RLPYALLRRDVYRPLVDAFTKALAAQPANGAPVARAVQPVAPFGVCYDT

KTL.

SEQ ID No. 26 is part of a xylanase inhibitor encoded by SEQ ID No. 24:

QFTQSMQYTPLVTKGGSPAHYISSLKSIKVDNTGVTVSQSAFATGGVMLST

RLPYALLRRDVYRPLVDAFTKALAAQPANGAPVARAVQPVAPFGVCYDT

KTL.

Example 7

Rice Protein Encoding DNA Sequences

A FASTA3 search in the EMBL ESTs library using SEQ ID No. 15 (this patent application) produced significant alignment with two non-overlapping cDNA clones of rice with accession numbers D15808 and C26221. The cDNA sequence D15808 shows an overlap with the 5' part (152 nt) of SEQ ID No. 15 (this patent application). The cDNA sequence C26221 overlaps internally with SEQ ID No. 15. Based on these rice cDNA sequences, primers 5 and 6 were designed. Primer 5 is GCGGCGACCTCGCTCTACAC (SEQ ID No. 35). Primer 6 is TGTACGGGTACGCCGTGCA (SEQ ID No. 36). These primers were used to amplify a DNA fragment from rice genomic DNA using the procedure described above. A clean PCR product was directly sequenced using the individual PCR primers as sequencing primers. The sequence is as follows:

SEQ ID No. 27 is part of a xylanase inhibitor gene termed OSXI-01 from *Oryza sativa*:

GCGGCGACCTCGCTCTACACCATCCCCGTCAGGTACTACGACAACCTCGT

CGTCGACCTCGCCGGCCCGCTCGTCTGGTCGACGTGCGCCGCCGACCACC

TGCCGGCGTCGCTGTCCTGCCAGGACCCGACGTGCGTGGTCGCCAACGCG

TACCGTGCTCCGACCTGCAAGGTCACCGGCGGCGGCGGCGACTGCAGCAA

GAACGTGTGCACGGCGTACCCGTACA.

SEQ ID No. 28 is part of a xylanase inhibitor protein encoded by SEQ ID No. 27:

AATSLYTIPVRYYDNLVVDLAGGPLVWSSTCAADHLPASLSCCQDPTCV

VANAYRAPTCKVTGGGDCSKNVCTAYPY.

Example 8

Maize Protein Encoding DNA Sequences

Primers 1 and 6 were also used to amplify a DNA fragment from *Zea mays* genomic DNA using identical procedures as described. A clean PCR product was directly sequenced using the individual PCR primers as sequencing primers. The sequence is as follows:

SEQ ID No. 29 is part of a xylanase inhibitor gene termed ZMXI-01 from *Zea mays*:

GCCACCTCCCTCTACACAATCCCCTTCCACGACGGCGCCAGCCTCGTCCT

CGACGTCGCCGGCCCGCTCGTCTGGTCCACGTGCCAGCGCGGCGATCTGC

CGACAGATATCCCGTGCAGTAGCCCCACCTGCCTCCTCGCCAACGCCTAC

CCCGCCCCGGGCTGCCCCGCGCCCAGCTGCGGCAGCGACAGGCACGACAA

GCCGTGCACGGCGTACCCGTACA.

SEQ ID No. 30 is part of a xylanase inhibitor protein encoded by SEQ ID No. 29:

ATSLYTIPFHDGASLVLDVAGPLVWSTCQRGDLPTDIPCSSPTCLLANAY

PAPGCPAPSCGSDRHDKPCTAYPY.

Example 9

Barley Protein Encoding DNA Sequences

A BLAST search (TBLASTX 2.1.2, www.ncbi.nlm.nih.gov) in the database with non-human and non-mouse EST sequences using SEQ ID No. 6 (this patent application) produced significant alignment with a cDNA clone of barley:

IDENTIFIERS dbEST Id:5811794 EST name: HVSMEh0101D07f

GenBank Acc: BE602955

The present invention thus features a part of a HVXI variant having the amino acid sequence shown in SEQ ID No. 11:

AGFAGSGLALPAQVASAQKVSHRFLLCLPTGGAGVAILGGGPLPWPQFTQ

SMAYTPLVGKQGSPAHYVSGTXIKVEDTRVPVPDRALVTGGVMLNTKLAY

VLLRRDVYRPVVDAFTKALAAQHANGAPAARAVDPVAPFGLCYDAKTLGN

NLGGYSVPNVVLALDGGGEWAMTGKNSMVDVKPGX.

The present invention thus also features a part of a HVXI variant having the amino acid sequence shown in SEQ ID No. 12:

AGFAGSGLALPAQVASAQKVSHRFLLCLPTGGAGVAILGGGPLPWPQFTQ

SMAYTPLVGKQGSPAHYVSGTXIKVEDTRVPVPDRALVTGGVMLNTKLAY

VLLRRDVYRPVVDAFTKALAAQHANGALAARGVNPVAPFGLCYDAKTNGN

NLGGYSVPNVVLALDGGGEWAMTGKNSMVDVKPGX.

Or the present invention features a part of microheterogenic HVXI variants having the amino acid sequence shown in SEQ ID No. 13:

AGFAGSGLALPAQVASAQKVSHRFLLCLPTGGAGVAILGGGPLPWPQFTQ

SMAYTPLVGKQGSPAHYVSGTXIKVEDTRVPVPDRALVTGGVMLNTKLAY

VLLRRDVYRPVVDAFTKALAAQHANGAXAARXVXPVAPFGLCYDAKTXGN

NLGGYSVPNVVLALDGGGEWAMTGKNSMVDVKP

GX, wherein X consists of an amino acid of the group P,A,D,L,G,N and C.

The obtained consensus sequence of HVXI (SEQ ID No. 14): (including ca. 48% of the coding sequence) is as follows:

GCGGGCTTCGCGGGCTCCGGCCTGGCGCTGCCGGCGCAGGTGGCGTCCGC

GCAGAAGGTCTCCCATCGGTTCCTCCTCTGCCTCCCCACGGGCGGCGCCG

GCGTGGCCATCCTCGGCGGCGGCCCGCTCCCGTGGCCGCAGTTCACGCAG

TCCATGGCCTACACCCCGCTCGTCGGCAAGCAAGGCAGCCCCGCGCACTA

CGTCTCGGGCACGTNCATCAAAGTCGAGGACACCCGCGTTCCCGTTCCGG

ACCGCGCGCTCGTCACCGGGGGGTGATGCTCAACACGAAGCTGGCCTAC

GTCTTGCTCCGCCGCGACGTGTACCGCCCGGTGGTGGACGCGTTCACCAA

GGCCCTGGCGGCGCAGCATGCCAACGGAGCGCCCGCGGCGCGCGCCGTGG

ACCCCGTGGCGCCGTTCGGGCTGTGCTACGACGCCAAGACGCTGGGCAAC

AACCTCGGCGGGTACTCGGTGCCCAACGTGGTGCTGGCGCTCGACGGCGG

GGGTGAATGGGCGATGACCGGGAAGAACTCGATGGTGGACGTCAAGCCGG

GGA.

Example 10

Oat Protein Encoding DNA Sequences

Based on IDENTIFIERS dbEST Id: 5811794 EST name: HVSMEh0101D07f GenBank Acc: BE602955, primers 9 and 10 were designed. Primer 9 is TGGCGTCCGCGCA-GAAGGTC (SEQ ID No. 44). Primer 10 is GCT-TGACGTCCACCATCGAG (SEQ ID No. 45). These primers were used to amplify a DNA fragment from oat genomic DNA. The resulting PCR product was cloned according to procedures described above. The sequence is as follows:

SEQ ID No. 42 is part of a xylanase inhibitor gene termed ASXI-01 from *Avena sativa*:

TGGCGTCCGCGCAGAAGGTCGCCAAGAAGTTCCTCCTCTGCCTCTCCCGC

GGCGGCGTGTACGGAGACGGCGTGGCCATCTTCGGCGGCGGCCCGCTCCA

CCTCACCGCGCAGCCGGAGACAGACTACACGCAGTCCCTTGAGTACACGC

CGCTCTTCACCAAAGAAGGCAACCCGGCGTACTACGTCTCGGTCAAGTCC

ATCGCGCTGGAGAACACCCCCGTCCCCGTCTCGACCCGCACGCTCGACGC

CGGCGGTGTGGTGCTCTGCACCAGGGTGCCATACACCTTTCTCCGCCCCG

ACGTGTACCTCCCGTTCGCGGACGCGTTCCGCACGGCAATGAAGGCGCAG

AAGGCGCAAGAAATGAAGGCCGTGGCGCCATTCGGGCTGTGCTACAACAC

GTCGACGCTGGCCAACACGCGGCTCGGGTACCTGGTGCCGACCGTGACGC

TGGCGCTGGAAGGCGGGAAGAAGTGGACGATGACGGGCGTCCACTCGATG

GTGGACGTCAAGC.

The encoded xylanase inhibitor amino acid sequence is as follows:
SEQ ID No. 43 is part of a xylanase inhibitor encoded by SEQ ID No. 42:

ASAQKVAKKFLLCLSRGGVYGDGVAIFGGGPLHLTAQPETDYTQSLEYTP

LFTKEGNPAYYVSVKSIALENTPVPVSTRTLDAGGVVLCTRVPYTFLRPD

VYLPFADAFRTAMKAQKAQEMKAVAPFGLCYNTSTLANTRLGYLVPTVTL

ALEGGKKWTMTGVHSMVDVK.

Example 11

Recombinant Expression of Xylanase Inhibitors
Materials and Methods
Materials, Strains and Media The TOPO TA Cloning Kit for Sequencing and the pBAD/TOPO ThioFusion Expression System were obtained from Invitrogen (Carlsbad, Calif., USA). The pMAL Protein Fusion and purification system was purchased from New England Biolabs (Beverly, Mass., USA). The pHOS31 vector was derived from the pHEN1 plasmid [38] by insertion of the phage lambda cos site and a restriction site for I-SceI into the AatII site.

The following *E.coli* strains were used: TOP10 (genotype : F⁻ mcrA Δ(mmr-hsdRMS-mcrBC) Φ80lacZΔM15 ΔlacX74 recA1 deoR araD139 Δ(ara-leu) 7697 galU galK rpsL (Str$^R$) endA1 nupG) (Invitrogen) and XL1-Blue MRF' (genotype: Δ(mrcA)183Δ(mcrCB-hsdSMR-mmr)173 endA1 supE44 thi-1 recA1 gyrA96 relA1 lac [F' proAB lacI$^q$ ZΔM15 Tn10(Tet$^r$)]) (Stratagene, La Jolla, Calif., USA). *E.coli* strain TG1 (genotype: supE hsdΔ5 thi Δ(lac-proAB) [F' traD36 proAB lacI$^q$ lac ZΔM15]) was used for expression experiments.

The LB-Amp medium (11) had the following composition: 10 g Tryptone Peptone (Difco), 5 g Selected Yeast Extract (Gibco BRL), 10 g NaCl (Acros Organics) and 100 μg/ml filter sterilised ampicillin. For agar medium, 15 g Select Agar (Gibco BRL) was added. One liter 2×TYA contained 16 g Tryptone Peptone, 10 g Selected Yeast Extract, 5 g NaCl and 100 μg/μl filter sterilised ampicillin. In 2×TYAG medium is 2×TYA supplemented with 2% glucose.

Construction of the Expression Plasmids

The PCR 4-TOPO vector (Invitrogen) containing part of a xylanase inhibitor gene from *Triticum aestivum* cultivar Estica (example 5) was used as template for the construction of expression plasmids. Based on the sequence (SEQ ID No. 16), 2 primers were designed.

Forward primer 7 (SEQ ID No. 37) is CCAAGATCTCT-GCCAGTTCTGGCACCTGTGACCAAA-GATCCAGCAACCTCCCTCTACAC Reverse primer 8 (SEQ ID No. 38) is CCTAGATCTTTA-CAGGCCGCCGCAACCCGTAAAG.

Both primers are positioned at the flanks of the sequence and contain at their 5' end a BglII restriction site (underlined) plus 3 extra 5' nucleotides. The forward primer (SEQ ID No. 37) contains a 3' end corresponding to 5' end of SEQ ID No. 16, plus a designed sequence encoding the N-terminal amino acids from mature TAXI (bold) as revealed by N-terminal sequencing of the native protein (SEQ ID No. 1) and missing from the genomic sequence (SEQ ID No. 16). The reverse primer (SEQ ID No. 38) contains a 3' end complementary to the 3' end of the TAXI coding sequence including a stop codon (bold). Primers were ordered from Genset (Paris, France).

PCR reactions were performed in 50 μl using 0.05 U of HotStarTaq DNA polymerase (Qiagen, Hilden, Germany), commercially supplied buffer (Qiagen), 200 μM of each DNTP, 1 μM of each primer and 200 ng of plasmid DNA. DNA amplification was carried out in an Eppendorf Mastercycler gradient (Hamburg, Germany) through an incubation step (15 min at 95° C.), followed by 25 cycles of denaturation (1 min at 94° C.), annealing (90 s at 57° C.) and extension (2 min at 72° C.). An additional extension step (20 min at 72° C.) was added.

The resulting PCR product was purified using the QIAquick PCR Purification Kit (Qiagen) and directly cloned into the pBAD/TOPO ThioFusion expression vector. The ligation mixture, containing 1 μl pBAD/Thio-TOPO vector (supplied in the kit), 3 μl MilliQ water and 2 μl purified PCR product, was incubated during 5 min at room temperature. The mixture was then placed on ice. Three μl of the ligation mixture was added to a vial of TOP10 One Shot Chemically Competent E.coli (supplied in the kit) previously mixed with 2 μl of 0.5M β-mercaptoethanol, and incubated during 30 min on ice. Subsequently, the cells were incubated during 30 s at 42° C. and placed immediately back on ice. After addition of 250 μl SOC medium (supplied in the kit) and incubation in a shaker at 37° C., the transformed cells were plated on a selective (ampicillin) agar plate. Colonies were grown in liquid medium. Plasmid DNA of the resulting pBAD/Thio-TAXI transformants was isolated using the QIAprep Spin Miniprep Kit (Qiagen). Insertions were verified by digestion with NruI and by DNA sequencing using vector specific primers and the BigDye Terminator Cycle Sequencing Ready Reaction Kit (Applied Biosystems, Calif., USA). Sequencing gel was run on a 377 ABI PRISM DNA Sequencer (Applied Biosystems).

In a second step, the pBAD/Thio-TAXI vector was used as DNA source for the construction of two other expression plasmids, pHOS31-TAXI and pMAL-p2X-TAXI, respectively. Therefore, the inserted TAXI gene was cut out of the pBAD/Thio-TAXI vector with BglII. The vector was simultaneously digested with PvuI to prevent self ligation and unwanted insertion in the other expression plasmids. The obtained restriction fragments were subsequently ligated overnight into a BglII cut, dephosphorylated pHOS31 vector, or a BamHI cut, dephosphorylated pMal-p2X plasmid. The ligation mixtures were transformed to electroporation competent XL1-Blue MRF' E.coli cells. The transformation mixture was spread on selective (ampicillin) agar plates. Positive clones were confirmed by restriction analysis with NruI/ BamIE in the case of the pHOS31-TAXI constructs and with ApaI for the pMAL-p2X-TAXI constructs. The pMAL-p2X-TAXI construct is deposited with the Belgian Coordinated Collection of Microorganisms under access number LMBP 4268.

Recombinant Expression of TAXI from pBAD/Thio-TAXI

E.coli TOP10 cells containing the pBAD/Thio-TAXI vector were analysed for the expression of recombinant thioredoxin-TAXI fusion protein. An aliquot (100 μl) of an overnight grown culture was inoculated in 5 ml LB-Amp medium. The cultures were grown to mid-exponential phase ($OD_{600nm}$~0.5) at 37° C. in a shaker. Expression was induced by addition of 50 μl of a 2% arabinose solution. Cells were incubated at 37° C. for another 4 hours. An aliquot (1 ml) was taken for SDS-PAGE analysis. Cells were pelleted and resuspended in 75 μl MilliQ water. The remaining cells were pelleted, resuspended in 2.5 ml lysis buffer (50 mM $NaH_2PO_4$, 300 mM NaCl, 10 mM imidazole, pH8) and incubated during 30 min on ice. Following 3 freeze-thaw cycles (at −70° C. and room temperature), cells were sonicated on ice during 15 s. The resulting cleared lysate was used for measuring the endoxylanase inhibition activity.

Recombinant Expression of TAXI from pHOS31-TAXI and pMAL-p2x-TAXI

Vectors, pHOS31-TAXI and pMAL-p2x-TAXI, and the corresponding parental plasmids were separately transformed into E. coli TG1 cells. Individual colonies were picked up, inoculated into 5 ml of 2×TYAG and grown overnight at 37° C. in a shaker. Subsequently, 500 μl of the overnight grown cultures was inoculated into 50 ml fresh 2×TYAG medium. Cell cultures were grown at 37° C. until an $OD_{600nm}$ of ~0.6. Then, the cells were pelleted and resuspended in 50 ml 2×TYA with 1 mM IPTG. After 4 hours of incubation at 30° C. in a shaker, the cells were harvested. The periplasmic protein fraction was isolated by cold osmotic shock. Therefore, cells were resuspended in 5 ml 30 mM Tris-HCl, 20% sucrose, pH8. Following addition of 500 μl of a 10 mM EDTA solution, the cells were shaken at room temperature during 10 min. Subsequently, the cells were pelleted at 4° C., resuspended in 5 ml icecold 5 mM $MgSO_4$ and placed on ice during 10 min while shaking. The cell suspensions were centrifuged and the resulting supernatants were used for SDS-PAGE analysis and measurement of endoxylanase inhibition activity.

Protein Analysis

SDS-PAGE was performed with the Mini-PROTEAN II cell system (Biorad, USA) according to the manufacturer's instructions. Gels were stained with the SimplyBlue SafeStain following the basic protocol (Invitrogen, USA).

The endoxylanase inhibition activities were determined as described in the general experimental methods for examples 1 and 2. As little as 250 μl of an endoxylanase solution was added to an equal amount of sample. In the case of the pBAD/Thio-TAXI lysate, 50 μl of 0.5M AcOH was added to obtain a pH of about 5. The periplasmic protein fractions were used as such. The reaction was terminated by adding 2% Tris solution (5 ml) in stead of 10 ml of 1% Tris.

Purification of the Recombinant MBP-TAXI Fusion Protein

Affinity chromatography was done to purify the MBP-TAXI fusion protein according to the method described in example 3. However, A. niger var. awamori endoxylanase purified as discussed in example 4 in stead of B. subtilis endoxylanase was immobilised. An aliquot (5 ml) of the periplasmic protein fraction of the pMAL-p2X-TAXI cells together with 800 μl protease inhibitor cocktail (1 Complete tablet (Boehringer Mannheim, Germany) and 400 μl pepstatin (5 mM in ethanol) in 4 ml 200 mM NaAc pH5 with 1.5M NaCl) was brought onto the column. Elution of MBP-TAXI was achieved with Tris buffer (250 mM) of pH8 in stead of pH10.

Results

Construction of the pBAD/Thio-TAXI Vector and Expression in E. coli

The PCR product, containing the complete coding sequence for a mature endoxylanase inhibitor protein from wheat and 2 additional BglII restriction sites at the flanks, was cloned in frame in a pBAD/Thio-TOPO vector under the control of the PBAD promoter. DNA analysis of a retained clone revealed that there were 2 silent mutations.

The TAXI encoding DNA sequence, the flanking BglII restriction sites (bold) and the stop codon of the retained clone are represented in SEQ ID No. 39:

```
CCAAGATCTTTGCCAGTTCTGGCACCTGTGACCAAAGATCCAGCAACCTC

CCTCTACACAATCCCCTTCCACGACGGCGCCAGCCTCGTCCTCGACGTCGCCGGCC

CTCTCGTCTGGTCCACGTGCGATGGCGGCCAGCCGCCCGCGGAGATCCCGTGCAGC

AGCCCCACCTGCCTCCTCGCCAACGCCTACCCCGCCCCGGGCTGCCCCGCTCCCAG

CTGCGGCAGCGATAAGCACGACAAACCGTGCACGGCGTACCCGTACAACCCGGTCA

GCGGCGCGTGCGCCGCAGGGAGCCTCTCCCACACGAGATTCGTGGCCAACACCACC

GACGGGAGCAAGCCGGTGAGCAAGGTGAACGTCGGGGTCCTGGCAGCGTGCGCGCC

GAGCAAGCTCCTAGCGTCGCTGCCCCGGGGCTCCACGGGCGTGGCCGGGCTCGCGA

ACTCCGGCTTGGCGCTGCCGGCGCAGGTGGCATCCGCGCAGAAGGTCGCCAACAGG

TTCCTCCTCTGCCTCCCCACCGGCGGCCCTGGCGTGGCCATATTTGGCGGCGGCCC

GGTCCCGTGGCCGCAATTCACGCAGTCGATGCCTTACACGCCGCTCGTCACCAAGG

GCGGCAGCCCCGCGCACTACATCTCGGCCAGGTCCATTGTAGTGGGGGACACCCGC

GTCCCCGTACCGGAGGGCGCGCTCGCCACCGGCGGCGTGATGCTCAGCACGAGGCT

ACCCTACGTCTTGCTCCGCCCCGACGTGTACCGCCCGTTGATGGACGCGTTCACCA

AGGCCCTGGCGGCGCAGCATGCCAACGGAGCGCCCGTGGCGCGCGCAGTGGAGGCT

GTGGCGCCGTTCGGGGTGTGCTACGACACGAAGACGCTGGGCAACAACCTCGGCGG

GTACGCGGTGCCCAACGTCCAGCTGGGGCTCGATGGCGGCAGTGACTGGACGATGA

CCGGGAAGAACTCGATGGTGGACGTCAAGCAAGGGACCGGGTGCGTTGCGTTCGTG

GAGATGAAGGGAGTGGCGGCCGGCGACGGCAGGGCGCCGGCGGTGATCCTCGGAGG

GGCCCAGATGGAGGACTTCGTGCTCGACTTCGACATGGAGAAGAAGCGGCTCGGGT

TTAGCAGGCTGCCGCACTTTACGGGTTGCGGCGGCCTGTAAAGATCTCCG.
```

FIG. 21 shows the nucleotide and amino acid sequences of the PCR product. The nucleotides corresponding to TAXI SEQ ID No. 16 are indicated with a line above. The primers, containing a BglII restriction site (underlined), are represented in bold. The forward primer contains nucleotide sequences complementary to the 5' end of SEQ ID No. 16 and the N-terminal amino acids from mature TAXI missing from the genomic sequence. The reverse primer contains nucleotide sequences complementary to the 3' end of SEQ ID No. 16 and a stop codon. The TAXI amino acids are in italic.

FIG. 22 shows the insertion of the PCR product in the pBAD/Thio-TOPO vector. The enterokinase recognition site and 3 C-terminal amino acids of the thioredoxin protein are also indicated.

Induction of the pBAD promoter is expected to lead to the cytoplasmic expression of a thioredoxin-TAXI fusion protein of about 55.7 kDa. SDS-PAGE analysis of the total protein fraction of the cells transformed with pBAD/Thio-TAXI showed that there was a prominent protein band of about 55.7 kDa. This protein was absent in the protein fraction of the cells containing empty pBAD/Thio vector.

FIG. 23 A represents the recombinant thioredoxin-TAXI fusion protein.

Figure 24:
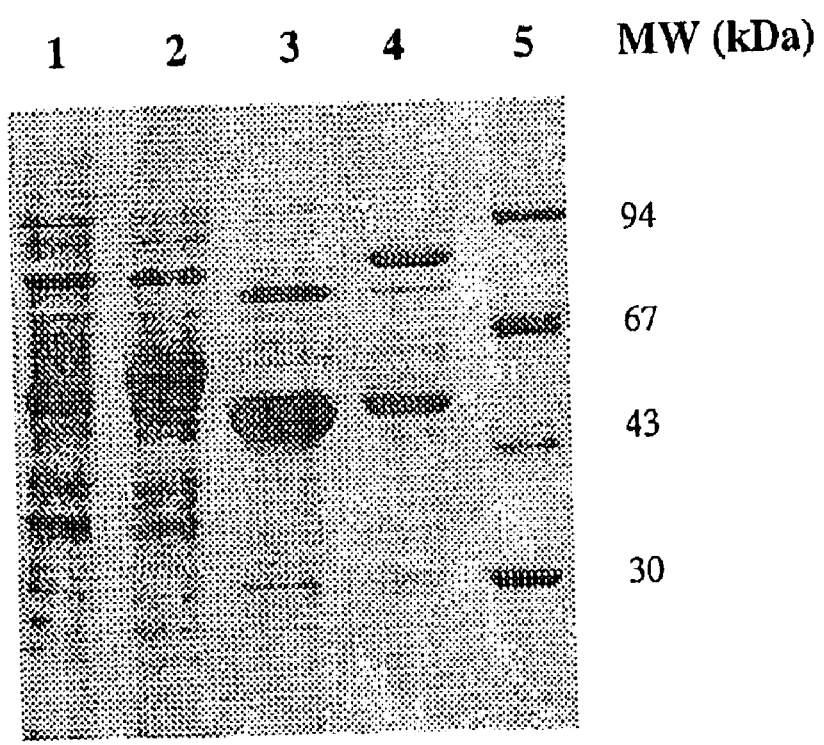
FIG. 24 shows the SDS-PAGE profiles of the total cell extracts of the pBAD/Thio cells and the pBAD/Thio-TAXI cells (lanes 1 and 2 respectively). The low molecular mass markers are situated in lane 5. The size of the markers is indicated on the right.

FIG. 24 shows the SDS-PAGE profiles of the total cell extracts of the pBAD/Thio cells and the pBAD/Thio-TAXI cells (lanes 1 and 2 respectively). The low molecular mass markers are situated in lane 5. The size of the markers is indicated on the right.

Total cell lysates were used to measure the endoxylanase inhibition activity against *Bacillus subtilis* endoxylanase. No endoxylanase inhibition activity was measured in the extract containing the thioredoxin-TAXI fusion protein and the control containing thioredoxin. It appeared that the thioredoxin-TAXI producing cells contained large inclusion bodies, as seen by phase contrast microscopy, suggesting improper folding and aggregation of the recombinant protein.

Construction of the pHOS31-TAXI and the pMAL-p2X-TAXI Vectors and Expression in TG1 *E.coli*

The TAXI gene (SEQ ID No. 39) was cut out the pBAD/Thio-TAXI vector with the flanking BglII restriction sites and cloned in frame into a pHOS31 and a pMAL-p2X vector.

The pHOS31 and the pMAL-p2X vector are under the control of respectively a $P_{lacz}$ promoter and a $P_{tac}$ promoter and can be induced by adding IPTG. The presence of the pelB leader sequence and the malE signal sequence in respectively pHOS31 and pMAL-p2X, allow fusion proteins to be exported to the periplasm. In the case of the pHOS31-TAXI vector, a ca. 40 kDa TAXI protein will be expressed. The pMAL-p2X-TAXI construct leads to a MBP (maltose binding protein)-TAXI fusion protein of about 82 kDA. Both plasmids, pHOS31-TAXI and pMAL-p2X-TAXI, and the corresponding parental plasmids, were seperately transformed to *E.coli* TG1 cells to perform the expression experiments.

FIGS. 25 and 26 show the insertion of the BglII cut PCR product in respectively the BglII and the BamHI restriction site of respectively the pHOS31 vector and the pMAL-p2X vector. The C-terminal amino acids of the pelB leader sequence respectively the malE signal sequence together with the 'linker' amino acids are also represented.

FIG. 23 B shows the recombinant TAXI protein as expressed by the pHOS31-TAXI plasmid.

FIG. 23 C shows the recombinant MBP-TAXI protein as expressed by the pMAL-p2X-TAXI plasmid.

SDS-PAGE analysis of the periplasmic fractions of pHOS31-TAXI showed no clear TAXI protein band. However, the ca. 82 kDa MBP-TAXI fusion protein was prominent.

FIG. 24 shows the SDS-PAGE profiles of the periplasmic protein extract with the ca. 82 kDa MBP-TAXI fusion protein or the ca. 50.8 kDa MBP control protein (lanes 4 and 3 respectively). The molecular mass markers are in lane 5 and represented on the right.

The periplasmic protein fractions of the pHOS31-TAXI and the pMAL-p2X-TAXI *E. coli* cells were used to measure the endoxylanase inhibition activity against *A. niger* and *B. subtilis* endoxylanase. Both the pHOS31-TAXI fraction and the pMAL-p2X-TAXI fraction showed endoxylanase inhibition activity against *A. niger* (96% and 99%, respectively) and *B. subtilis* (81% and 88%, respectively) endoxylanase. This indicates that a recombinant TAXI I protein was produced.

Purification of Recombinant MBP-TAXI Fusion Protein

SDS-PAGE analysis showed that the ca. 82 kDa MBP-TAXI fusion protein was efficiently purified from the periplasmic protein fraction by affinity chromatography on immobilised *A.niger* endoxylanases. The recombinant TAXI protein has molecular form A as under reducing conditions no dissociation of the protein was noticed.

Figure 27:
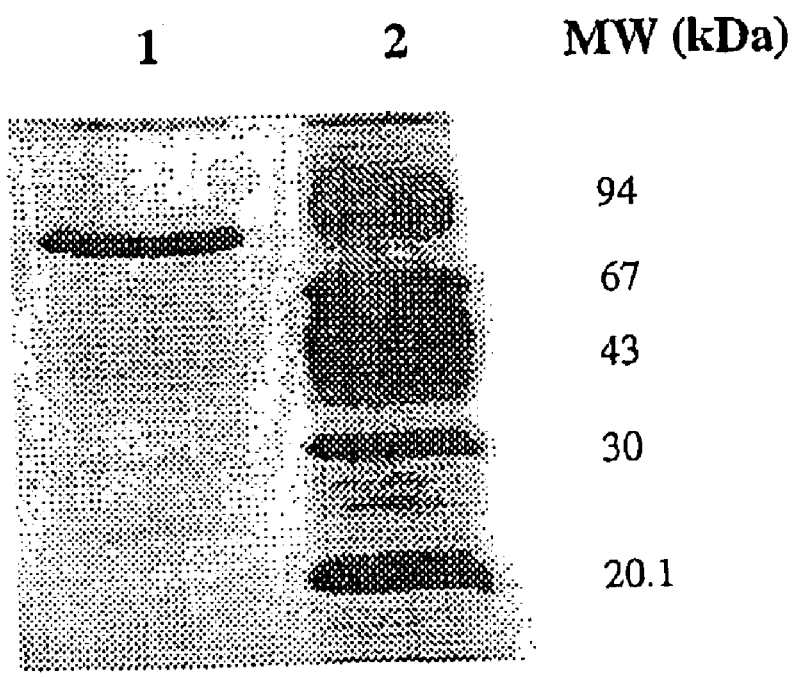
FIG. 27 shows the SDS-PAGE profile of the ca. 82 kDa purified MBP-TAXI fusion protein (lane 1). The molecular mass markers are in lane 2 and indicated on the right.

FIG. 27 shows the SDS-PAGE profile of the ca. 82 kDa purified MBP-TAXI fusion protein (lane 1). The molecular mass markers are in lane 2 and indicated on the right.

Demonstration of endoxylanase inhibition activity by extracts from *E. coli* harboring the recombinant TAXI sequences was the final proof that the gene sequences identified do encode the inhibitor activity. The cloned gene can be efficiently expressed in *E. coli* into active form when secreted into the periplasm with or without a fusion protein. TAXI produced in the cytoplasm appeared inactive, most probably due to failure of accurate disulphide bond formation and/or folding into the native state. Recombinant TAXI is active as a single chain (form A) protein.

General Conclusion

As exemplified, two general methods can be used for the purification of endoxylanase inhibitors from wheat flour, and barley whole meal. Very likely, they are both also applicable for rye, durum wheat and a broad spectrum of other plant sources.

A first method comprises several (four) separations on cation exchange columns and one separation on a gel filtration column to obtain pure inhibitor. A second method comprises two purification steps, one with cation exchange chromatography and another with affinity chromatography, to obtain a pure inhibitor sample containing one or more endoxylanase inhibitors. These inhibitors can at least partially be separated from one another by further fractionations with high resolution cation exchange chromatography. This second approach to purify endoxylanase inhibitors is a highly efficient purification method since using said method we could isolate inhibitor proteins from wheat, rye and barley with large structural similarity (e.g. amino acid sequence and SDS-PAGE profile) and similarity in activity pattern as described above, as well as other endoxylanase inhibitor proteins.

In the case of wheat flour (var. Soissons) two endoxylanase inhibitors, TAXI I and TAXI II, could be purified with the first purification method and were partially characterised. Depending on the immobilised endoxylanase and the elution conditions, the second purification method allowed for the isolation of at least five inhibitors (TAXI) as well as for the isolation of other xylanase inhibitors (non-TAXI) from commercially available wheat flour (likely a mixture of different wheat varieties).

In the case of barley whole meal (var. Hiro) one endoxylanase inhibitor, HVXI, could be purified with the first purification method and was partially characterised. However, we have indications that at least one additional endoxylanase inhibitor may be present in barley as well. Using the second method, the purification of HVXI was also successful.

In the case of rye flour (var. Halor) the second purification method resulted in several endoxylanase inhibitors (SCXI I–V), with highly similar specificities and characteristics.

The wheat, barley and rye endoxylanase inhibitors under consideration are all characterised by similar molecular masses (ca. 40.0 kDa) and structures. They occur in two different forms, i.e. proteolytically modified ones and non-modified ones. The modified forms dissociate in two polypeptides (ca. 30.0 and ca. 10.0 kDa) upon reduction with β-mercaptoethanol. Neither of the inhibitors are glycosylated. TAXI I has a pI of 8.8 where as TAXI II and HVXI have pI values of 9.3 or higher. The N-terminal amino acid sequences of these three inhibitors show a high degree of mutual identity, especially those of the ca. 40.0 kDa polypeptides, and are not described as such for proteins of other sources.

Despite the difference in pI, TAXI I and HVXI, have similar effects on the five endoxylanases mentioned above. In contrast to TAXI I and HVXI, TAXI II has only little if any inhibition activity against the *A. niger* endoxylanase, but it similarly affects the other four endoxylanases.

Studies on the inhibition type of TAXI I and TAXI II unexpectedly show that the type of inhibition depends on the endoxylanase used. The *A. niger* endoxylanase is inhibited by TAXI I by blocking the active site, i.e. TAXI I competes with arabinoxylan, and in the case of the *B. subtilis* endoxylanase, both TAXI I or TAXI II and arabinoxylan can bind and this independent of the binding order, i.e. TAXI I and TAXI II do not compete with arabinoxylan. Because of their similar endoxylanase inhibition profiles, it is not unreasonable to assume that HVXI inhibits the *A. niger* and *B. subtilis* endoxylanases in a manner analogous to that of TAXI I.

We also document for the first time a new technique for the purification of endoxylanases from commercially available enzyme preparations based on affinity chromatography with an immobilised cocktail of 'TAXI'-like endoxylanase-inhibitors.

Furthermore, the invention features not only amino acid sequences of endoxylanase inhibitors, but also corresponding encoding polynucleotide sequences and variants, homologues or fragments thereof.

A TAXI gene was cloned and recombinant active TAXI proteins including a fusion protein were produced by *E. coli*.

References

1 Fincher, G. B. and Stone, B. A. (1993) Barley: Chemistry and Technology (MacGregor, A. W. and Bhatty, R. S., eds.), pp 247–296, American Association of Cereal Chemists, Inc., Saint Paul, Minn., USA 2 Enari, T. M. and Sopanen, T. (1986) J. Inst. Brew. 92, 25–31

3 MacGregor, A. W. and Fincher, G. B. (1993) Barley: Chemistry and Technology (MacGregor, A. W. and Bhatty, R. S., eds.), pp 73–130, American Association of Cereal Chemists, Inc., Saint Paul, Minn., USA 4 Voragen, A. G. J., Schols, H. A., Marijs, J., Rombouts, F. M. and Angelino, S. A. G. F. (1987) J. Inst. Brew. 93, 202–208
5 Deponte, R., Parlamenti, R., Petrucci, V., Silano, V. and Tomasi, M. (1976) Cereal Chem. 53, 805–820
6 Garcia-Casada, G., Sanchez-Monge, R., Lopez-Otin, C. and Salcedo, G. (1994) Eur. J. Biochem. 224, 525–531
7 Pace, P., Parlamenti, R., Rab, A., Silano, V. and Vittozzi, L. (1978) Cereal Chem. 55, 244–254
8 Silano, V. (1987) Enzymes and their Role in Cereal Technology (Kruger, J. E., Lineback, D. and Stauffer, C. E., eds.), pp 141–199, American Association of Cereal Chemists, Inc., Saint Paul, Minn., USA
9 Taufel, A., Behnke, U., Emmer, I. and Gabor, R. (1991) Z. Lebensm. Unters. Forsch. 193, 9–14
10 Galleschi, L., Bottari, A., Capocchi, A., Repiccioli, R. and Daviozzi, F. (1997) Sci. Aliment. 17, 173–182
11 Ievleva, E. V., Rudenskaya, Y. A., Zimacheva, A. V. and Masalov, V. V. (1995) Biochem. Moscow 60, 1237–1240
12 Jones, B. L. and Morinac, L. A. (1997) J. Am. Soc. Brew. Chem. 55, 58–64
13 Mundy, J., Hejgaard, J. and Svendsen, I. (1984) FEBS Lett. 167, 210–214
14 Debyser, W. and Delcour, J. A. (1997) Inhibitors of xylanolytic and β-glucanolytic enzymes, European patent filed April 1997, further mather added April 1998, published as WO 98/49278
15 Debyser, W., Derdelinckx, G. and Delcour, J. A. (1997) J. Am. Soc. Brew. Chem. 55, 153–156
16 Debyser, W. (1999) Arabinoxylan solubilisation during the production of Belgian white beer and a novel class of wheat proteins that inhibit endoxylanases, PhD dissertation, Katholieke Universiteit Leuven, Belgium
17 Debyser, W., Peumans, W. J., Van Damme, E. J. M. and Delcour, J. A. (1999) J. Cereal Sci. 30, 39–43
18 Rouau, X. and Surget, A. (1998) J. Cereal Sci. 28, 63–70
19 McLauchlan, W. R., Garcia-Conesa, M. T., Williamson, G., Roza, M., Ravestein, P. and Maat, J. Biochem. J. 338, 441–446
20 Hessing, M. and Happe, R. P. (2000) A novel class of xylanase inhibitors, European patent filed August 1998, published as EP 0979830 A1
21 Bradford, M. M. (1976) Anal. Biochem. 72, 248–254
22 Cleemput, G., Hessing, M., van Oort, M., Deconynck, M. and Delcour, J. A. (1997a) Plant Physiol. 113, 377–386
23 Laemmli, U. K. (1970) Nature 227, 680–685
24 Roels, S. P. and Delcour, J. A. (1996) J. Cereal Sci. 24, 227–239
25 Somogyi, M. (1960) Clinical Chemistry 6, 23–35
26 Altschul, S. F., Madden, J. L., Schaffer, A. A., Zhang, J., Zhang, Z., Miller, W. and Lipman, D. J. (1997) Nucleic Acid Res. 25, 3389–3402
27 Peuyo, J. J., Hunt, D. C. and Chrispeels, M. J. (1993) Plant Physiol. 101, 1341–1348
28 Santino, A., Daminati, M. G., Vitale, A. and Bollini R. (1992) Physiol. Plant 85, 425–432
29 Søorensen, J. F. and Poulsen, C. H. (1999) Endogenous xylanase inhibitor from wheat flour: Its characteristics and influence on xylanases used in bakery applications, AACC Annual Meeting, Seattle.
30 Cleemput, G. (1996) Characterisation of water-extractable non-starch polysaccharides and non-starch polysaccharide hydrolysing enzymes in European wheat flours, PhD dissertation, Katholieke Universiteit Leuven, Belgium
31 Cleemput, G., Van Laere, K., Hessing, M., Van Leuven, F., Torrekens, S. and Delcour, J. A. (1997b) Plant Physiol. 115, 1619–1627
32 Garcia-Olmedo, F., Salcedo, G., Sanchez-Monge, R., Gomez, L., Royo, J. and Carbonero, P. (1987) Oxf. Surv. Plant. Mol. Cell. Biol. 4, 275–334
33 Slade, A. M., Høy, P. B., Morrice, N. A. and Fincher, G. B. (1989) Eur. J. Biochem. 185, 533–539
34 Banik, M., Li, C. -D., Langridge, P. and Fincher, G. B. (1997) Mol. Gen. Genet. 253, 599–608
35 Benjavongkulchai, E. and Spencer, M. S. (1989) Can. J. Bot. 67, 297–302
36 Sibbesen, O., Sorensen, J. F. Proteins. International patent application, published as WO 00/39289.
37 Van Campenhout, S., Vander Stappen, J., Sagi, L., Volckaert, G. (1995) Theor. Appl. Genet. 91, 313–319.
38 Hoogenboom, H. R., Griffiths, A. D., Johnson, K. S., Chiswell, D. J., Hudson, P. and Winter, G. (1991) Nucleic Acids Res. 19, 4133–4137

SEQUENCE LISTING

```
<160> NUMBER OF SEQ ID NOS: 45
<210> SEQ ID NO 1
<211> LENGTH: 24
<212> TYPE: PRT
<213> ORGANISM: Triticum aestivum
<220> FEATURE:
<221> NAME/KEY: PEPTIDE
<222> LOCATION: (1)..(24)
<223> OTHER INFORMATION: N-terminal amino acid sequence of a ca. 40 kDa
      xylanase inhibitor (TAXI I), wherein the first Xaa  is preferably
      Leu and the second Xaa is preferably Leu
<220> FEATURE:
<221> NAME/KEY: MISC_FEATURE
<222> LOCATION: (21)..(21)
<223> OTHER INFORMATION: unknown, possibly Leu
<220> FEATURE:
<221> NAME/KEY: MISC_FEATURE
<222> LOCATION: (23)..(23)
<223> OTHER INFORMATION: unknown, possibly Leu

<400> SEQUENCE: 1
```

```
Leu Pro Val Leu Ala Pro Val Thr Lys Asp Pro Ala Thr Ser Leu Tyr
1               5                   10                  15

Thr Ile Pro Phe Xaa Asp Xaa Ala
            20
```

```
<210> SEQ ID NO 2
<211> LENGTH: 22
<212> TYPE: PRT
<213> ORGANISM: Triticum aestivum
<220> FEATURE:
<221> NAME/KEY: PEPTIDE
<222> LOCATION: (1)..(22)
<223> OTHER INFORMATION: N-terminal amino acid sequence of a ca. 40 kDa
      xylanase inhibitor (TAXI II)

<400> SEQUENCE: 2

Leu Gly Leu Pro Val Leu Ala Pro Val Thr Lys Asp Thr Ala Thr Ser
1               5                   10                  15

Leu Tyr Thr Ile Pro Phe
            20
```

```
<210> SEQ ID NO 3
<211> LENGTH: 22
<212> TYPE: PRT
<213> ORGANISM: Hordeum vulgare
<220> FEATURE:
<221> NAME/KEY: PEPTIDE
<222> LOCATION: (1)..(22)
<223> OTHER INFORMATION: N-terminal amino acid sequence of a ca. 40 kDa
      xylanase inhibitor (HVXI), wherein the first Xaa is preferably
      Pro and the second Xaa is preferably Phe
<220> FEATURE:
<221> NAME/KEY: MISC_FEATURE
<222> LOCATION: (21)..(21)
<223> OTHER INFORMATION: unknown, possibly Pro
<220> FEATURE:
<221> NAME/KEY: MISC_FEATURE
<222> LOCATION: (22)..(22)
<223> OTHER INFORMATION: unknown, possibly Phe

<400> SEQUENCE: 3

Lys Ala Leu Pro Val Leu Ala Pro Val Thr Lys Asp Ala Ala Thr Ser
1               5                   10                  15

Leu Tyr Thr Ile Xaa Xaa
            20
```

```
<210> SEQ ID NO 4
<211> LENGTH: 20
<212> TYPE: PRT
<213> ORGANISM: Triticum aestivum
<220> FEATURE:
<221> NAME/KEY: PEPTIDE
<222> LOCATION: (1)..(20)
<223> OTHER INFORMATION: internal amino acid sequence of a xylanase
      inhibitor (TAXI I), wherein Xaa is preferably Leu
<220> FEATURE:
<221> NAME/KEY: MISC_FEATURE
<222> LOCATION: (17)..(17)
<223> OTHER INFORMATION: unknown, possibly Leu

<400> SEQUENCE: 4

Gly Ala Pro Val Ala Arg Ala Val Glu Ala Val Ala Pro Phe Gly Val
1               5                   10                  15

Xaa Tyr Asp Thr
            20
```

```
<210> SEQ ID NO 5
<211> LENGTH: 25
```

```
<212> TYPE: PRT
<213> ORGANISM: Triticum aestivum
<220> FEATURE:
<221> NAME/KEY: PEPTIDE
<222> LOCATION: (1)..(25)
<223> OTHER INFORMATION: internal amino acid sequence of a xylanase
      inhibitor (TAXI II), wherein the first Xaa is preferably Leu and
      the second Xaa is
      preferably Asp
<220> FEATURE:
<221> NAME/KEY: MISC_FEATURE
<222> LOCATION: (17)..(17)
<223> OTHER INFORMATION: unknown, possibly Leu
<220> FEATURE:
<221> NAME/KEY: MISC_FEATURE
<222> LOCATION: (19)..(19)
<223> OTHER INFORMATION: unknown, possibly Asp

<400> SEQUENCE: 5

Gly Ala Pro Val Ala Arg Ala Val Ile Pro Val Ala Pro Phe Glu Leu
1               5                   10                  15

Xaa Tyr Xaa Thr Lys Ser Leu Gly Asn
            20                  25

<210> SEQ ID NO 6
<211> LENGTH: 24
<212> TYPE: PRT
<213> ORGANISM: Hordeum vulgare
<220> FEATURE:
<221> NAME/KEY: PEPTIDE
<222> LOCATION: (1)..(24)
<223> OTHER INFORMATION: internal amino acid sequence of a xylanase
      inhibitor (HVXI), wherein the first Xaa is unknown, the second
      Xaa is preferably Leu, the third and the fourth  Xaa are unknown,
      the fifth Xaa is preferably Asn and the sixth Xaa is preferably
      Gly
<220> FEATURE:
<221> NAME/KEY: MISC_FEATURE
<222> LOCATION: (6)..(6)
<223> OTHER INFORMATION: unknown
<220> FEATURE:
<221> NAME/KEY: MISC_FEATURE
<222> LOCATION: (16)..(16)
<223> OTHER INFORMATION: unknown, possibly Leu
<220> FEATURE:
<221> NAME/KEY: MISC_FEATURE
<222> LOCATION: (17)..(17)
<223> OTHER INFORMATION: unknown
<220> FEATURE:
<221> NAME/KEY: MISC_FEATURE
<222> LOCATION: (21)..(21)
<223> OTHER INFORMATION: unknown
<220> FEATURE:
<221> NAME/KEY: MISC_FEATURE
<222> LOCATION: (23)..(23)
<223> OTHER INFORMATION: unknown, possibly Asn
<220> FEATURE:
<221> NAME/KEY: MISC_FEATURE
<222> LOCATION: (24)..(24)
<223> OTHER INFORMATION: unknown, possibly Gly

<400> SEQUENCE: 6

Gly Ala Leu Ala Ala Xaa Gly Val Asn Pro Val Ala Pro Phe Gly Xaa
1               5                   10                  15

Xaa Tyr Asp Ala Xaa Thr Xaa Xaa
            20

<210> SEQ ID NO 7
<211> LENGTH: 381
<212> TYPE: PRT
<213> ORGANISM: Triticum aestivum
<220> FEATURE:
<221> NAME/KEY: PEPTIDE
```

-continued

```
<222> LOCATION: (1)..(381)
<223> OTHER INFORMATION: xylanase inhibitor, a TAXI I variant, wherein
      Xaa is preferably Gln (derived from EST-sequences)
<220> FEATURE:
<221> NAME/KEY: MISC_FEATURE
<222> LOCATION: (95)..(95)
<223> OTHER INFORMATION: unknown, possibly Gly
<220> FEATURE:
<221> NAME/KEY: MISC_FEATURE
<222> LOCATION: (98)..(98)
<223> OTHER INFORMATION: unknown, possibly Ser
<220> FEATURE:
<221> NAME/KEY: MISC_FEATURE
<222> LOCATION: (101)..(101)
<223> OTHER INFORMATION: unknown, possibly Arg
<220> FEATURE:
<221> NAME/KEY: MISC_FEATURE
<222> LOCATION: (110)..(110)
<223> OTHER INFORMATION: unknown, possibly Ser
<220> FEATURE:
<221> NAME/KEY: MISC_FEATURE
<222> LOCATION: (323)..(323)
<223> OTHER INFORMATION: unknown, possibly Gln

<400> SEQUENCE: 7
```

| | | | | | | | | | | | | | | |
|---|---|---|---|---|---|---|---|---|---|---|---|---|---|---|
| Leu | Pro | Val | Leu | Ala | Pro | Val | Thr | Lys | Asp | Pro | Ala | Thr | Ser | Leu | Tyr |
| 1 | | | | 5 | | | | | 10 | | | | | 15 | |
| Thr | Ile | Pro | Phe | His | Asp | Gly | Ala | Ser | Leu | Val | Leu | Asp | Val | Ala | Gly |
| | | | | 20 | | | | | 25 | | | | | 30 | |
| Pro | Leu | Val | Trp | Ser | Thr | Cys | Asp | Gly | Gly | Gln | Pro | Pro | Ala | Glu | Ile |
| | | | | 35 | | | | | 40 | | | | | 45 | |
| Pro | Cys | Ser | Ser | Pro | Thr | Cys | Leu | Leu | Ala | Asn | Ala | Tyr | Pro | Ala | Pro |
| | 50 | | | | | 55 | | | | | 60 | | | | |
| Gly | Cys | Pro | Ala | Pro | Ser | Cys | Gly | Ser | Asp | Lys | His | Asp | Lys | Pro | Cys |
| 65 | | | | | 70 | | | | | 75 | | | | | 80 |
| Thr | Ala | Tyr | Pro | Tyr | Asn | Pro | Val | Ser | Gly | Ala | Cys | Ala | Ala | Xaa | Ser |
| | | | | 85 | | | | | 90 | | | | | 95 | |
| Leu | Xaa | His | Thr | Xaa | Phe | Val | Ala | Asn | Thr | Thr | Asp | Gly | Xaa | Lys | Pro |
| | | | | 100 | | | | | 105 | | | | | 110 | |
| Val | Ser | Lys | Val | Asn | Val | Gly | Val | Leu | Ala | Ala | Cys | Ala | Pro | Ser | Lys |
| | | | | 115 | | | | | 120 | | | | | 125 | |
| Leu | Leu | Ala | Ser | Leu | Pro | Arg | Gly | Ser | Thr | Gly | Val | Ala | Gly | Leu | Ala |
| | 130 | | | | | 135 | | | | | 140 | | | | |
| Asp | Ser | Gly | Leu | Ala | Leu | Pro | Ala | Gln | Val | Ala | Ser | Ala | Gln | Lys | Val |
| 145 | | | | | 150 | | | | | 155 | | | | | 160 |
| Ala | Asn | Arg | Phe | Leu | Leu | Cys | Leu | Pro | Thr | Gly | Pro | Gly | Val | Ala | |
| | | | | 165 | | | | | 170 | | | | | 175 | |
| Ile | Phe | Gly | Gly | Gly | Pro | Leu | Pro | Trp | Pro | Gln | Phe | Thr | Gln | Ser | Met |
| | | | | 180 | | | | | 185 | | | | | 190 | |
| Pro | Tyr | Thr | Pro | Leu | Val | Thr | Lys | Gly | Gly | Ser | Pro | Ala | His | Tyr | Ile |
| | | | | 195 | | | | | 200 | | | | | 205 | |
| Ser | Ala | Arg | Ser | Ile | Glu | Val | Gly | Asp | Thr | Arg | Val | Pro | Val | Ser | Glu |
| | 210 | | | | | 215 | | | | | 220 | | | | |
| Gly | Ala | Leu | Ala | Thr | Gly | Gly | Val | Met | Leu | Ser | Thr | Arg | Leu | Pro | Tyr |
| 225 | | | | | 230 | | | | | 235 | | | | | 240 |
| Val | Leu | Arg | Arg | Asp | Val | Tyr | Arg | Pro | Leu | Val | Asp | Ala | Phe | Thr | |
| | | | | 245 | | | | | 250 | | | | | 255 | |
| Lys | Ala | Leu | Ala | Ala | Gln | His | Ala | Asn | Gly | Ala | Pro | Val | Ala | Arg | Ala |
| | | | | 260 | | | | | 265 | | | | | 270 | |
| Val | Glu | Pro | Val | Ala | Pro | Phe | Gly | Val | Cys | Tyr | Asp | Thr | Lys | Thr | Leu |
| | | | | 275 | | | | | 280 | | | | | 285 | |

-continued

```
Gly Asn Asn Leu Gly Gly Tyr Ala Val Pro Asn Val Gln Leu Gly Leu
        290                 295                 300

Asp Gly Gly Ser Asp Trp Thr Met Thr Gly Lys Asn Ser Met Val Asp
305                 310                 315                 320

Val Lys Xaa Gly Thr Ala Cys Val Ala Phe Val Glu Met Lys Gly Val
                325                 330                 335

Ala Ala Gly Asp Gly Arg Ala Pro Ala Val Ile Leu Gly Gly Ala Gln
            340                 345                 350

Met Glu Asp Phe Val Leu Asp Phe Asp Met Glu Lys Lys Arg Leu Gly
        355                 360                 365

Phe Ser Arg Leu Pro His Phe Thr Gly Cys Gly Gly Leu
    370                 375                 380

<210> SEQ ID NO 8
<211> LENGTH: 381
<212> TYPE: PRT
<213> ORGANISM: Triticum aestivum
<220> FEATURE:
<221> NAME/KEY: VARIANT
<222> LOCATION: (1)..(381)
<223> OTHER INFORMATION: variant of SEQ ID NO 7
<220> FEATURE:
<221> NAME/KEY: MISC_FEATURE
<222> LOCATION: (95)..(95)
<223> OTHER INFORMATION: unknown, possibly Gly
<220> FEATURE:
<221> NAME/KEY: MISC_FEATURE
<222> LOCATION: (98)..(98)
<223> OTHER INFORMATION: unknown, possibly Ser
<220> FEATURE:
<221> NAME/KEY: MISC_FEATURE
<222> LOCATION: (101)..(101)
<223> OTHER INFORMATION: unknown, possibly Arg
<220> FEATURE:
<221> NAME/KEY: MISC_FEATURE
<222> LOCATION: (110)..(110)
<223> OTHER INFORMATION: unknown, possibly Ser
<220> FEATURE:
<221> NAME/KEY: MISC_FEATURE
<222> LOCATION: (323)..(323)
<223> OTHER INFORMATION: unknown, possibly  Gln

<400> SEQUENCE: 8

Leu Pro Val Leu Ala Pro Val Thr Lys Asp Pro Ala Thr Ser Leu Tyr
1               5                   10                  15

Thr Ile Pro Phe His Asp Gly Ala Ser Leu Val Leu Asp Val Ala Gly
            20                  25                  30

Pro Leu Val Trp Ser Thr Cys Asp Gly Gly Gln Pro Pro Ala Glu Ile
        35                  40                  45

Pro Cys Ser Ser Pro Thr Cys Leu Leu Ala Asn Ala Tyr Pro Ala Pro
    50                  55                  60

Gly Cys Pro Ala Pro Ser Cys Gly Ser Asp Lys His Asp Lys Pro Cys
65                  70                  75                  80

Thr Ala Tyr Pro Tyr Asn Pro Val Ser Gly Ala Cys Ala Ala Xaa Ser
                85                  90                  95

Leu Xaa His Thr Xaa Phe Val Ala Asn Thr Thr Asp Gly Xaa Lys Pro
            100                 105                 110

Val Ser Lys Val Asn Val Gly Val Leu Ala Ala Cys Ala Pro Ser Lys
        115                 120                 125

Leu Leu Ala Ser Leu Pro Arg Gly Ser Thr Gly Val Ala Gly Leu Ala
    130                 135                 140

Asn Ser Gly Leu Ala Leu Pro Ala Gln Val Ala Ser Ala Gln Lys Val
```

-continued

```
               145                 150                 155                 160
       Ala Asn Arg Phe Leu Leu Cys Leu Pro Thr Gly Gly Pro Gly Val Ala
                       165                 170                 175

Ile Phe Gly Gly Gly Pro Val Pro Trp Pro Gln Phe Thr Gln Ser Met
                       180                 185                 190

Pro Tyr Thr Pro Leu Val Thr Lys Gly Gly Ser Pro Ala His Tyr Ile
                       195                 200                 205

Ser Ala Arg Phe Ile Glu Val Gly Asp Thr Arg Val Pro Val Ser Glu
                       210                 215                 220

Gly Ala Leu Ala Thr Gly Gly Val Met Leu Ser Thr Arg Leu Pro Tyr
       225                 230                 235                 240

Val Leu Arg Arg Asp Val Tyr Arg Pro Leu Val Asp Ala Phe Thr
                       245                 250                 255

Lys Ala Leu Ala Ala Gln His Ala Asn Gly Ala Pro Val Ala Arg Ala
                       260                 265                 270

Val Glu Ala Val Ala Pro Phe Gly Val Leu Tyr Asp Thr Lys Thr Leu
                       275                 280                 285

Gly Asn Asn Leu Gly Gly Tyr Ala Val Pro Asn Val Gln Leu Gly Leu
       290                 295                 300

Asp Gly Gly Ser Asp Trp Thr Met Thr Gly Lys Asn Ser Met Val Asp
       305                 310                 315                 320

Val Lys Xaa Gly Thr Ala Cys Val Ala Phe Val Glu Met Lys Gly Val
                       325                 330                 335

Ala Ala Gly Asp Gly Arg Ala Pro Ala Val Ile Leu Gly Gly Ala Gln
                       340                 345                 350

Met Glu Asp Phe Val Leu Asp Phe Asp Met Glu Lys Lys Arg Leu Gly
                       355                 360                 365

Phe Ser Arg Leu Pro His Phe Thr Gly Cys Gly Gly Leu
                       370                 375                 380

<210> SEQ ID NO 9
<211> LENGTH: 381
<212> TYPE: PRT
<213> ORGANISM: Triticum aestivum
<220> FEATURE:
<221> NAME/KEY: VARIANT
<222> LOCATION: (1)..(381)
<223> OTHER INFORMATION: variant of SEQ ID NO 7
<220> FEATURE:
<221> NAME/KEY: MISC_FEATURE
<222> LOCATION: (95)..(95)
<223> OTHER INFORMATION: unknown, possibly Gly
<220> FEATURE:
<221> NAME/KEY: MISC_FEATURE
<222> LOCATION: (98)..(98)
<223> OTHER INFORMATION: unknown, possibly Ser
<220> FEATURE:
<221> NAME/KEY: MISC_FEATURE
<222> LOCATION: (101)..(101)
<223> OTHER INFORMATION: unknown, possibly Arg
<220> FEATURE:
<221> NAME/KEY: MISC_FEATURE
<222> LOCATION: (110)..(110)
<223> OTHER INFORMATION: unknown, possibly Ser
<220> FEATURE:
<221> NAME/KEY: MISC_FEATURE
<222> LOCATION: (145)..(145)
<223> OTHER INFORMATION: unknown, possibly one of the group Asp, Asn,
      Val, Leu, Ser, Phe, Pro, Ala and Cys
<220> FEATURE:
<221> NAME/KEY: MISC_FEATURE
<222> LOCATION: (183)..(183)
<223> OTHER INFORMATION: inknown, possibly one of the group Asp, Asn,
      Val, Leu, Ser,Phe, Pro, Ala and Cys
```

```
<220> FEATURE:
<221> NAME/KEY: MISC_FEATURE
<222> LOCATION: (212)..(212)
<223> OTHER INFORMATION: unknown, possibly one of the group Asp, Asn,
      Val, Leu, Ser,Phe, Pro, Ala and Cys
<220> FEATURE:
<221> NAME/KEY: MISC_FEATURE
<222> LOCATION: (275)..(275)
<223> OTHER INFORMATION: unknown, possibly one of the group Asp, Asn,
      Val, Leu, Ser,Phe, Pro, Ala and Cys
<220> FEATURE:
<221> NAME/KEY: MISC_FEATURE
<222> LOCATION: (282)..(282)
<223> OTHER INFORMATION: unknown, possibly one of the group Asp, Asn,
      Val, Leu, Ser,Phe, Pro, Ala and Cys
<220> FEATURE:
<221> NAME/KEY: MISC_FEATURE
<222> LOCATION: (323)..(323)
<223> OTHER INFORMATION: unknown, possibly Gln

<400> SEQUENCE: 9

Leu Pro Val Leu Ala Pro Val Thr Lys Asp Pro Ala Thr Ser Leu Tyr
1               5                   10                  15

Thr Ile Pro Phe His Asp Gly Ala Ser Leu Val Leu Asp Val Ala Gly
            20                  25                  30

Pro Leu Val Trp Ser Thr Cys Asp Gly Gly Gln Pro Pro Ala Glu Ile
        35                  40                  45

Pro Cys Ser Ser Pro Thr Cys Leu Leu Ala Asn Ala Tyr Pro Ala Pro
    50                  55                  60

Gly Cys Pro Ala Pro Ser Cys Gly Ser Asp Lys His Asp Lys Pro Cys
65                  70                  75                  80

Thr Ala Tyr Pro Tyr Asn Pro Val Ser Gly Ala Cys Ala Ala Xaa Ser
                85                  90                  95

Leu Xaa His Thr Xaa Phe Val Ala Asn Thr Thr Asp Gly Xaa Lys Pro
            100                 105                 110

Val Ser Lys Val Asn Val Gly Val Leu Ala Ala Cys Ala Pro Ser Lys
        115                 120                 125

Leu Leu Ala Ser Leu Pro Arg Gly Ser Thr Gly Val Ala Gly Leu Ala
    130                 135                 140

Xaa Ser Gly Leu Ala Leu Pro Ala Gln Val Ala Ser Ala Gln Lys Val
145                 150                 155                 160

Ala Asn Arg Phe Leu Leu Cys Leu Pro Thr Gly Pro Gly Val Ala
                165                 170                 175

Ile Phe Gly Gly Gly Pro Xaa Pro Trp Pro Gln Phe Thr Gln Ser Met
            180                 185                 190

Pro Tyr Thr Pro Leu Val Thr Lys Gly Gly Ser Pro Ala His Tyr Ile
        195                 200                 205

Ser Ala Arg Xaa Ile Glu Val Gly Asp Thr Arg Val Pro Val Ser Glu
    210                 215                 220

Gly Ala Leu Ala Thr Gly Gly Val Met Leu Ser Thr Arg Leu Pro Tyr
225                 230                 235                 240

Val Leu Leu Arg Arg Asp Val Tyr Arg Pro Leu Val Asp Ala Phe Thr
                245                 250                 255

Lys Ala Leu Ala Ala Gln His Ala Asn Gly Ala Pro Val Ala Arg Ala
            260                 265                 270

Val Glu Xaa Val Ala Pro Phe Gly Val Xaa Tyr Asp Thr Lys Thr Leu
        275                 280                 285

Gly Asn Asn Leu Gly Gly Tyr Ala Val Pro Asn Val Gln Leu Gly Leu
    290                 295                 300
```

-continued

```
Asp Gly Gly Ser Asp Trp Thr Met Thr Gly Lys Asn Ser Met Val Asp
305                 310                 315                 320

Val Lys Xaa Gly Thr Ala Cys Val Ala Phe Val Glu Met Lys Gly Val
            325                 330                 335

Ala Ala Gly Asp Gly Arg Ala Pro Ala Val Ile Leu Gly Gly Ala Gln
        340                 345                 350

Met Glu Asp Phe Val Leu Asp Phe Asp Met Glu Lys Lys Arg Leu Gly
    355                 360                 365

Phe Ser Arg Leu Pro His Phe Thr Gly Cys Gly Gly Leu
370                 375                 380
```

<210> SEQ ID NO 10
<211> LENGTH: 1199
<212> TYPE: DNA
<213> ORGANISM: Artificial Sequence
<220> FEATURE:
<223> OTHER INFORMATION: Description of Artificial Sequence: consensus
      sequence of TAXI I

<400> SEQUENCE: 10

| | | | | | | |
|---|---|---|---|---|---|---|
| gccacctccc | tctacacaat | cccctttccac | gacggcgcca | gcctcgtcct | cgacgtcgcc | 60 |
| ggccctctcg | tctggtccac | gtgcgatggc | ggccagccgc | ccgcggagat | cccgtgcagc | 120 |
| agccccacct | gcctcctcgc | caacgcctac | cccgccccgg | gctgccccgc | tcccagctgc | 180 |
| ggcagcgata | agcacgacaa | accgtgcacg | gcgtacccgt | acaacccggt | cagcggcgcg | 240 |
| tgcgccgcmk | ggagcctcty | ccacacgarr | ttcgtggcca | acaccaccga | cgggaryaar | 300 |
| ccggtgagca | aggtgaacgt | cggggtcctg | gcggcgtgcg | cgccgagcaa | gctcctggcg | 360 |
| tcgctgcccc | ggggctccac | gggcgtggcc | gggctcgcgg | actccggcct | ggcgctgccg | 420 |
| gcgcaggtgg | cgtccgcgca | gaaggtcgcc | aacaggttcc | tcctctgcct | ccccaccggc | 480 |
| ggccctggcg | tggccatctt | cggcggcggc | ccgctcccgt | ggccgcaatt | cacgcagtcg | 540 |
| atgccctaca | cgccgctcgt | caccaagggc | ggcagccccg | cgcactacat | ctccgccagg | 600 |
| tccatcgaag | tggggacac | ccgcgtcccc | gtatcggagg | gcgcgctcgc | caccggcggc | 660 |
| gtgatgctca | gcacgaggct | gccctacgtc | ttgctccgcc | gcgacgtgta | ccgcccgttg | 720 |
| gtggacgcgt | tcaccaaggc | cctggcggcg | cagcatgcca | acggagcgcc | cgtggcgcgc | 780 |
| gcagtggagc | ctgtggcgcc | gttcggggtg | tgctacgaca | cgaagacgct | gggcaacaac | 840 |
| ctcggcgggt | acgcggtgcc | caacgtccag | ctggggctcg | atggcggsag | tgactggacg | 900 |
| atgaccggga | agaactcgat | ggtggacgtc | aagcmrggga | cggcgtgcgt | tgcgttcgtg | 960 |
| gagatgaagg | gagtggcggc | cggcgacggc | agggcgccgg | cggtgatcct | cggaggggcc | 1020 |
| cagatggagg | acttcgtgct | cgacttcgac | atggagaaga | agcggctcgg | gtttagcagg | 1080 |
| ctgccgcact | ttacggggttg | cggcggcctg | taataataaa | tctgtttaac | gacaggtgga | 1140 |
| ttcgtccact | actgcgtgta | ataaataagg | gaagaaacac | tttccatcag | tggtttcat | 1199 |

<210> SEQ ID NO 11
<211> LENGTH: 185
<212> TYPE: PRT
<213> ORGANISM: Hordeum vulgare
<220> FEATURE:
<221> NAME/KEY: PEPTIDE
<222> LOCATION: (1)..(185)
<223> OTHER INFORMATION: part of a xylanase inhibitor, a HVXI variant,
      wherein the first Xaa is unknown and the second Xaa is unknown
      (derived from an EST-sequence)
<220> FEATURE:
<221> NAME/KEY: MISC_FEATURE -continued

```
<222> LOCATION: (72)..(72)
<223> OTHER INFORMATION: unknown
<220> FEATURE:
<221> NAME/KEY: MISC_FEATURE
<222> LOCATION: (185)..(185)
<223> OTHER INFORMATION: unknown

<400> SEQUENCE: 11

Ala Gly Phe Ala Gly Ser Gly Leu Ala Leu Pro Ala Gln Val Ala Ser
1               5                   10                  15

Ala Gln Lys Val Ser His Arg Phe Leu Leu Cys Leu Pro Thr Gly Gly
            20                  25                  30

Ala Gly Val Ala Ile Leu Gly Gly Pro Leu Pro Trp Pro Gln Phe
        35                  40                  45

Thr Gln Ser Met Ala Tyr Thr Pro Leu Val Gly Lys Gln Gly Ser Pro
    50                  55                  60

Ala His Tyr Val Ser Gly Thr Xaa Ile Lys Val Glu Asp Thr Arg Val
65                  70                  75                  80

Pro Val Pro Asp Arg Ala Leu Val Thr Gly Val Met Leu Asn Thr
                85                  90                  95

Lys Leu Ala Tyr Val Leu Leu Arg Arg Asp Val Tyr Arg Pro Val Val
            100                 105                 110

Asp Ala Phe Thr Lys Ala Leu Ala Ala Gln His Ala Asn Gly Ala Pro
        115                 120                 125

Ala Ala Arg Ala Val Asp Pro Val Ala Pro Phe Gly Leu Cys Tyr Asp
    130                 135                 140

Ala Lys Thr Leu Gly Asn Asn Leu Gly Gly Tyr Ser Val Pro Asn Val
145                 150                 155                 160

Val Leu Ala Leu Asp Gly Gly Gly Glu Trp Ala Met Thr Gly Lys Asn
                165                 170                 175

Ser Met Val Asp Val Lys Pro Gly Xaa
            180                 185

<210> SEQ ID NO 12
<211> LENGTH: 185
<212> TYPE: PRT
<213> ORGANISM: Hordeum vulgare
<220> FEATURE:
<221> NAME/KEY: VARIANT
<222> LOCATION: (1)..(185)
<223> OTHER INFORMATION: variant of SEQ ID NO 11
<220> FEATURE:
<221> NAME/KEY: MISC_FEATURE
<222> LOCATION: (72)..(72)
<223> OTHER INFORMATION: unknown
<220> FEATURE:
<221> NAME/KEY: MISC_FEATURE
<222> LOCATION: (185)..(185)
<223> OTHER INFORMATION: unknown

<400> SEQUENCE: 12

Ala Gly Phe Ala Gly Ser Gly Leu Ala Leu Pro Ala Gln Val Ala Ser
1               5                   10                  15

Ala Gln Lys Val Ser His Arg Phe Leu Leu Cys Leu Pro Thr Gly Gly
            20                  25                  30

Ala Gly Val Ala Ile Leu Gly Gly Pro Leu Pro Trp Pro Gln Phe
        35                  40                  45

Thr Gln Ser Met Ala Tyr Thr Pro Leu Val Gly Lys Gln Gly Ser Pro
    50                  55                  60

Ala His Tyr Val Ser Gly Thr Xaa Ile Lys Val Glu Asp Thr Arg Val
65                  70                  75                  80
```

```
Pro Val Pro Asp Arg Ala Leu Val Thr Gly Gly Val Met Leu Asn Thr
                85                  90                  95

Lys Leu Ala Tyr Val Leu Leu Arg Arg Asp Val Tyr Arg Pro Val Val
            100                 105                 110

Asp Ala Phe Thr Lys Ala Leu Ala Ala Gln His Ala Asn Gly Ala Leu
        115                 120                 125

Ala Ala Arg Gly Val Asn Pro Val Ala Pro Phe Gly Leu Cys Tyr Asp
    130                 135                 140

Ala Lys Thr Asn Gly Asn Asn Leu Gly Gly Tyr Ser Val Pro Asn Val
145                 150                 155                 160

Val Leu Ala Leu Asp Gly Gly Gly Glu Trp Ala Met Thr Gly Lys Asn
                165                 170                 175

Ser Met Val Asp Val Lys Pro Gly Xaa
                180                 185
```

<210> SEQ ID NO 13
<211> LENGTH: 185
<212> TYPE: PRT
<213> ORGANISM: Hordeum vulgare
<220> FEATURE:
<221> NAME/KEY: VARIANT
<222> LOCATION: (1)..(185)
<223> OTHER INFORMATION: variant of SEQ ID NO 11
<220> FEATURE:
<221> NAME/KEY: MISC_FEATURE
<222> LOCATION: (72)..(72)
<223> OTHER INFORMATION: unknown
<220> FEATURE:
<221> NAME/KEY: MISC_FEATURE
<222> LOCATION: (128)..(128)
<223> OTHER INFORMATION: unknown, possibly one of the group Pro, Ala,
      Asp, Leu,Gly, Asn and Cys
<220> FEATURE:
<221> NAME/KEY: MISC_FEATURE
<222> LOCATION: (132)..(132)
<223> OTHER INFORMATION: unknown, possibly one of the group Pro, Ala,
      Asp, Leu,Gly, Asn and Cys
<220> FEATURE:
<221> NAME/KEY: MISC_FEATURE
<222> LOCATION: (134)..(134)
<223> OTHER INFORMATION: unknown, possibly one of the group Pro, Ala,
      Asp, Leu,Gly, Asn and Cys
<220> FEATURE:
<221> NAME/KEY: MISC_FEATURE
<222> LOCATION: (148)..(148)
<223> OTHER INFORMATION: unknown, possibly one of the group Pro, Ala,
      Asp, Leu,Gly, Asn and Cys
<220> FEATURE:
<221> NAME/KEY: MISC_FEATURE
<222> LOCATION: (185)..(185)
<223> OTHER INFORMATION: unknown

<400> SEQUENCE: 13

```
Ala Gly Phe Ala Gly Ser Gly Leu Ala Leu Pro Ala Gln Val Ala Ser
1               5                   10                  15

Ala Gln Lys Val Ser His Arg Phe Leu Leu Cys Leu Pro Thr Gly Gly
            20                  25                  30

Ala Gly Val Ala Ile Leu Gly Gly Pro Leu Pro Trp Pro Gln Phe
        35                  40                  45

Thr Gln Ser Met Ala Tyr Thr Pro Leu Val Gly Lys Gln Gly Ser Pro
    50                  55                  60

Ala His Tyr Val Ser Gly Thr Xaa Ile Lys Val Glu Asp Thr Arg Val
65                  70                  75                  80

Pro Val Pro Asp Arg Ala Leu Val Thr Gly Gly Val Met Leu Asn Thr
                85                  90                  95
```

```
Lys Leu Ala Tyr Val Leu Leu Arg Arg Asp Val Tyr Arg Pro Val Val
            100                 105                 110

Asp Ala Phe Thr Lys Ala Leu Ala Ala Gln His Ala Asn Gly Ala Xaa
            115                 120                 125

Ala Ala Arg Xaa Val Xaa Pro Val Ala Pro Phe Gly Leu Cys Tyr Asp
            130                 135                 140

Ala Lys Thr Xaa Gly Asn Asn Leu Gly Gly Tyr Ser Val Pro Asn Val
145                 150                 155                 160

Val Leu Ala Leu Asp Gly Gly Gly Glu Trp Ala Met Thr Gly Lys Asn
                165                 170                 175

Ser Met Val Asp Val Lys Pro Gly Xaa
            180                 185

<210> SEQ ID NO 14
<211> LENGTH: 553
<212> TYPE: DNA
<213> ORGANISM: Hordeum vulgare
<220> FEATURE:
<221> NAME/KEY: exon
<222> LOCATION: (1)..(553)
<223> OTHER INFORMATION: consensus sequence of HVXI (based on an EST
      sequence)
<220> FEATURE:
<221> NAME/KEY: misc_feature
<222> LOCATION: (215)..(215)
<223> OTHER INFORMATION: unknown

<400> SEQUENCE: 14
```

| | | | | | | | | | | | | | | | | |
|---|---|---|---|---|---|---|---|---|---|---|---|---|---|---|---|---|
| gcg | ggc | ttc | gcg | ggc | tcc | ggc | ctg | gcg | ctg | ccg | gcg | cag | gtg | gcg | tcc | 48 |
| Ala | Gly | Phe | Ala | Gly | Ser | Gly | Leu | Ala | Leu | Pro | Ala | Gln | Val | Ala | Ser | |
| 1 | | | | 5 | | | | | 10 | | | | | 15 | | |

| gcg | cag | aag | gtc | tcc | cat | cgg | ttc | ctc | ctc | tgc | ctc | ccc | acg | ggc | ggc | 96 |
|---|---|---|---|---|---|---|---|---|---|---|---|---|---|---|---|---|
| Ala | Gln | Lys | Val | Ser | His | Arg | Phe | Leu | Leu | Cys | Leu | Pro | Thr | Gly | Gly | |
| | | | 20 | | | | | 25 | | | | | 30 | | | |

| gcc | ggc | gtg | gcc | atc | ctc | ggc | ggc | ggc | ccg | ctc | ccg | tgg | ccg | cag | ttc | 144 |
|---|---|---|---|---|---|---|---|---|---|---|---|---|---|---|---|---|
| Ala | Gly | Val | Ala | Ile | Leu | Gly | Gly | Gly | Pro | Leu | Pro | Trp | Pro | Gln | Phe | |
| | | | 35 | | | | | 40 | | | | | 45 | | | |

| acg | cag | tcc | atg | gcc | tac | acc | ccg | ctc | gtc | ggc | aag | caa | ggc | agc | ccc | 192 |
|---|---|---|---|---|---|---|---|---|---|---|---|---|---|---|---|---|
| Thr | Gln | Ser | Met | Ala | Tyr | Thr | Pro | Leu | Val | Gly | Lys | Gln | Gly | Ser | Pro | |
| | 50 | | | | | 55 | | | | | 60 | | | | | |

| gcg | cac | tac | gtc | tcg | ggc | acg | tnc | atc | aaa | gtc | gag | gac | acc | cgc | gtt | 240 |
|---|---|---|---|---|---|---|---|---|---|---|---|---|---|---|---|---|
| Ala | His | Tyr | Val | Ser | Gly | Thr | Xaa | Ile | Lys | Val | Glu | Asp | Thr | Arg | Val | |
| 65 | | | | | 70 | | | | | 75 | | | | | 80 | |

| ccc | gtt | ccg | gac | cgc | gcg | ctc | gtc | acc | ggg | ggg | gtg | atg | ctc | aac | acg | 288 |
|---|---|---|---|---|---|---|---|---|---|---|---|---|---|---|---|---|
| Pro | Val | Pro | Asp | Arg | Ala | Leu | Val | Thr | Gly | Gly | Val | Met | Leu | Asn | Thr | |
| | | | 85 | | | | | 90 | | | | | 95 | | | |

| aag | ctg | gcc | tac | gtc | ttg | ctc | cgc | cgc | gac | gtg | tac | cgc | ccg | gtg | gtg | 336 |
|---|---|---|---|---|---|---|---|---|---|---|---|---|---|---|---|---|
| Lys | Leu | Ala | Tyr | Val | Leu | Leu | Arg | Arg | Asp | Val | Tyr | Arg | Pro | Val | Val | |
| | | | 100 | | | | | 105 | | | | | 110 | | | |

| gac | gcg | ttc | acc | aag | gcc | ctg | gcg | gcg | cag | cat | gcc | aac | gga | gcg | ccc | 384 |
|---|---|---|---|---|---|---|---|---|---|---|---|---|---|---|---|---|
| Asp | Ala | Phe | Thr | Lys | Ala | Leu | Ala | Ala | Gln | His | Ala | Asn | Gly | Ala | Pro | |
| | | | 115 | | | | | 120 | | | | | 125 | | | |

| gcg | gcg | cgc | gcc | gtg | gac | ccc | gtg | gcg | ccg | ttc | ggg | ctg | tgc | tac | gac | 432 |
|---|---|---|---|---|---|---|---|---|---|---|---|---|---|---|---|---|
| Ala | Ala | Arg | Ala | Val | Asp | Pro | Val | Ala | Pro | Phe | Gly | Leu | Cys | Tyr | Asp | |
| | | | 130 | | | | | 135 | | | | | 140 | | | |

| gcc | aag | acg | ctg | ggc | aac | aac | ctc | ggc | ggg | tac | tcg | gtg | ccc | aac | gtg | 480 |
|---|---|---|---|---|---|---|---|---|---|---|---|---|---|---|---|---|
| Ala | Lys | Thr | Leu | Gly | Asn | Asn | Leu | Gly | Gly | Tyr | Ser | Val | Pro | Asn | Val | |
| 145 | | | | | 150 | | | | | 155 | | | | | 160 | |

| gtg | ctg | gcg | ctc | gac | ggc | ggg | ggt | gaa | tgg | gcg | atg | acc | ggg | aag | aac | 528 |
|---|---|---|---|---|---|---|---|---|---|---|---|---|---|---|---|---|
| Val | Leu | Ala | Leu | Asp | Gly | Gly | Gly | Glu | Trp | Ala | Met | Thr | Gly | Lys | Asn | |
| | | | | 165 | | | | | 170 | | | | | 175 | | |

```
tcg atg gtg gac gtc aag ccg ggg a                                    553
Ser Met Val Asp Val Lys Pro Gly
            180

<210> SEQ ID NO 15
<211> LENGTH: 1152
<212> TYPE: DNA
<213> ORGANISM: Triticum aestivum
<220> FEATURE:
<221> NAME/KEY: exon
<222> LOCATION: (1)..(1110)
<223> OTHER INFORMATION: part of a xylanase inhibitor gene termed TAXI
      -I.01 from Triticum aestivum cultivar Soissons

<400> SEQUENCE: 15 gcc acc tcc ctc tac aca atc ccc ttc cac gac ggc gcc agc ctc gtc    48
Ala Thr Ser Leu Tyr Thr Ile Pro Phe His Asp Gly Ala Ser Leu Val
1               5                   10                  15 ctc gac gtc gcc ggc cct ctc gtc tgg tcc acg tgc gat ggc ggc cag    96
Leu Asp Val Ala Gly Pro Leu Val Trp Ser Thr Cys Asp Gly Gly Gln
            20                  25                  30 ccg ccc gcg gag atc ccg tgc agc agc ccc acc tgc ctc ctc gcc aac   144
Pro Pro Ala Glu Ile Pro Cys Ser Ser Pro Thr Cys Leu Leu Ala Asn
        35                  40                  45 gcc tac ccc gcc ccg ggc tgc ccc gcg ccc agc tgc ggc agc aac agg   192
Ala Tyr Pro Ala Pro Gly Cys Pro Ala Pro Ser Cys Gly Ser Asn Arg
    50                  55                  60 cac aac aag ccg tgc acg gcg tac ccg tac aac ccg gtc agc ggc gcg   240
His Asn Lys Pro Cys Thr Ala Tyr Pro Tyr Asn Pro Val Ser Gly Ala
65                  70                  75                  80 tgc gcc gca ggg agc ctc tcc cac acg aga ttc gtg gcc aac acc acc   288
Cys Ala Ala Gly Ser Leu Ser His Thr Arg Phe Val Ala Asn Thr Thr
                85                  90                  95 gac ggg agc aag ccg gtg agc aag gtg aac gtc ggg gtc ctg gcg gcg   336
Asp Gly Ser Lys Pro Val Ser Lys Val Asn Val Gly Val Leu Ala Ala
            100                 105                 110 tgc gcg ccg agc aag ctc ctg gcg tcg ctg ccc cgg ggc tcc acg ggc   384
Cys Ala Pro Ser Lys Leu Leu Ala Ser Leu Pro Arg Gly Ser Thr Gly
        115                 120                 125 gtg gcc ggg ctc gcg aac tcc ggc ttg gcg ctg ccg gcg cag gtg gca   432
Val Ala Gly Leu Ala Asn Ser Gly Leu Ala Leu Pro Ala Gln Val Ala
    130                 135                 140 tcc gcg cag aag gtc gcc aac agg ttc ctc ctc tgc ctc ccc acc ggc   480
Ser Ala Gln Lys Val Ala Asn Arg Phe Leu Leu Cys Leu Pro Thr Gly
145                 150                 155                 160 ggc ctt ggc gtg gcc ata ttt ggc ggc ggc ccg gtc ccg tgg ccg caa   528
Gly Leu Gly Val Ala Ile Phe Gly Gly Gly Pro Val Pro Trp Pro Gln
                165                 170                 175 ttc acg cag tcg atg cct tac acg ccg ctc gtc acc aag ggc ggc agc   576
Phe Thr Gln Ser Met Pro Tyr Thr Pro Leu Val Thr Lys Gly Gly Ser
            180                 185                 190 ccc gcg cac tac atc tcg gcc agg tcc att gta gtg ggg gac acc cgc   624
Pro Ala His Tyr Ile Ser Ala Arg Ser Ile Val Val Gly Asp Thr Arg
        195                 200                 205 gtc ccc gta tcg gag ggc gcg ctc gcc acc ggc ggt gtg atg ctc agc   672
Val Pro Val Ser Glu Gly Ala Leu Ala Thr Gly Gly Val Met Leu Ser
    210                 215                 220 acg agg cta ccc tac gtc ttg ctc cgc ccc gac gtg tac cgc ccg ttg   720
Thr Arg Leu Pro Tyr Val Leu Leu Arg Pro Asp Val Tyr Arg Pro Leu
225                 230                 235                 240 atg gac gcg ttt acc aag gcc ctg gcg gcg cag cat gcc aac gga gcg   768
```

```
Met Asp Ala Phe Thr Lys Ala Leu Ala Ala Gln His Ala Asn Gly Ala
            245                 250                 255 ccc gtg gcg cgc gca gtg gag gct gtg gcg ccg ttc ggg gtg tgc tac      816
Pro Val Ala Arg Ala Val Glu Ala Val Ala Pro Phe Gly Val Cys Tyr
            260                 265                 270 gac acg aag acg ctg ggc aac aac ctc ggc ggg tac gcg gtg ccc aac      864
Asp Thr Lys Thr Leu Gly Asn Asn Leu Gly Gly Tyr Ala Val Pro Asn
        275                 280                 285 gtc cag ctg ggg ctc gat ggc ggc agt gac tgg acg atg acc ggg aag      912
Val Gln Leu Gly Leu Asp Gly Gly Ser Asp Trp Thr Met Thr Gly Lys
    290                 295                 300 aac tcg atg gtg gac gtc aag caa ggg acg gcg tgc gtt gcg ttc gtg      960
Asn Ser Met Val Asp Val Lys Gln Gly Thr Ala Cys Val Ala Phe Val
305                 310                 315                 320 gag atg aag gga gtg gcg gcc ggc gac ggc agg gcg ccg gcg gtg atc     1008
Glu Met Lys Gly Val Ala Ala Gly Asp Gly Arg Ala Pro Ala Val Ile
                325                 330                 335 ctc gga ggg gcc cag atg gag gac ttc gtg ctc gac ttc gac atg gag     1056
Leu Gly Gly Ala Gln Met Glu Asp Phe Val Leu Asp Phe Asp Met Glu
            340                 345                 350 aag aag cgg ctc ggg ttt agc agg ctg ccg cac ttt acg ggt tgc ggc     1104
Lys Lys Arg Leu Gly Phe Ser Arg Leu Pro His Phe Thr Gly Cys Gly
        355                 360                 365 ggc ctg taataataaa tctgtttaac gacaggtgga ttcgtccact ac              1152
Gly Leu
    370

<210> SEQ ID NO 16
<211> LENGTH: 1152
<212> TYPE: DNA
<213> ORGANISM: Triticum aestivum
<220> FEATURE:
<221> NAME/KEY: exon
<222> LOCATION: (1)..(1110)
<223> OTHER INFORMATION: part of a xylanase inhibitor gene termed TAXI-I
      .02 from Triticum aestivum cultivar Estica

<400> SEQUENCE: 16 gcc acc tcc ctc tac aca atc ccc ttc cac gac ggc gcc agc ctc gtc       48
Ala Thr Ser Leu Tyr Thr Ile Pro Phe His Asp Gly Ala Ser Leu Val
1               5                   10                  15 ctc gac gtc gcc ggc cct ctc gtc tgg tcc acg tgc gat ggc ggc cag       96
Leu Asp Val Ala Gly Pro Leu Val Trp Ser Thr Cys Asp Gly Gly Gln
            20                  25                  30 ccg ccc gcg gag atc ccg tgc agc agc ccc acc tgc ctc ctc gcc aac      144
Pro Pro Ala Glu Ile Pro Cys Ser Ser Pro Thr Cys Leu Leu Ala Asn
        35                  40                  45 gcc tac ccc gcc ccg ggc tgc ccc gct ccc agc tgc ggc agc gat aag      192
Ala Tyr Pro Ala Pro Gly Cys Pro Ala Pro Ser Cys Gly Ser Asp Lys
    50                  55                  60 cac gac aaa ccg tgc acg gcg tac ccg tac aac ccg gtc agc ggc gcg      240
His Asp Lys Pro Cys Thr Ala Tyr Pro Tyr Asn Pro Val Ser Gly Ala
65                  70                  75                  80 tgc gcc gca ggg agc ctc tcc cac acg aga ttc gtg gcc aac acc acc      288
Cys Ala Ala Gly Ser Leu Ser His Thr Arg Phe Val Ala Asn Thr Thr
                85                  90                  95 gac ggg agc aag ccg gtg agc aag gtg aac gtc ggg gtc ctg gcg gcg      336
Asp Gly Ser Lys Pro Val Ser Lys Val Asn Val Gly Val Leu Ala Ala
            100                 105                 110 tgc gcg ccg agc aag ctc ctg gcg tcg ctg ccc cgg ggc tcc acg ggc      384
Cys Ala Pro Ser Lys Leu Leu Ala Ser Leu Pro Arg Gly Ser Thr Gly
        115                 120                 125
```

```
gtg gcc ggg ctc gcg aac tcc ggc ttg gcg ctg ccg gcg cag gtg gca      432
Val Ala Gly Leu Ala Asn Ser Gly Leu Ala Leu Pro Ala Gln Val Ala
    130                 135                 140 tcc gcg cag aag gtc gcc aac agg ttc ctc ctc tgc ctc ccc acc ggc      480
Ser Ala Gln Lys Val Ala Asn Arg Phe Leu Leu Cys Leu Pro Thr Gly
145                 150                 155                 160 ggc cct ggc gtg gcc ata ttt ggc ggc ggc ccg gtc ccg tgg ccg caa      528
Gly Pro Gly Val Ala Ile Phe Gly Gly Gly Pro Val Pro Trp Pro Gln
                165                 170                 175 ttc acg cag tcg atg cct tac acg ccg ctc gtc acc aag ggc ggc agc      576
Phe Thr Gln Ser Met Pro Tyr Thr Pro Leu Val Thr Lys Gly Gly Ser
            180                 185                 190 ccc gcg cac tac atc tcg gcc agg tcc att gta gtg ggg gac acc cgc      624
Pro Ala His Tyr Ile Ser Ala Arg Ser Ile Val Val Gly Asp Thr Arg
        195                 200                 205 gtc ccc gta ccg gag ggc gcg ctc gcc acc ggc ggc gtg atg ctc agc      672
Val Pro Val Pro Glu Gly Ala Leu Ala Thr Gly Gly Val Met Leu Ser
    210                 215                 220 acg agg cta ccc tac gtc ttg ctc cgc ccc gac gtg tac cgc ccg ttg      720
Thr Arg Leu Pro Tyr Val Leu Leu Arg Pro Asp Val Tyr Arg Pro Leu
225                 230                 235                 240 atg gac gcg ttc acc aag gcc ctg gcg gcg cag cat gcc aac gga gcg      768
Met Asp Ala Phe Thr Lys Ala Leu Ala Ala Gln His Ala Asn Gly Ala
                245                 250                 255 ccc gtg gcg cgc gca gtg gag gct gtg gcg ccg ttc ggg gtg tgc tac      816
Pro Val Ala Arg Ala Val Glu Ala Val Ala Pro Phe Gly Val Cys Tyr
            260                 265                 270 gac acg aag acg ctg ggc aac aac ctc ggg tac gcg gtg ccc aac          864
Asp Thr Lys Thr Leu Gly Asn Asn Leu Gly Gly Tyr Ala Val Pro Asn
        275                 280                 285 gtc cag ctg ggg ctc gat ggc ggc agt gac tgg acg atg acc ggg aag      912
Val Gln Leu Gly Leu Asp Gly Gly Ser Asp Trp Thr Met Thr Gly Lys
    290                 295                 300 aac tcg atg gtg gac gtc aag caa ggg acg gcg tgc gtt gcg ttc gtg      960
Asn Ser Met Val Asp Val Lys Gln Gly Thr Ala Cys Val Ala Phe Val
305                 310                 315                 320 gag atg aag gga gtg gcg gcc ggc gac ggc agg gcg ccg gcg gtg atc     1008
Glu Met Lys Gly Val Ala Ala Gly Asp Gly Arg Ala Pro Ala Val Ile
                325                 330                 335 ctc gga ggg gcc cag atg gag gac ttc gtg ctc gac ttc gac atg gag     1056
Leu Gly Gly Ala Gln Met Glu Asp Phe Val Leu Asp Phe Asp Met Glu
            340                 345                 350 aag aag cgg ctc ggg ttt agc agg ctg ccg cac ttt acg ggt tgc ggc     1104
Lys Lys Arg Leu Gly Phe Ser Arg Leu Pro His Phe Thr Gly Cys Gly
        355                 360                 365 ggc ctg taataataaa tctgtttaac gacaggtgga ttcgtccact ac              1152
Gly Leu
    370

<210> SEQ ID NO 17
<211> LENGTH: 632
<212> TYPE: DNA
<213> ORGANISM: Triticum durum
<220> FEATURE:
<221> NAME/KEY: exon
<222> LOCATION: (3)..(590)
<223> OTHER INFORMATION: part of a xylanase inhibitor gene termed
      TDXI-I.01 from Triticum durum cultivar Mexicali

<400> SEQUENCE: 17 cg caa ttc acg cag tcg atg cct tac acg ccg ctc gtc acc aag ggc       47
```

```
      Gln Phe Thr Gln Ser Met Pro Tyr Thr Pro Leu Val Thr Lys Gly
       1               5                  10                  15 ggc agc ccc gcg cac tac atc tcg gcc agg tcc att gta gtg ggg gac        95
Gly Ser Pro Ala His Tyr Ile Ser Ala Arg Ser Ile Val Val Gly Asp
               20                  25                  30 acc cgc gtc ccc gcc gta tcg gag ggc gcg ctc gcc acc ggc ggc gtg       143
Thr Arg Val Pro Ala Val Ser Glu Gly Ala Leu Ala Thr Gly Gly Val
           35                  40                  45 atg ctc agc acg agg cta ccc tac gtc ttg ctc cgc ccc gac gtg tac       191
Met Leu Ser Thr Arg Leu Pro Tyr Val Leu Leu Arg Pro Asp Val Tyr
       50                  55                  60 cgc ccg ttg atg gac gcg ttc acc aag gcc ctg gcg gcg cag cat gcc       239
Arg Pro Leu Met Asp Ala Phe Thr Lys Ala Leu Ala Ala Gln His Ala
   65                  70                  75 aac gga gcg ccc gtg gcg cgc gca gtg gag gct gtg gcg ccg ttc ggg       287
Asn Gly Ala Pro Val Ala Arg Ala Val Glu Ala Val Ala Pro Phe Gly
80                  85                  90                  95 gtg tgc tac gac acg aag acg ctg ggc aac aac ctc ggc ggg tac gcg       335
Val Cys Tyr Asp Thr Lys Thr Leu Gly Asn Asn Leu Gly Gly Tyr Ala
                100                 105                 110 gtg ccc aac gtc cag ctg ggc ctc gat ggc ggc agt gac tgg acg atg       383
Val Pro Asn Val Gln Leu Gly Leu Asp Gly Gly Ser Asp Trp Thr Met
            115                 120                 125 acc ggg aag aac tcg atg gtg gac gtc aag caa ggg acg gcg tgc gtt       431
Thr Gly Lys Asn Ser Met Val Asp Val Lys Gln Gly Thr Ala Cys Val
        130                 135                 140 gcg ttc gtg gag atg aag gga gtg gcg gcc ggc gac ggc agg gcg ccg       479
Ala Phe Val Glu Met Lys Gly Val Ala Ala Gly Asp Gly Arg Ala Pro
145                 150                 155 gcg gtg atc ctc gga ggg gcc cag atg gag gac ttc gtg ctc gac ttc       527
Ala Val Ile Leu Gly Gly Ala Gln Met Glu Asp Phe Val Leu Asp Phe
160                 165                 170                 175 gac atg gag aag aag cgg ctc ggg ttt agc agg ctg ccg cac ttt acg       575
Asp Met Glu Lys Lys Arg Leu Gly Phe Ser Arg Leu Pro His Phe Thr
                180                 185                 190 ggt tgc ggc ggc ctg taataataaa tctgtttaac gacaggtgga ttcgtccact       630
Gly Cys Gly Gly Leu
            195 ac                                                                    632

<210> SEQ ID NO 18
<211> LENGTH: 833
<212> TYPE: DNA
<213> ORGANISM: Aegilops tauschii
<220> FEATURE:
<221> NAME/KEY: exon
<222> LOCATION: (1)..(831)
<223> OTHER INFORMATION: part of a xylanase inhibitor gene termed
      ATXI-II.01 from Aegilops tauschii variety Acc2220051

<400> SEQUENCE: 18 gcc acc tcc ctc tac aca atc ccc ttc cac cag ggc gcc agc ctc gtc        48
Ala Thr Ser Leu Tyr Thr Ile Pro Phe His Gln Gly Ala Ser Leu Val
 1               5                  10                  15 ctt gac atc gcc ggc ccg ctc gtc tgg tcc acg tgc cag cgc ggc gat        96
Leu Asp Ile Ala Gly Pro Leu Val Trp Ser Thr Cys Gln Arg Gly Asp
            20                  25                  30 ctg ccg aca gat atc ccg tgc agt agc ccc acc tgc ctc ctc gcc aac       144
Leu Pro Thr Asp Ile Pro Cys Ser Ser Pro Thr Cys Leu Leu Ala Asn
        35                  40                  45 gcc tac ccc gcc ccg ggc tgc ccc gcg ccc agc tgc ggc agc ggc agc       192
```

```
                                                                                  240
cac gac aag caa tgc acg acg tac cca tcc aac ccg gtc acc ggc gcg
His Asp Lys Gln Cys Thr Thr Tyr Pro Ser Asn Pro Val Thr Gly Ala
 65                  70                  75                  80

288
tgc gcc gcc ggg agc ctc gcc cgc acg acg ctc ata gcc gac acc acc
Cys Ala Ala Gly Ser Leu Ala Arg Thr Thr Leu Ile Ala Asp Thr Thr
                 85                  90                  95

336
gac ggg aat aac ccg gtg agc cag gtg tac gtc cgg atc ctg gcg gcg
Asp Gly Asn Asn Pro Val Ser Gln Val Tyr Val Arg Ile Leu Ala Ala
             100                 105                 110

384
tgc gcg ccg aga aag ctc ctg gcg tcg ctg ccc cgc ggc tcc atg ggc
Cys Ala Pro Arg Lys Leu Leu Ala Ser Leu Pro Arg Gly Ser Met Gly
         115                 120                 125

432
gtc gcc ggg cta ggg ggc tcc ggc ctg gcg ctg ccg gcg cag gtg gcg
Val Ala Gly Leu Gly Gly Ser Gly Leu Ala Leu Pro Ala Gln Val Ala
     130                 135                 140

480
tcc acc cag aag gtc gcc aac aag ttt ctc ctc tgc ctc ccc agc ggc
Ser Thr Gln Lys Val Ala Asn Lys Phe Leu Leu Cys Leu Pro Ser Gly
145                 150                 155                 160

528
ggc cct ggc gtg gcc atc ttc ggc ggc ggc ccg ctc ccg tgg ccg caa
Gly Pro Gly Val Ala Ile Phe Gly Gly Gly Pro Leu Pro Trp Pro Gln
                165                 170                 175

576
ttg acg cag tcg atg ccg tac acg ccg ctc gtc acc aag ggc ggc agc
Leu Thr Gln Ser Met Pro Tyr Thr Pro Leu Val Thr Lys Gly Gly Ser
            180                 185                 190

624
ccc gcg cac tac atc tcc gtc aag gcc atc caa ctg gag gac acc cgc
Pro Ala His Tyr Ile Ser Val Lys Ala Ile Gln Leu Glu Asp Thr Arg
        195                 200                 205

672
gtc tcc gtc tca gag cgc gtg ctc gcc acc ggc ggc gtg atg ctc agc
Val Ser Val Ser Glu Arg Val Leu Ala Thr Gly Gly Val Met Leu Ser
    210                 215                 220

720
acg agg ctg ccc tac gcc ttg ctc cgc cac gac gtc tac cgc ccg ttg
Thr Arg Leu Pro Tyr Ala Leu Leu Arg His Asp Val Tyr Arg Pro Leu
225                 230                 235                 240

768
gtg gac gcg ttc acc aag gcc ctg gcg gcg cag cct gcc aac gga gcg
Val Asp Ala Phe Thr Lys Ala Leu Ala Ala Gln Pro Ala Asn Gly Ala
                245                 250                 255

816
ccc gtg gcg cgc gcc gtg aag cct gtg gca ccg ttc gag ctg tgc tac
Pro Val Ala Arg Ala Val Lys Pro Val Ala Pro Phe Glu Leu Cys Tyr
            260                 265                 270

833
gac acg aag acg ctg gg
Asp Thr Lys Thr Leu
        275

<210> SEQ ID NO 19
<211> LENGTH: 370
<212> TYPE: PRT
<213> ORGANISM: Triticum aestivum
<220> FEATURE:
<221> NAME/KEY: PEPTIDE
<222> LOCATION: (1)..(370)
<223> OTHER INFORMATION: part of a xylanase inhibitor type I encoded by
      SEQ ID NO 15

<400> SEQUENCE: 19

Ala Thr Ser Leu Tyr Thr Ile Pro Phe His Asp Gly Ala Ser Leu Val
  1               5                  10                  15

Leu Asp Val Ala Gly Pro Leu Val Trp Ser Thr Cys Asp Gly Gly Gln
             20                  25                  30

Pro Pro Ala Glu Ile Pro Cys Ser Ser Pro Thr Cys Leu Leu Ala Asn
```

-continued

```
                35                  40                  45
Ala Tyr Pro Ala Pro Gly Cys Pro Ala Pro Ser Cys Gly Ser Asn Arg
 50                  55                  60
His Asn Lys Pro Cys Thr Ala Tyr Pro Tyr Asn Pro Val Ser Gly Ala
 65                  70                  75                  80
Cys Ala Ala Gly Ser Leu Ser His Thr Arg Phe Val Ala Asn Thr Thr
                 85                  90                  95
Asp Gly Ser Lys Pro Val Ser Lys Val Asn Val Gly Val Leu Ala Ala
                100                 105                 110
Cys Ala Pro Ser Lys Leu Leu Ala Ser Leu Pro Arg Gly Ser Thr Gly
            115                 120                 125
Val Ala Gly Leu Ala Asn Ser Gly Leu Ala Leu Pro Ala Gln Val Ala
130                 135                 140
Ser Ala Gln Lys Val Ala Asn Arg Phe Leu Leu Cys Leu Pro Thr Gly
145                 150                 155                 160
Gly Leu Gly Val Ala Ile Phe Gly Gly Gly Pro Val Pro Trp Pro Gln
                165                 170                 175
Phe Thr Gln Ser Met Pro Tyr Thr Pro Leu Val Thr Lys Gly Gly Ser
            180                 185                 190
Pro Ala His Tyr Ile Ser Ala Arg Ser Ile Val Val Gly Asp Thr Arg
            195                 200                 205
Val Pro Val Ser Glu Gly Ala Leu Ala Thr Gly Gly Val Met Leu Ser
210                 215                 220
Thr Arg Leu Pro Tyr Val Leu Leu Arg Pro Asp Val Tyr Arg Pro Leu
225                 230                 235                 240
Met Asp Ala Phe Thr Lys Ala Leu Ala Ala Gln His Ala Asn Gly Ala
                245                 250                 255
Pro Val Ala Arg Ala Val Glu Ala Val Ala Pro Phe Gly Val Cys Tyr
            260                 265                 270
Asp Thr Lys Thr Leu Gly Asn Asn Leu Gly Gly Tyr Ala Val Pro Asn
            275                 280                 285
Val Gln Leu Gly Leu Asp Gly Gly Ser Asp Trp Thr Met Thr Gly Lys
290                 295                 300
Asn Ser Met Val Asp Val Lys Gln Gly Thr Ala Cys Val Ala Phe Val
305                 310                 315                 320
Glu Met Lys Gly Val Ala Ala Gly Asp Gly Arg Ala Pro Ala Val Ile
                325                 330                 335
Leu Gly Gly Ala Gln Met Glu Asp Phe Val Leu Asp Phe Asp Met Glu
            340                 345                 350
Lys Lys Arg Leu Gly Phe Ser Arg Leu Pro His Phe Thr Gly Cys Gly
            355                 360                 365
Gly Leu
    370

<210> SEQ ID NO 20
<211> LENGTH: 370
<212> TYPE: PRT
<213> ORGANISM: Triticum aestivum
<220> FEATURE:
<221> NAME/KEY: PEPTIDE
<222> LOCATION: (1)..(370)
<223> OTHER INFORMATION: part of a xylanase inhibitor type I encoded by
      SEQ ID NO 16

<400> SEQUENCE: 20

Ala Thr Ser Leu Tyr Thr Ile Pro Phe His Asp Gly Ala Ser Leu Val
```

```
                1               5                  10                 15
Leu Asp Val Ala Gly Pro Leu Val Trp Ser Thr Cys Asp Gly Gly Gln
                    20                  25                 30

Pro Pro Ala Glu Ile Pro Cys Ser Ser Pro Thr Cys Leu Leu Ala Asn
                    35                  40                 45

Ala Tyr Pro Ala Pro Gly Cys Pro Ala Pro Ser Cys Gly Ser Asp Lys
        50                  55                  60

His Asp Lys Pro Cys Thr Ala Tyr Pro Tyr Asn Pro Val Ser Gly Ala
65                      70                  75                 80

Cys Ala Ala Gly Ser Leu Ser His Thr Arg Phe Val Ala Asn Thr Thr
                    85                  90                 95

Asp Gly Ser Lys Pro Val Ser Lys Val Asn Val Gly Val Leu Ala Ala
                    100                 105                110

Cys Ala Pro Ser Lys Leu Leu Ala Ser Leu Pro Arg Gly Ser Thr Gly
                    115                 120                125

Val Ala Gly Leu Ala Asn Ser Gly Leu Ala Leu Pro Ala Gln Val Ala
                    130                 135                140

Ser Ala Gln Lys Val Ala Asn Arg Phe Leu Leu Cys Leu Pro Thr Gly
145                     150                 155                160

Gly Pro Gly Val Ala Ile Phe Gly Gly Pro Val Pro Trp Pro Gln
                    165                 170                 175

Phe Thr Gln Ser Met Pro Tyr Thr Pro Leu Val Thr Lys Gly Gly Ser
                    180                 185                 190

Pro Ala His Tyr Ile Ser Ala Arg Ser Ile Val Gly Asp Thr Arg
                    195                 200                 205

Val Pro Val Pro Glu Gly Ala Leu Ala Thr Gly Gly Val Met Leu Ser
210                     215                 220

Thr Arg Leu Pro Tyr Val Leu Leu Arg Pro Asp Val Tyr Arg Pro Leu
225                     230                 235                240

Met Asp Ala Phe Thr Lys Ala Leu Ala Ala Gln His Ala Asn Gly Ala
                    245                 250                 255

Pro Val Ala Arg Ala Val Glu Ala Val Ala Pro Phe Gly Val Cys Tyr
                    260                 265                 270

Asp Thr Lys Thr Leu Gly Asn Asn Leu Gly Gly Tyr Ala Val Pro Asn
                    275                 280                 285

Val Gln Leu Gly Leu Asp Gly Ser Asp Trp Thr Met Thr Gly Lys
                    290                 295                 300

Asn Ser Met Val Asp Val Lys Gln Gly Thr Ala Cys Val Ala Phe Val
305                     310                 315                 320

Glu Met Lys Gly Val Ala Ala Gly Asp Gly Arg Ala Pro Ala Val Ile
                    325                 330                 335

Leu Gly Gly Ala Gln Met Glu Asp Phe Val Leu Asp Phe Asp Met Glu
                    340                 345                 350

Lys Lys Arg Leu Gly Phe Ser Arg Leu Pro His Phe Thr Gly Cys Gly
                    355                 360                 365

Gly Leu
    370

<210> SEQ ID NO 21
<211> LENGTH: 196
<212> TYPE: PRT
<213> ORGANISM: Triticum durum
<220> FEATURE:
<221> NAME/KEY: PEPTIDE
<222> LOCATION: (1)..(196)
```

<223> OTHER INFORMATION: part of a xylanase inhibitor type I encoded by
SEQ ID NO 17

<400> SEQUENCE: 21

```
Gln Phe Thr Gln Ser Met Pro Tyr Thr Pro Leu Val Thr Lys Gly Gly
1               5                   10                  15

Ser Pro Ala His Tyr Ile Ser Ala Arg Ser Ile Val Val Gly Asp Thr
            20                  25                  30

Arg Val Pro Ala Val Ser Glu Gly Ala Leu Ala Thr Gly Gly Val Met
        35                  40                  45

Leu Ser Thr Arg Leu Pro Tyr Val Leu Arg Pro Asp Val Tyr Arg
    50                  55                  60

Pro Leu Met Asp Ala Phe Thr Lys Ala Leu Ala Gln His Ala Asn
65                  70                  75                  80

Gly Ala Pro Val Ala Arg Ala Val Glu Ala Val Ala Pro Phe Gly Val
                85                  90                  95

Cys Tyr Asp Thr Lys Thr Leu Gly Asn Asn Leu Gly Gly Tyr Ala Val
            100                 105                 110

Pro Asn Val Gln Leu Gly Leu Asp Gly Gly Ser Asp Trp Thr Met Thr
        115                 120                 125

Gly Lys Asn Ser Met Val Asp Val Lys Gln Gly Thr Ala Cys Val Ala
130                 135                 140

Phe Val Glu Met Lys Gly Val Ala Ala Gly Asp Gly Arg Ala Pro Ala
145                 150                 155                 160

Val Ile Leu Gly Gly Ala Gln Met Glu Asp Phe Val Leu Asp Phe Asp
                165                 170                 175

Met Glu Lys Lys Arg Leu Gly Phe Ser Arg Leu Pro His Phe Thr Gly
            180                 185                 190

Cys Gly Gly Leu
        195
```

<210> SEQ ID NO 22
<211> LENGTH: 277
<212> TYPE: PRT
<213> ORGANISM: Aegilops tauschii
<220> FEATURE:
<221> NAME/KEY: PEPTIDE
<222> LOCATION: (1)..(277)
<223> OTHER INFORMATION: part of a xylanase inhibitor type II encoded
by SEQ ID NO 18

<400> SEQUENCE: 22

```
Ala Thr Ser Phe Tyr Thr Ile Pro Phe His Gln Gly Ala Ser Leu Val
1               5                   10                  15

Leu Asp Ile Ala Gly Pro Leu Val Trp Ser Thr Cys Gln Arg Gly Asp
            20                  25                  30

Leu Pro Thr Asp Ile Pro Cys Ser Ser Pro Thr Cys Leu Leu Ala Asn
        35                  40                  45

Ala Tyr Pro Ala Pro Gly Cys Pro Ala Pro Ser Cys Gly Ser Gly Ser
    50                  55                  60

His Asp Lys Gln Cys Thr Thr Tyr Pro Ser Asn Pro Val Thr Gly Ala
65                  70                  75                  80

Cys Ala Ala Gly Ser Leu Ala Arg Thr Thr Leu Ile Ala Asp Thr Thr
                85                  90                  95

Asp Gly Asn Asn Pro Val Ser Gln Val Tyr Val Arg Ile Leu Ala Ala
            100                 105                 110

Cys Ala Pro Arg Lys Leu Leu Ala Ser Leu Pro Arg Gly Ser Met Gly
```

```
                 115                 120                      125
Val Ala Gly Leu Gly Gly Ser Gly Leu Ala Leu Pro Ala Gln Val Ala
    130                 135                 140

Ser Thr Gln Lys Val Ala Asn Lys Phe Leu Leu Cys Leu Pro Ser Gly
145                 150                 155                 160

Gly Pro Gly Val Ala Ile Phe Gly Gly Pro Leu Pro Trp Pro Gln
                165                 170                 175

Leu Thr Gln Ser Met Pro Tyr Thr Pro Leu Val Thr Lys Gly Gly Ser
            180                 185                 190

Pro Ala His Tyr Ile Ser Val Lys Ala Ile Gln Leu Glu Asp Thr Arg
        195                 200                 205

Val Ser Val Ser Glu Arg Val Leu Ala Thr Gly Gly Val Met Leu Ser
    210                 215                 220

Thr Arg Leu Pro Tyr Ala Leu Leu Arg His Asp Val Tyr Arg Pro Leu
225                 230                 235                 240

Val Asp Ala Phe Thr Lys Ala Leu Ala Ala Gln Pro Ala Asn Gly Ala
                245                 250                 255

Pro Val Ala Arg Ala Val Lys Pro Val Ala Pro Phe Glu Leu Cys Tyr
            260                 265                 270

Asp Thr Lys Thr Leu
        275

<210> SEQ ID NO 23
<211> LENGTH: 310
<212> TYPE: DNA
<213> ORGANISM: Secale cereale
<220> FEATURE:
<221> NAME/KEY: exon
<222> LOCATION: (3)..(308)
<223> OTHER INFORMATION: internal fragment of a xylanase inhibitor gene
      termed SCXI-01 from Secale cereale cultivar Halo

<400> SEQUENCE: 23 cg caa ttc acg cag tcg atg cag tac acg ccg ctc gtc acc aag ggc         47
   Gln Phe Thr Gln Ser Met Gln Tyr Thr Pro Leu Val Thr Lys Gly
   1               5                   10                  15 ggc agc ccc gcg cac tac atc tcg ctg aag tcc atc aaa gtg gac aac        95
Gly Ser Pro Ala His Tyr Ile Ser Leu Lys Ser Ile Lys Val Asp Asn
                20                  25                  30 acc ggc gtc acc gtc tcg cag agc gcg ttc gcc acc ggc ggc gtg atg       143
Thr Gly Val Thr Val Ser Gln Ser Ala Phe Ala Thr Gly Gly Val Met
                35                  40                  45 ctg agc acg agg ctg ccc tac gcc ctg ctc cgc cgc gac gtg tac cgc       191
Leu Ser Thr Arg Leu Pro Tyr Ala Leu Leu Arg Arg Asp Val Tyr Arg
            50                  55                  60 ccg ttg gtg gac gcg ttc acc aag gcc ctg gcg gcg cag cct gcc aac       239
Pro Leu Val Asp Ala Phe Thr Lys Ala Leu Ala Ala Gln Pro Ala Asn
65                  70                  75 gga gcg ccc gtg gcg cgc gca gtg cag ccc gtg gcg ccg ttc ggg gtg       287
Gly Ala Pro Val Ala Arg Ala Val Gln Pro Val Ala Pro Phe Gly Val
80                  85                  90                  95 tgc tac gac acg aag acg ctg gg                                        310
Cys Tyr Asp Thr Lys Thr Leu
                100

<210> SEQ ID NO 24
<211> LENGTH: 310
<212> TYPE: DNA
<213> ORGANISM: Secale cereale
<220> FEATURE:
```

```
<221> NAME/KEY: exon
<222> LOCATION: (3)..(308)
<223> OTHER INFORMATION: internal fragment of a xylanase inhibitor gene
      termed SCXI-02 from Secale cereale cultivar Halo

<400> SEQUENCE: 24 cg caa ttc acg cag tcg atg cag tac acg ccg ctc gtc acc aag ggc        47
   Gln Phe Thr Gln Ser Met Gln Tyr Thr Pro Leu Val Thr Lys Gly
   1               5                  10                  15 ggc agc ccc gcg cac tac atc tcg ctc aag tcc atc aaa gtg gac aac       95
Gly Ser Pro Ala His Tyr Ile Ser Leu Lys Ser Ile Lys Val Asp Asn
                 20                  25                  30 acc ggc gtc acc ctc tcg cag agc gcg ctc gcc acc ggc ggc gtg atg      143
Thr Gly Val Thr Leu Ser Gln Ser Ala Leu Ala Thr Gly Gly Val Met
             35                  40                  45 ctc agc acg agg ctg ccc tac gcc ctg ctc cgc agc gac gtg tac cgc      191
Leu Ser Thr Arg Leu Pro Tyr Ala Leu Leu Arg Ser Asp Val Tyr Arg
         50                  55                  60 ccg ttg gtg gac gcg ttc acc aag gcc ctg gcg gcg cag cct gtc aac      239
Pro Leu Val Asp Ala Phe Thr Lys Ala Leu Ala Ala Gln Pro Val Asn
     65                  70                  75 gga gcg ccc gtg gcg cgc gcg gtg aag ccc gtg gag ccg ttc ggg gtg      287
Gly Ala Pro Val Ala Arg Ala Val Lys Pro Val Glu Pro Phe Gly Val
 80                  85                  90                  95 tgc tac gac acg aag acg ctg gg                                       310
Cys Tyr Asp Thr Lys Thr Leu
                100

<210> SEQ ID NO 25
<211> LENGTH: 102
<212> TYPE: PRT
<213> ORGANISM: Secale cereale
<220> FEATURE:
<221> NAME/KEY: PEPTIDE
<222> LOCATION: (1)..(102)
<223> OTHER INFORMATION: part of a xylanase inhibitor encoded by SEQ ID
      NO 23

<400> SEQUENCE: 25

Gln Phe Thr Gln Ser Met Gln Tyr Thr Pro Leu Val Thr Lys Gly Gly
1               5                  10                  15

Ser Pro Ala His Tyr Ile Ser Leu Lys Ser Ile Lys Val Asp Asn Thr
            20                  25                  30

Gly Val Thr Val Ser Gln Ser Ala Phe Ala Thr Gly Gly Val Met Leu
        35                  40                  45

Ser Thr Arg Leu Pro Tyr Ala Leu Leu Arg Arg Asp Val Tyr Arg Pro
    50                  55                  60

Leu Val Asp Ala Phe Thr Lys Ala Leu Ala Ala Gln Pro Ala Asn Gly
65                  70                  75                  80

Ala Pro Val Ala Arg Ala Val Gln Pro Val Ala Pro Phe Gly Val Cys
                85                  90                  95

Tyr Asp Thr Lys Thr Leu
            100

<210> SEQ ID NO 26
<211> LENGTH: 102
<212> TYPE: PRT
<213> ORGANISM: Secale cereale
<220> FEATURE:
<221> NAME/KEY: PEPTIDE
<222> LOCATION: (1)..(102)
<223> OTHER INFORMATION: part of a xylanase inhibitor encoded by SEQ ID
      NO 24
```

<400> SEQUENCE: 26

```
Gln Phe Thr Gln Ser Met Gln Tyr Thr Pro Leu Val Thr Lys Gly Gly
1               5                   10                  15
Ser Pro Ala His Tyr Ile Ser Leu Lys Ser Ile Lys Val Asp Asn Thr
            20                  25                  30
Gly Val Thr Leu Ser Gln Ser Ala Leu Ala Thr Gly Gly Val Met Leu
        35                  40                  45
Ser Thr Arg Leu Pro Tyr Ala Leu Leu Arg Ser Asp Val Tyr Arg Pro
    50                  55                  60
Leu Val Asp Ala Phe Thr Lys Ala Leu Ala Ala Gln Pro Val Asn Gly
65                  70                  75                  80
Ala Pro Val Ala Arg Ala Val Lys Pro Val Glu Pro Phe Gly Val Cys
                85                  90                  95
Tyr Asp Thr Lys Thr Leu
            100
```

<210> SEQ ID NO 27
<211> LENGTH: 226
<212> TYPE: DNA
<213> ORGANISM: Oryza sativa
<220> FEATURE:
<221> NAME/KEY: exon
<222> LOCATION: (1)..(225)
<223> OTHER INFORMATION: part of a xylanase inhibitor gene termed OSXI-01 from Oryza sativa

<400> SEQUENCE: 27

```
gcg gcg acc tcg ctc tac acc atc ccc gtc agg tac tac gac aac ctc      48
Ala Ala Thr Ser Leu Tyr Thr Ile Pro Val Arg Tyr Tyr Asp Asn Leu
1               5                   10                  15
gtc gtc gac ctc gcc ggc ccg ctc gtc tgg tcg acg tgc gcc gcc gac      96
Val Val Asp Leu Ala Gly Pro Leu Val Trp Ser Thr Cys Ala Ala Asp
            20                  25                  30
cac ctg ccg gcg tcg ctg tcc tgc cag gac ccg acg tgc gtg gtc gcc     144
His Leu Pro Ala Ser Leu Ser Cys Gln Asp Pro Thr Cys Val Val Ala
        35                  40                  45
aac gcg tac cgt gct ccg acc tgc aag gtc acc ggc ggc ggc gac         192
Asn Ala Tyr Arg Ala Pro Thr Cys Lys Val Thr Gly Gly Gly Asp
    50                  55                  60
tgc agc aag aac gtg tgc acg gcg tac ccg tac a                       226
Cys Ser Lys Asn Val Cys Thr Ala Tyr Pro Tyr
65                  70                  75
```

<210> SEQ ID NO 28
<211> LENGTH: 75
<212> TYPE: PRT
<213> ORGANISM: Oryza sativa
<220> FEATURE:
<221> NAME/KEY: PEPTIDE
<222> LOCATION: (1)..(75)
<223> OTHER INFORMATION: part of a xylanase inhibitor encoded by SEQ ID NO 27

<400> SEQUENCE: 28

```
Ala Ala Thr Ser Leu Tyr Thr Ile Pro Val Arg Tyr Tyr Asp Asn Leu
1               5                   10                  15
Val Val Asp Leu Ala Gly Pro Leu Val Trp Ser Thr Cys Ala Ala Asp
            20                  25                  30
His Leu Pro Ala Ser Leu Ser Cys Gln Asp Pro Thr Cys Val Val Ala
        35                  40                  45
```

```
Asn Ala Tyr Arg Ala Pro Thr Cys Lys Val Thr Gly Gly Gly Gly Asp
 50                  55                  60

Cys Ser Lys Asn Val Cys Thr Ala Tyr Pro Tyr
 65                  70                  75

<210> SEQ ID NO 29
<211> LENGTH: 223
<212> TYPE: DNA
<213> ORGANISM: Zea mays
<220> FEATURE:
<221> NAME/KEY: exon
<222> LOCATION: (1)..(222)
<223> OTHER INFORMATION: part of a xylanase inhibitor gene termed
      ZMXI-01 from Zea mays

<400> SEQUENCE: 29 gcc acc tcc ctc tac aca atc ccc ttc cac gac ggc gcc agc ctc gtc        48
Ala Thr Ser Leu Tyr Thr Ile Pro Phe His Asp Gly Ala Ser Leu Val
 1               5                  10                  15 ctc gac gtc gcc ggc ccg ctc gtc tgg tcc acg tgc cag cgc ggc gat        96
Leu Asp Val Ala Gly Pro Leu Val Trp Ser Thr Cys Gln Arg Gly Asp
             20                  25                  30 ctg ccg aca gat atc ccg tgc agt agc ccc acc tgc ctc ctc gcc aac       144
Leu Pro Thr Asp Ile Pro Cys Ser Ser Pro Thr Cys Leu Leu Ala Asn
         35                  40                  45 gcc tac ccc gcc ccg ggc tgc ccc gcg ccc agc tgc ggc agc gac agg       192
Ala Tyr Pro Ala Pro Gly Cys Pro Ala Pro Ser Cys Gly Ser Asp Arg
     50                  55                  60 cac gac aag ccg tgc acg gcg tac ccg tac a                             223
His Asp Lys Pro Cys Thr Ala Tyr Pro Tyr
 65                  70

<210> SEQ ID NO 30
<211> LENGTH: 74
<212> TYPE: PRT
<213> ORGANISM: Zea mays
<220> FEATURE:
<221> NAME/KEY: PEPTIDE
<222> LOCATION: (1)..(74)
<223> OTHER INFORMATION: part of a xylanase inhibitor encoded by SEQ ID
      NO 29

<400> SEQUENCE: 30

Ala Thr Ser Leu Tyr Thr Ile Pro Phe His Asp Gly Ala Ser Leu Val
 1               5                  10                  15

Leu Asp Val Ala Gly Pro Leu Val Trp Ser Thr Cys Gln Arg Gly Asp
             20                  25                  30

Leu Pro Thr Asp Ile Pro Cys Ser Ser Pro Thr Cys Leu Leu Ala Asn
         35                  40                  45

Ala Tyr Pro Ala Pro Gly Cys Pro Ala Pro Ser Cys Gly Ser Asp Arg
     50                  55                  60

His Asp Lys Pro Cys Thr Ala Tyr Pro Tyr
 65                  70

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: TAXI I
      primer 1

<400> SEQUENCE: 31
gccacctccc tctacacaat c                                                21
```

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: TAXI I
      primer 2

<400> SEQUENCE: 32
gtagtggacg aatccacctg tc                                            22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: TAXI I
      primer 3

<400> SEQUENCE: 33
cgcaattcac gcagtcgatg                                               20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: TAXI I
      primer 4

<400> SEQUENCE: 34
cccagcgtct tcgtgtcgta g                                             21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: primer 5

<400> SEQUENCE: 35
gcggcgacct cgctctacac                                               20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: primer 6

<400> SEQUENCE: 36
tgtacgggta cgccgtgca                                                19

<210> SEQ ID NO 37
<211> LENGTH: 59
<212> TYPE: DNA
<213> ORGANISM: Artificial Sequence
<220> FEATURE:
<223> OTHER INFORMATION: Description of Artificial Sequence: Forward
      primer 7

<400> SEQUENCE: 37
ccaagatctc tgccagttct ggcacctgtg accaaagatc cagcaacctc cctctacac    59

<210> SEQ ID NO 38

-continued

<211> LENGTH: 34
<212> TYPE: DNA
<213> ORGANISM: Artificial Sequence
<220> FEATURE:
<223> OTHER INFORMATION: Description of Artificial Sequence: Reverse
      Primer 8

<400> SEQUENCE: 38
cctagatctt tacaggccgc cgcaacccgt aaag                            34

<210> SEQ ID NO 39
<211> LENGTH: 1164
<212> TYPE: DNA
<213> ORGANISM: Triticum aestivum
<220> FEATURE:
<221> NAME/KEY: exon
<222> LOCATION: (10)..(1155)
<223> OTHER INFORMATION: TAXI encoding DNA sequence used in expression
      constructs (with flanking BglII restriction sites)

<400> SEQUENCE: 39

```
ccaagatct ttg cca gtt ctg gca cct gtg acc aaa gat cca gca acc tcc        51
          Leu Pro Val Leu Ala Pro Val Thr Lys Asp Pro Ala Thr Ser
           1               5                  10 ctc tac aca atc ccc ttc cac gac ggc gcc agc ctc gtc ctc gac gtc          99
Leu Tyr Thr Ile Pro Phe His Asp Gly Ala Ser Leu Val Leu Asp Val
15              20                  25                  30 gcc ggc cct ctc gtc tgg tcc acg tgc gat ggc ggc cag ccg ccc gcg        147
Ala Gly Pro Leu Val Trp Ser Thr Cys Asp Gly Gly Gln Pro Pro Ala
                35                  40                  45 gag atc ccg tgc agc agc ccc acc tgc ctc ctc gcc aac gcc tac ccc        195
Glu Ile Pro Cys Ser Ser Pro Thr Cys Leu Leu Ala Asn Ala Tyr Pro
            50                  55                  60 gcc ccg ggc tgc ccc gct ccc agc tgc ggc agc gat aag cac gac aaa        243
Ala Pro Gly Cys Pro Ala Pro Ser Cys Gly Ser Asp Lys His Asp Lys
        65                  70                  75 ccg tgc acg gcg tac ccg tac aac ccg gtc agc ggc gcg tgc gcc gca        291
Pro Cys Thr Ala Tyr Pro Tyr Asn Pro Val Ser Gly Ala Cys Ala Ala
    80                  85                  90 ggg agc ctc tcc cac acg aga ttc gtg gcc aac acc acc gac ggg agc        339
Gly Ser Leu Ser His Thr Arg Phe Val Ala Asn Thr Thr Asp Gly Ser
95                 100                 105                 110 aag ccg gtg agc aag gtg aac gtc ggg gtc ctg gca gcg tgc gcg ccg        387
Lys Pro Val Ser Lys Val Asn Val Gly Val Leu Ala Ala Cys Ala Pro
                115                 120                 125 agc aag ctc cta gcg tcg ctg ccc cgg ggc tcc acg ggc gtg gcc ggg        435
Ser Lys Leu Leu Ala Ser Leu Pro Arg Gly Ser Thr Gly Val Ala Gly
            130                 135                 140 ctc gcg aac tcc ggc ttg gcg ctg ccg gcg cag gtg gca tcc gcg cag        483
Leu Ala Asn Ser Gly Leu Ala Leu Pro Ala Gln Val Ala Ser Ala Gln
        145                 150                 155 aag gtc gcc aac agg ttc ctc ctc tgc ctc ccc acc ggc ggc cct ggc        531
Lys Val Ala Asn Arg Phe Leu Leu Cys Leu Pro Thr Gly Gly Pro Gly
    160                 165                 170 gtg gcc ata ttt ggc ggc ggc ccg gtc ccg tgg ccg caa ttc acg cag        579
Val Ala Ile Phe Gly Gly Gly Pro Val Pro Trp Pro Gln Phe Thr Gln
175                 180                 185                 190 tcg atg cct tac acg ccg ctc gtc acc aag ggc ggc agc ccc gcg cac        627
Ser Met Pro Tyr Thr Pro Leu Val Thr Lys Gly Gly Ser Pro Ala His
                195                 200                 205 tac atc tcg gcc agg tcc att gta gtg ggg gac acc cgc gtc ccc gta        675
Tyr Ile Ser Ala Arg Ser Ile Val Val Gly Asp Thr Arg Val Pro Val
            210                 215                 220
```

```
ccg gag ggc gcg ctc gcc acc ggc ggc gtg atg ctc agc acg agg cta        723
Pro Glu Gly Ala Leu Ala Thr Gly Gly Val Met Leu Ser Thr Arg Leu
        225                 230                 235 ccc tac gtc ttg ctc cgc ccc gac gtg tac cgc ccg ttg atg gac gcg        771
Pro Tyr Val Leu Leu Arg Pro Asp Val Tyr Arg Pro Leu Met Asp Ala
240                 245                 250 ttc acc aag gcc ctg gcg gcg cag cat gcc aac gga gcg ccc gtg gcg        819
Phe Thr Lys Ala Leu Ala Ala Gln His Ala Asn Gly Ala Pro Val Ala
255                 260                 265                 270 cgc gca gtg gag gct gtg gcg ccg ttc ggg gtg tgc tac gac acg aag        867
Arg Ala Val Glu Ala Val Ala Pro Phe Gly Val Cys Tyr Asp Thr Lys
                275                 280                 285 acg ctg ggc aac aac ctc ggc ggg tac gcg gtg ccc aac gtc cag ctg        915
Thr Leu Gly Asn Asn Leu Gly Gly Tyr Ala Val Pro Asn Val Gln Leu
        290                 295                 300 ggg ctc gat ggc ggc agt gac tgg acg atg acc ggg aag aac tcg atg        963
Gly Leu Asp Gly Gly Ser Asp Trp Thr Met Thr Gly Lys Asn Ser Met
        305                 310                 315 gtg gac gtc aag caa ggg acg gcg tgc gtt gcg ttc gtg gag atg aag       1011
Val Asp Val Lys Gln Gly Thr Ala Cys Val Ala Phe Val Glu Met Lys
320                 325                 330 gga gtg gcg gcc ggc gac ggc agg gcg ccg gcg gtg atc ctc gga ggg       1059
Gly Val Ala Ala Gly Asp Gly Arg Ala Pro Ala Val Ile Leu Gly Gly
335                 340                 345                 350 gcc cag atg gag gac ttc gtg ctc gac ttc gac atg gag aag aag cgg       1107
Ala Gln Met Glu Asp Phe Val Leu Asp Phe Asp Met Glu Lys Lys Arg
                355                 360                 365 ctc ggg ttt agc agg ctg ccg cac ttt acg ggt tgc ggc ggc ctg taa       1155
Leu Gly Phe Ser Arg Leu Pro His Phe Thr Gly Cys Gly Gly Leu
        370                 375                 380 agatctccg                                                              1164

<210> SEQ ID NO 40
<211> LENGTH: 863
<212> TYPE: DNA
<213> ORGANISM: Triticum aestivum
<220> FEATURE:
<221> NAME/KEY: exon
<222> LOCATION: (4)..(861)
<223> OTHER INFORMATION: part of a xylanase inhibitor gene termed
      TAXI-III from Triticum aestivum cultivar Soissons

<400> SEQUENCE: 40 gcc acc tcc ctc tac aca atc cca ttc cac tac ggc gcc aac atc gtg         48
    Thr Ser Leu Tyr Thr Ile Pro Phe His Tyr Gly Ala Asn Ile Val
    1               5                   10                  15 gtc gac acc gcc gga ccg ctc gtc tgg tcc acg tgc gca ccc gac cac         96
Val Asp Thr Ala Gly Pro Leu Val Trp Ser Thr Cys Ala Pro Asp His
                20                  25                  30 ctg ccg gcg gcg ttc ccg tgc aag agc gcc acc tgc agg ctc gcg aac        144
Leu Pro Ala Ala Phe Pro Cys Lys Ser Ala Thr Cys Arg Leu Ala Asn
            35                  40                  45 aag tac cac gtc ccg agc tgc agc gag agc gcg gct gac aag ctc tgc        192
Lys Tyr His Val Pro Ser Cys Ser Glu Ser Ala Ala Asp Lys Leu Cys
        50                  55                  60 gac cac agt cac aag gtg tgc agg gcc ttc ccg tac aac ccg gtc acc        240
Asp His Ser His Lys Val Cys Arg Ala Phe Pro Tyr Asn Pro Val Thr
65                  70                  75 ggc gcg tgc gcg gcc ggg gac ctg atc cac acc agg ttc gtc gcc aac        288
Gly Ala Cys Ala Ala Gly Asp Leu Ile His Thr Arg Phe Val Ala Asn
80                  85                  90                  95
```

```
acc acc gac gga aaa aac ccg gtg agc cag gtg aac gtt cgg gcc gtg      336
Thr Thr Asp Gly Lys Asn Pro Val Ser Gln Val Asn Val Arg Ala Val
            100                 105                 110 gcg gcg tgc gcg cca agc aaa ctc ctc gag tcg ctg ccg cag ggc gcc      384
Ala Ala Cys Ala Pro Ser Lys Leu Leu Glu Ser Leu Pro Gln Gly Ala
        115                 120                 125 tcg ggc gtg gcg ggg ctc gcg ggc tcc gac ctg gcg ctg ccg gcg cag      432
Ser Gly Val Ala Gly Leu Ala Gly Ser Asp Leu Ala Leu Pro Ala Gln
    130                 135                 140 gtg gcg tcc gag cag aag gtc tcc aac aag ttc ctc ctc tgc ctc cct      480
Val Ala Ser Glu Gln Lys Val Ser Asn Lys Phe Leu Leu Cys Leu Pro
145                 150                 155 cgc ggc ctc tca agc gac ccc ggc gtg gcc gtc ttc ggc ggc ggc ccg      528
Arg Gly Leu Ser Ser Asp Pro Gly Val Ala Val Phe Gly Gly Gly Pro
160                 165                 170                 175 ctc cac ttc atg gcg cgg ccg gag agg gac tac acg aag gag ctg gcc      576
Leu His Phe Met Ala Arg Pro Glu Arg Asp Tyr Thr Lys Glu Leu Ala
            180                 185                 190 tac acg ccg ctc gtc gcc aag aag ggc aac ccc gcg cac tac atc tcg      624
Tyr Thr Pro Leu Val Ala Lys Lys Gly Asn Pro Ala His Tyr Ile Ser
        195                 200                 205 atc aag tcc atc gcc gtg gag agc gcc cgc gtg ccc gtc ccg gcg cag      672
Ile Lys Ser Ile Ala Val Glu Ser Ala Arg Val Pro Val Pro Ala Gln
    210                 215                 220 gcg ctc gcc acc ggt ggg gcg gtg ctc tgc acg agg tcg ccc ttc acc      720
Ala Leu Ala Thr Gly Gly Ala Val Leu Cys Thr Arg Ser Pro Phe Thr
225                 230                 235 ctg ctc cgc tcc gac gtg ttc ctc ccg ttg gtg gac gcg ttc acc aag      768
Leu Leu Arg Ser Asp Val Phe Leu Pro Leu Val Asp Ala Phe Thr Lys
240                 245                 250                 255 gcc ctg gcg aag cag ggt gcg cag ggc ggg ccc gtg gcg aaa gcg gtg      816
Ala Leu Ala Lys Gln Gly Ala Gln Gly Gly Pro Val Ala Lys Ala Val
            260                 265                 270 aag ccc tac gcg ccg ttc cag ctg tgc tac gac acg aag acg ctg gg       863
Lys Pro Tyr Ala Pro Phe Gln Leu Cys Tyr Asp Thr Lys Thr Leu
        275                 280                 285

<210> SEQ ID NO 41
<211> LENGTH: 287
<212> TYPE: PRT
<213> ORGANISM: Triticum aestivum
<220> FEATURE:
<221> NAME/KEY: PEPTIDE
<222> LOCATION: (1)..(287)
<223> OTHER INFORMATION: part of a xylanase inhibitor type III encoded
      by SEQ ID NO 40

<400> SEQUENCE: 41

Ala Thr Ser Leu Tyr Thr Ile Pro Phe His Tyr Gly Ala Asn Ile Val
1               5                   10                  15

Val Asp Thr Ala Gly Pro Leu Val Trp Ser Thr Cys Ala Pro Asp His
            20                  25                  30

Leu Pro Ala Ala Phe Pro Cys Lys Ser Ala Thr Cys Arg Leu Ala Asn
        35                  40                  45

Lys Tyr His Val Pro Ser Cys Ser Glu Ser Ala Ala Asp Lys Leu Cys
    50                  55                  60

Asp His Ser His Lys Val Cys Arg Ala Phe Pro Tyr Asn Pro Val Thr
65                  70                  75                  80

Gly Ala Cys Ala Ala Gly Asp Leu Ile His Thr Arg Phe Val Ala Asn
                85                  90                  95
```

```
Thr Thr Asp Gly Lys Asn Pro Val Ser Gln Val Asn Val Arg Ala Val
            100                 105                 110
Ala Ala Cys Ala Pro Ser Lys Leu Leu Glu Ser Leu Pro Gln Gly Ala
        115                 120                 125
Ser Gly Val Ala Gly Leu Ala Gly Ser Asp Leu Ala Leu Pro Ala Gln
    130                 135                 140
Val Ala Ser Glu Gln Lys Val Ser Asn Lys Phe Leu Leu Cys Leu Pro
145                 150                 155                 160
Arg Gly Leu Ser Ser Asp Pro Gly Val Ala Val Phe Gly Gly Pro
                165                 170                 175
Leu His Phe Met Ala Arg Pro Glu Arg Asp Tyr Thr Lys Glu Leu Ala
            180                 185                 190
Tyr Thr Pro Leu Val Ala Lys Lys Gly Asn Pro Ala His Tyr Ile Ser
        195                 200                 205
Ile Lys Ser Ile Ala Val Glu Ser Ala Arg Val Pro Val Pro Ala Gln
    210                 215                 220
Ala Leu Ala Thr Gly Gly Ala Val Leu Cys Thr Arg Ser Pro Phe Thr
225                 230                 235                 240
Leu Leu Arg Ser Asp Val Phe Leu Pro Leu Val Asp Ala Phe Thr Lys
                245                 250                 255
Ala Leu Ala Lys Gln Gly Ala Gln Gly Gly Pro Val Ala Lys Ala Val
            260                 265                 270
Lys Pro Tyr Ala Pro Phe Gln Leu Cys Tyr Asp Thr Lys Thr Leu
        275                 280                 285

<210> SEQ ID NO 42
<211> LENGTH: 513
<212> TYPE: DNA
<213> ORGANISM: Avena sativa
<220> FEATURE:
<221> NAME/KEY: exon
<222> LOCATION: (3)..(512)
<223> OTHER INFORMATION: part of a xylanase inhibitor gene termed
      ASXI-01 from Avena sativa

<400> SEQUENCE: 42 tg gcg tcc gcg cag aag gtc gcc aag aag ttc ctc ctc tgc ctc tcc     47
   Ala Ser Ala Gln Lys Val Ala Lys Lys Phe Leu Leu Cys Leu Ser
   1               5                   10                  15 cgc ggc ggc gtg tac gga gac ggc gtg gcc atc ttc ggc ggc ggc ccg    95
Arg Gly Gly Val Tyr Gly Asp Gly Val Ala Ile Phe Gly Gly Gly Pro
                20                  25                  30 ctc cac ctc acc gcg cag ccg gag aca gac tac acg cag tcc ctt gag   143
Leu His Leu Thr Ala Gln Pro Glu Thr Asp Tyr Thr Gln Ser Leu Glu
            35                  40                  45 tac acg ccg ctc ttc acc aaa gaa ggc aac ccg gcg tac tac gtc tcg   191
Tyr Thr Pro Leu Phe Thr Lys Glu Gly Asn Pro Ala Tyr Tyr Val Ser
        50                  55                  60 gtc aag tcc atc gcg ctg gag aac acc ccc gtc ccc gtc tcg acc cgc   239
Val Lys Ser Ile Ala Leu Glu Asn Thr Pro Val Pro Val Ser Thr Arg
65                  70                  75 acg ctc gac gcc ggc ggt gtg gtg ctc tgc acc agg gtg cca tac acc   287
Thr Leu Asp Ala Gly Gly Val Val Leu Cys Thr Arg Val Pro Tyr Thr
80                  85                  90                  95 ttt ctc cgc ccc gac gtg tac ctc ccg ttc gcg gac gcg ttc cgc acg   335
Phe Leu Arg Pro Asp Val Tyr Leu Pro Phe Ala Asp Ala Phe Arg Thr
                100                 105                 110 gca atg aag gcg cag aag gcg caa gaa atg aag gcc gtg gcg cca ttc   383
```

```
Ala Met Lys Ala Gln Lys Ala Gln Glu Met Lys Ala Val Ala Pro Phe
            115                 120                 125
ggg ctg tgc tac aac acg tcg acg ctg gcc aac acg cgg ctc ggg tac        431
Gly Leu Cys Tyr Asn Thr Ser Thr Leu Ala Asn Thr Arg Leu Gly Tyr
        130                 135                 140
ctg gtg ccg acc gtg acg ctg gcg ctg gaa ggc ggg aag aag tgg acg        479
Leu Val Pro Thr Val Thr Leu Ala Leu Glu Gly Gly Lys Lys Trp Thr
145                 150                 155
atg acg ggc gtc cac tcg atg gtg gac gtc aag c                          513
Met Thr Gly Val His Ser Met Val Asp Val Lys
160                 165                 170
```

<210> SEQ ID NO 43
<211> LENGTH: 170
<212> TYPE: PRT
<213> ORGANISM: Avena sativa
<220> FEATURE:
<221> NAME/KEY: PEPTIDE
<222> LOCATION: (1)..(170)
<223> OTHER INFORMATION: part of a xylanase inhibitor encoded by SEQ ID
      NO 42

<400> SEQUENCE: 43

```
Ala Ser Ala Gln Lys Val Ala Lys Lys Phe Leu Leu Cys Leu Ser Arg
1               5                  10                  15

Gly Gly Val Tyr Gly Asp Gly Val Ala Ile Phe Gly Gly Pro Leu
            20                  25                  30

His Leu Thr Ala Gln Pro Glu Thr Asp Tyr Thr Gln Ser Leu Glu Tyr
            35                  40                  45

Thr Pro Leu Phe Thr Lys Glu Gly Asn Pro Ala Tyr Tyr Val Ser Val
        50                  55                  60

Lys Ser Ile Ala Leu Glu Asn Thr Pro Val Pro Val Ser Thr Arg Thr
65                  70                  75                  80

Leu Asp Ala Gly Gly Val Val Leu Cys Thr Arg Val Pro Tyr Thr Phe
                85                  90                  95

Leu Arg Pro Asp Val Tyr Leu Pro Phe Ala Asp Ala Phe Arg Thr Ala
            100                 105                 110

Met Lys Ala Gln Lys Ala Gln Glu Met Lys Ala Val Ala Pro Phe Gly
            115                 120                 125

Leu Cys Tyr Asn Thr Ser Thr Leu Ala Asn Thr Arg Leu Gly Tyr Leu
        130                 135                 140

Val Pro Thr Val Thr Leu Ala Leu Glu Gly Gly Lys Lys Trp Thr Met
145                 150                 155                 160

Thr Gly Val His Ser Met Val Asp Val Lys
                165                 170
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Primer 9

<400> SEQUENCE: 44
tggcgtccgc gcagaaggtc                                                  20

<210> SEQ ID NO 45
<211> LENGTH: 20
<212> TYPE: DNA
<213> ORGANISM: Artificial Sequence
<220> FEATURE:

-continued

<223> OTHER INFORMATION: Description of Artificial Sequence: Primer 10

<400> SEQUENCE: 45
gcttgacgtc caccatcgag                    20

What is claimed is:

1. An isolated nucleic acid molecule encoding a biologically active endoxylanase inhibitor isolated from a cereal plant having a MW of at least 40 kDa as determined by SDS-PAGE, wherein said molecule comprises a polynucleotide sequence that is at least 90% or more identical to polynucleotide sequence SEQ ID NO: 14.

2. An isolated nucleic acid molecule encoding biologically active endoxylanase inhibitor having a MW of at least 40 kDa as determined by SDS-PAGE isolated from barley, rye, rice, maize, triticale, sorgham or oats; wherein said molecule comprises a first polynucleotide sequence 90% or more identical to a second polynucleotide sequence selected from the group consisting of: (a) a polynucleotide sequence encoding amino acids 1 to 185 of SEQ ID NO: 11; (b) a polynucleotide sequence encoding amino acids 1 to 185 of SEQ ID NO: 12; (c) a polynucleotide sequence encoding amino acids 1 to 185 of SEQ ID NO: 13; (d) a polynucleotide sequence of SEQ ID NO: 14.

3. A polynucleotide sequence according to any one of the claim 1 or claim 2 operably linked to a promoter.

4. A recombinant DNA construct comprising at least one of the polynucleotide sequences of claim 1 or claim 2.

5. The transcribed RNA product of the polynucleotide of claim 1 or claim 2.

6. An RNA molecule or a fragment thereof which is antisense in relation to the RNA product of claim 1 or claim 2 and is capable of hybridising thereto.

7. A vector comprising the polynucleotide sequence according to claim 1 or claim 2.

8. A microorganism, plant, plant tissue or plant cell, transformed with the DNA molecule according to claim 1 or claim 2.

9. The microorganism, plant, plant tissue or plant cell of claim 8, wherein the DNA molecule is operably associated with a heterologous regulatory sequence.

10. Method for producing a recombinant endoxylanase inhibitor, said method comprising: culturing a host organism comprising a nucleotide molecule according to claim 1 or claim 2, under conditions suitable to produce said protein by said nucleic acid and recovering said protein.

11. An isolated nucleic acid molecule according to claim 2, comprising a first polynucleotide sequence which is at least 90% or 95% identical to said second polynucleotide.

12. An isolated nucleic acid molecule encoding a biologically active endoxylanase inhibitor isolated from a cereal plant having a MW of at least 40 kDa as determined by SDS-PAGE, wherein said molecule comprises a polynucleotide sequence that is at least 95% or more identical to polynucleotide SEQ ID NO: 14.

13. An endoxylanase inhibitor encoded by the nucleic acid molecule according to claims 1, 2 or 12.

* * * * *